US009217157B2

(12) United States Patent
Garcia-Sastre et al.

(10) Patent No.: US 9,217,157 B2
(45) Date of Patent: Dec. 22, 2015

(54) RECOMBINANT INFLUENZA VIRUSES AND USES THEREOF

(75) Inventors: Adolfo Garcia-Sastre, New York, NY (US); Peter Palese, Loonta, NJ (US); Balaji Manicassamy, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 13/387,293

(22) PCT Filed: Jul. 27, 2010

(86) PCT No.: PCT/US2010/043377
§ 371 (c)(1),
(2), (4) Date: Jun. 19, 2012

(87) PCT Pub. No.: WO2011/014504
PCT Pub. Date: Feb. 3, 2011

(65) Prior Publication Data
US 2012/0251568 A1  Oct. 4, 2012

Related U.S. Application Data

(60) Provisional application No. 61/228,965, filed on Jul. 27, 2009.

(51) Int. Cl.
| | |
|---|---|
| *A61K 39/145* | (2006.01) |
| *C12N 7/04* | (2006.01) |
| *C12N 15/44* | (2006.01) |
| *A61K 39/12* | (2006.01) |
| *C12N 7/01* | (2006.01) |
| *A61K 39/00* | (2006.01) |
| *C12N 15/86* | (2006.01) |
| *C07K 14/005* | (2006.01) |
| *C12N 7/00* | (2006.01) |

(52) U.S. Cl.
CPC .............. *C12N 15/86* (2013.01); *C07K 14/005* (2013.01); *C12N 7/00* (2013.01); *C07K 2319/50* (2013.01); *C07K 2319/60* (2013.01); *C12N 2760/16121* (2013.01); *C12N 2760/16122* (2013.01); *C12N 2760/16143* (2013.01)

(58) Field of Classification Search
CPC .............. C07K 14/005; C07K 2319/50; C07K 2319/60; C12N 2760/16143; C12N 15/86; C12N 2760/16121; C12N 2760/16122; C12N 7/00
See application file for complete search history.

(56) References Cited

U.S. PATENT DOCUMENTS

| | | | |
|---|---|---|---|
| 4,693,981 A | 9/1987 | Wiesehahn et al. | |
| 5,106,619 A | 4/1992 | Wiesehahn | |
| 5,166,057 A | 11/1992 | Palese et al. | |
| 5,413,923 A | 5/1995 | Kucherlapati et al. | |
| 5,820,871 A | 10/1998 | Palese et al. | |
| 5,854,037 A | 12/1998 | Palese et al. | |
| 5,891,705 A | 4/1999 | Budowsky | |
| 6,001,634 A | 12/1999 | Palese et al. | |
| 6,146,642 A | 11/2000 | Garcia-Sastre et al. | |
| 6,468,544 B1 | 10/2002 | Egorov et al. | |
| 6,573,079 B1 | 6/2003 | Palese et al. | |
| 6,635,246 B1 | 10/2003 | Barrett et al. | |
| 6,635,416 B2 | 10/2003 | Palese et al. | |
| 6,649,372 B1 | 11/2003 | Palese et al. | |
| 6,669,943 B1 | 12/2003 | Palese et al. | |
| 6,800,288 B2 | 10/2004 | Ferko et al. | |
| 6,852,522 B1 | 2/2005 | Palese et al. | |
| 6,866,853 B2 | 3/2005 | Egorov et al. | |
| 6,887,699 B1 | 5/2005 | Palese et al. | |
| 6,951,754 B2 | 10/2005 | Hoffmann | |
| 7,060,430 B2 | 6/2006 | Palese et al. | |
| 7,312,064 B2 | 12/2007 | Hoffmann | |
| 7,384,774 B2 | 6/2008 | Palese et al. | |

(Continued)

FOREIGN PATENT DOCUMENTS

| | | |
|---|---|---|
| EP | 0 780 475 | 8/1995 |
| EP | 0 702 085 | 1/2004 |

(Continued)

OTHER PUBLICATIONS

Basler CF, Reid AH, Dybing JK, Janczewski TA, Fanning TG, Zheng H, Salvatore M, Perdue ML, Swayne DE, Garcia-Sastre A, Palese P, Taubenberger JK. Sequence of the 1918 pandemic influenza virus nonstructural gene (NS) segment and characterization of recombinant viruses bearing the 1918 NS genes. Proc Natl Acad Sci U S A. Feb. 27, 2001;98(5):2746-51.*

(Continued)

*Primary Examiner* — Benjamin P Blumel
*Assistant Examiner* — Rachel Gill
(74) *Attorney, Agent, or Firm* — Jones Day

(57) ABSTRACT

Modified influenza virus NS gene segments and nucleic acid sequences encoding such modified influenza virus NS gene segments are described. In certain embodiments, a modified influenza virus NS gene segment comprises an influenza virus NS 1 open reading frame (ORF) lacking a stop codon, a heterologous nucleotide sequence, a 2A autoproteolytic cleavage site or another cleavage site, an NEP ORF, wherein the gene segment has one or more mutations in either the splice acceptor site, splice donor site, or both the splice acceptor and splice donor sites that prevents splicing of mRNA. Also recombinant influenza viruses comprising a modified influenza virus NS gene segment and the use of such viruses are described. The recombinant influenza viruses may be used in the prevention and/or treatment of influenza virus disease or as a delivery vector.

20 Claims, 23 Drawing Sheets

(56) References Cited

U.S. PATENT DOCUMENTS

Figure 1A:
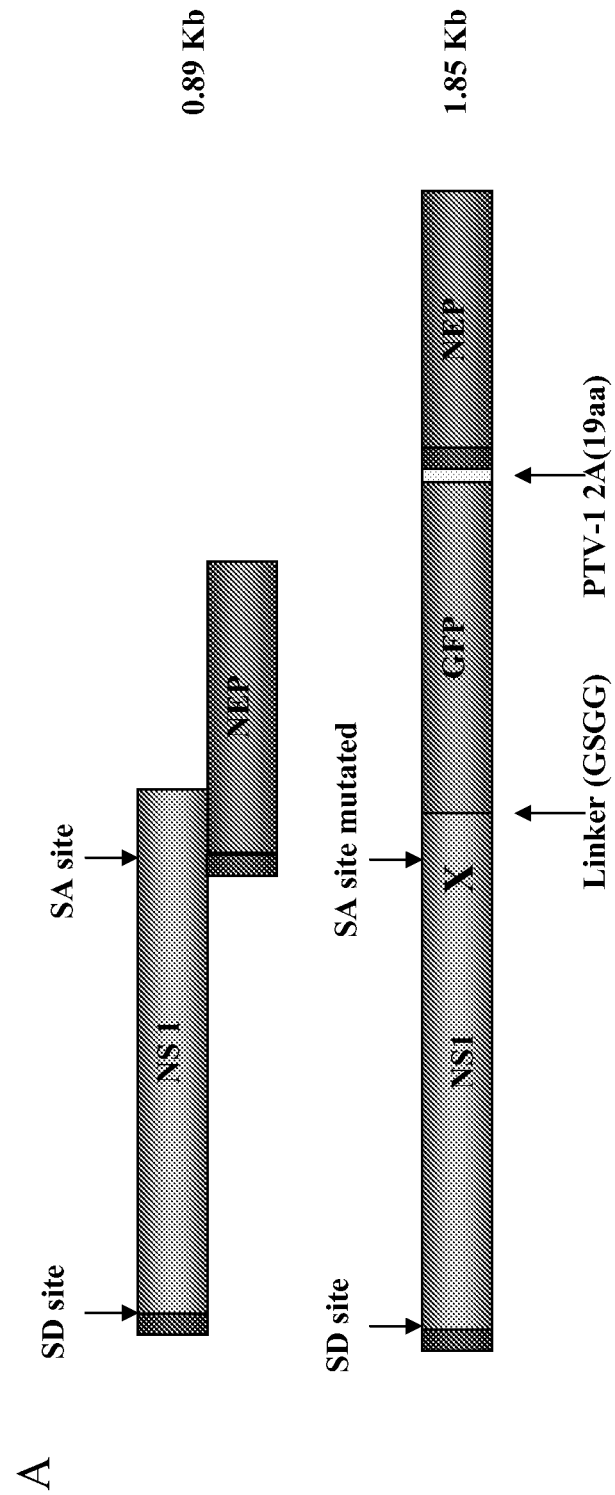

| | | | |
|---|---|---|---|
| 7,442,527 | B2 | 10/2008 | Palese et al. |
| 7,494,808 | B2 | 2/2009 | Palese et al. |
| 7,588,768 | B2 | 9/2009 | Palese et al. |
| 7,833,774 | B2 | 11/2010 | Palese et al. |
| 8,057,803 | B2 | 11/2011 | Palese et al. |
| 8,124,101 | B2 | 2/2012 | Palese et al. |
| 8,137,676 | B2 | 3/2012 | Palese et al. |
| 2009/0203114 | A1 | 8/2009 | Palese et al. |
| 2010/0158942 | A1 | 6/2010 | Palese et al. |
| 2010/0233785 | A1 | 9/2010 | Brandt et al. |
| 2012/0258134 | A1 | 10/2012 | Palese et al. |
| 2013/0034581 | A1 | 2/2013 | Palese et al. |

FOREIGN PATENT DOCUMENTS

| | | |
|---|---|---|
| WO | WO 87/05331 | 9/1987 |
| WO | WO 96/34625 | 11/1996 |
| WO | WO 97/06270 | 2/1997 |
| WO | WO 97/12032 | 4/1997 |
| WO | WO 98/02530 | 1/1998 |
| WO | WO 98/13501 | 8/1998 |
| WO | WO 98/53078 | 11/1998 |
| WO | WO 99/02657 | 1/1999 |
| WO | WO 99/15672 | 4/1999 |
| WO | WO 99/64068 | 12/1999 |
| WO | WO 99/64570 | 12/1999 |
| WO | WO 99/64571 | 12/1999 |
| WO | WO 01/04333 | 1/2001 |
| WO | WO 2006/083286 | 8/2006 |
| WO | WO 2006/088481 | 8/2006 |
| WO | WO 2007/045674 | 4/2007 |
| WO | WO 2008/032219 | 11/2008 |
| WO | WO 2009/007244 | 1/2009 |
| WO | WO 2009007244 A2 * | 1/2009 |

OTHER PUBLICATIONS

Kittel C, Ferko B, Kurz M, Voglauer R, Sereinig S, Romanova J, Stiegler G, Katinger H, Egorov A. Generation of an influenza A virus vector expressing biologically active human interleukin-2 from the NS gene segment. J Virol. Aug. 2005;79(16):10672-7.*

Kittel C, Sereinig S, Ferko B, Stasakova J, Romanova J, Wolkerstorfer A, Katinger H, Egorov A. Rescue of influenza virus expressing GFP from the NS1 reading frame. Virology. Jun. 20, 2004;324(1):67-73.*

Sereinig S, Stukova M, Zabolotnyh N, Ferko B, Kittel C, Romanova J, Vinogradova T, Katinger H, Kiselev O, Egorov A. Influenza virus NS vectors expressing the mycobacterium tuberculosis ESAT-6 protein induce CD4+ Th1 immune response and protect animals against tuberculosis challenge. Clin Vaccine Immunol. Aug. 2006;13(8):898-904.*

Donnelly ML, Hughes LE, Luke G, Mendoza H, ten Dam E, Gani D, Ryan MD. The 'cleavage' activities of foot-and-mouth disease virus 2A site-directed mutants and naturally occurring '2A-like' sequences. J Gen Virol. May 2001;82(Pt 5):1027-41.*

Fernandez-Sesma A, Marukian S, Ebersole BJ, Kaminski D, Park MS, Yuen T, Sealfon SC, Garcia-Sastre A, Moran TM. Influenza virus evades innate and adaptive immunity via the NS1 protein. J Virol. Jul. 2006;80(13):6295-304.*

Zell R, Dauber M, Krumbholz A, Henke A, Birch-Hirschfeld E, Stelzner A, Prager D, Wurm R. Porcine teschoviruses comprise at least eleven distinct serotypes: molecular and evolutionary aspects. J Virol. Feb. 2001;75(4):1620-31; NCBI GenBank Dep. No. AAK12400.*

Takasuka N, Enami M, Itamura S, Takemori T. Intranasal inoculation of a recombinant influenza virus containing exogenous nucleotides in the NS segment induces mucosal immune response against the exogenous gene product in mice. Vaccine. Feb. 22, 2002;20(11-12):1579-85.*

Bullido R, Gomez-Puertas P, Saiz MJ, Portela A. Influenza A virus NEP (NS2 protein) downregulates RNA synthesis of model template RNAs. J Virol. May 2001;75(10):4912-7.*

Baez et al., 1980. Complete nucleotide sequence of the influenza A/PR/8/34 virus NS gene and comparison with the NS genes of the A/Udorn/72 and A/FPV/Rostock/34 strains, Nucleic Acids Res. 8(23):5845-58.

Basler et al.. 2001, Sequence of the 1918 pandemic influenza virus nonstructural gene (NS) segment and characterization of recombinant viruses bearing the 1918 NS genes. Proc Natl Acad Sci U S A 98(5):2746-2751.

Billeter et al., 2009, Reverse genetics of measles virus and resulting multivalent recombinant vaccines: applications of recombinant measles viruses. Curr Top Microbiol Immunol 329:129-162.

Briedis et al., 1981. Influenza B virus genome: sequences and structural organization of RNA segment 8 and the mRNAs coding for the NS1 and NS2 proteins. J Virol. 42(1):186-93.

Buonagurio et al., 1986. Evolution of human influenza A viruses over 50 years: rapid, uniform rate of change in NS gene. Science 232(47531:980-2.

Butterfield et al., 1978, Vaccination for fowl plague. Am J Vet Res. 39(4):671-4.

Cheung et al., 2002. Induction of proinlammatory cytokines in human macrophages by influenza A (H5N1), viruses: a mechanism for the unusual severity of human disease? Lancet 360(9348):1831-1837.

Cox et al., 2005, Orthomyxoviruses: influenza IN *Topley and Wilson's Microbiology and Microbial Infections*. London: Hodder Arnold Press, pp. 634-98.

De Clercq, 2006, Antiviral agents active against influenza A viruses. Nat Rev Drug Discov 5(12):1015-1025.

De La Luna et al., 1995. Influenza virus NS1 protein enhances the rate of translation initiation of viral mRNAs. J Virol 69(4):2427-33.

Donnelly et al,. 2001, The 'cleavage' activities of foot-and-mouth disease virus 2A site-directed mutants and naturally occurring '2A-like' sequences. J Gen Virol 82(Pt 5):1027-1041.

Egorov et al., 1998. Transfectant influenza A viruses with long deletions in the NS1 protein grow efficiently in Vero cells. J Virol. 72(8):6437-41.

Egorov et al.. 1997. Generation of influenza A transfectant viruses containing deletions of the carboxyl-terminal part of the NS1 protein. Emergence and Re-emergence of Negative Strand Viruses, Tenth International Conference on Negative Strand Viruses. Sep. 21-26, Dublin, Ireland. Abstract No. 108, p. 104.

Egorov et al., 1997. Generation of Influenza A Transfectant Viruses Containing Deletions in the NS1 Protein. Institute of Applied Microbiology, Emergence and Re-emergence of Negative Strand Viruses, Tenth International Conference on Negative Strand Viruses. Sep. 21-26, Dublin, Ireland. POSTER.

Enami et al., 1991. An influenza virus containing nine different RNA segments. Virology 185(I):291-8.

Enami et al., 1991, High-efficiency formation of influenza virus transfectants. J Virol. 65(5):2711-3.

Enami et al., 1994, Influenza virus NS1 protein stimulates translation of the M1 protein. J Virol. 68(3):1432-7.

Ferko et al., 2001, Hyperattenuated Recombinant Influenza A Virus Nonstructural-Protein-Encoding Vectors Induce Human Immunodeficiency Virus Type 1 Nef-Specific Systemic and Mucosal Immune Responses in Mice. J. Virol. 75:8899-908.

Ferko et al., 2004, Immunogenicity and protection efficacy of replication-deficient influenza A viruses with altered NS1 genes. . . J Virol. 78, 23):13037-45.

Ferko et al., 2006, Live Attenuated Influenza Virus Expressing Human Interleukin-2 Reveals Increased Immunogenic Potential in Young and Aged Hosts. J. Virol. 80:11621-27.

Fesq et al., 1994, Programmed cell death (apoptosis) in human monocytes infected by influenza A virus. Immunobiology 190(1-2):175-182.

Fischer et al., 2003. Many cuts to ruin: a comprehensive update of caspase substrates, Cell Death and Differentiation 10:76-100.

Flandorfer et al., 2003, Chimeric influenza A viruses with a functional influenza B virus neuraminidase or hemagglutinin. J. Virol. 77:9116-23.

Fodor et al., 1999, Rescue of influenza A virus from recombinant DNA, J. Virol. 73:9679-82.

(56) References Cited

OTHER PUBLICATIONS

Fodor et al., 1998, Attenuation of influenza A virus mRNA levels by promoter mutations. J Virol. 72(8):6283-90.
Fortes et al., 1994. Influenza virus NS1 protein inhibits pre-mRNA splicing and blocks mRNA nucleocytoplasmic transport. EMBO J. 13(3):704-12.
Gao & Palese, 2009, Rewiring the RNAs of influenza virus to prevent reassortment. PNAS 106:15891-96.
Gao et al., 2008. A seven-segmented influenza A virus expressing the influenza C virus glycoprotein HEF. Virol 82:6419-26.
Garcia-Sastre et al 1998, Influenza A virus lacking the NS1 gene replicates in interferon-deficient systems. Virology 252(2):324-330.
Garcia-Sastre et al.. 1994. Introduction of foreign sequences into the genome of influenza A virus. Dev. Biol. Stand. 82:237-246.
García-Sastre et al., 1994, Use of a mammalian internal ribosomal entry site element for expression of A foreign protein by a transfectant influenza virus. J. Virol. 68:6254-61.
Gazit et al., 2006, Lethal influenza infection in the absence of the natural killer cell receptor gene Ncr1. Nat Immunol 7(5):517-523.
GenBank database entry CQ867238.
GenBank No. AF389122. (GI:21693177).
GenBank No. Z21498: GI: 296585.
Gibbs et al., 2003, The influenza A virus PBI-F2 protein targets the inner mitochondrial membrane via a predicted basic amphipathic helix that disrupts mitochondrial function. J. Virol. 77:7214-24.
Hale et al., 2008, The multifunctional NS1 protein of influenza A viruses. J Gen Virol 89:2359-76.
Hao et al., 2008, Differential response of respiratory dendritic cell subsets to influenza virus infection. J Virol 82(10):4908-4919.
Hayden & Pavia, 2006, Antiviral management of seasonal and pandemic influenza. J Infect Dis 194 Suppl 2:S119-126.
Haye et al., 2009, The NS1 protein of a human influenza virus inhibits type I interferon production and the induction of antiviral responses in primary human dendritic and respiratory epithelial cells. J Virol 83(13):6849-6862.
Hoffmann et al., 2000, A DNA transfection system for generation of influenza A virus from eight plasmids. Proc Natl Acad Sci U S A. 97(11):6108-13.
Ibricevic et al., 2006. Influenza virus receptor specificity and cell tropism in mouse and human airway epithelial cells. J Virol 80(15):7469-7480.
Ilyushina, 2007, Amantadine-oseltamivir combination therapy for H5N1 influenza virus infection in mice. Antivir Ther 12:363-70.
Jin et al,. 2003. Multiple amino acid residues confer temperature sensitivity to human influenza virus vaccine strains (FluMist) derived from cold-adapted A/Ann Arbor/6160. Virology 306:18-24.
Kim & Braciale, 2009, Respiratory dendritic cell subsets differ in their capacity to support the induction of virus-specific cytotoxic CD8+ T cell responses. PLoS One 4(1):e4204.
Kittel et al., 2004. Rescue of influenza virus expressing GFP from the NS1 reading frame. Virology 324: 67-73.
Kittel et al., 2005, Generation of an Influenza A Virus Vector Expressing Biologically Active Human Interleukin-2 from the NS Gene Segment, J. Virol. 79:10672-7.
Knipe, 2007, Field's Virology 5th Ed; Orthomyxoviruses.
Kochs et al., 2007, Multiple anti-interferon actions of the influenza A virus NS1 protein. J Virol 81(13):7011-7021.
Koudstaal, et al., 2009, Suitability of PER.C6 cells to generate epidemic and pandemic influenza vaccine strains by reverse genetics. Vaccine 27:2588-93.
Krug, 1995. Chapter 8. Unique Functions of the NS1 Protein Textbook of Influenza, Nicholson et al. (eds.), pp. 82-92.
Krystal, et al., 1983, Sequential mutations in the NS genes of influenza virus field strains. in J. Virol.; 45, 2):547-54.
Kumlin, et al., 2008. Sialic acid tissue distribution and influenza virus tropism. Influenza Other Respi Viruses 2:147-54.
Li et al., 1999, Recombinant influenza A virus vaccines for the pathogenic human A/Hong Kong/97 (H5N1) viruses. J. Infect. Dis. 179:1132-38.

Lopez et al., 2000, A mouse model for immunization with ex vivo virus-infected dendritic cells. Cell Immunol 206(2):107-115.
Lowen et al., 2006, The guinea pig as a transmission model for human influenza viruses. PNAS 103: 9988-92.
Manicassamy et al., 2010, Analysis of in vivo dynamics of influenza virus infection in mice using a GFP reporter virus. Proc Natl Acad Sci U S A 107:11531-6.
Marion et al., 1997, the N-terminal half of influenza virus NS1 protein is fully active both in mRNA nuclear retention and enhancement of translation. in Emergence and Re-emergence of Negative Strand Viruses, Tenth International Conference on Negative Strand Viruses., Dublin, Ireland. Abstract No. 240, p. 170.
Marion et al., 1997, The N-terminal half of the influenza virus Nsi protein is sufficient for nuclear retention of mRNA and enhancement of viral mRNA translation. Nucleic Acids Res. 25(21):4271-7.
Marsh et al.. 2008, Highly conserved regions of influenza a virus polymerase gene segments are critical for efficient viral RNA packaging. J Virol 82:2295-304.
McGill et al., 2009 Innate immune control and regulation of influenza virus infections. J Leukoc Biol 86(4):803-812.
Muramoto et al., 2006, Hierarchy among viral RNA (vRNA) segments in their role in vRNA incorporation into influenza A virions. J Virol 80:2318-25.
Nakaya et al., 2001 Recombinant Newcastle disease virus as a vaccine vector. J. Virol. 75:11868-11873.
Neumann et al., 1999, Generation of influenza A viruses entirely from cloned cDNAs. Proc Natl Acad Sci U S A 96:9345-50.
Neumann & Kawaoka, 2006, Host range restriction and pathogenicity in the context of influenza pandemic. Emerg Infect Dis 12:881-6.
Norton et al.. 1987, Infectious influenza A and B virus variants with long carboxyl terminal deletions in the NS1 polypeptides Virology 156, 2):204 13.
O'Neill et al., 1998. The influenza virus NEP (NS2 protein) mediates the nuclear export of viral ribonucleoproteins. EMBO J 17:288-96.
Palese et al.. 1999, Learning from our foes: a novel vaccine concept for influenza virus. Arch Virol Suppl. 15:131-8.
Palese & Shaw, 2007, Orthomyxoviridae: the viruses and their replication, in Howley, ed., *Fields Virology*, 5th Edition, Philadelphia, PA: Lippincott Williams & Wilkins, pp. 1647-1689.
Parvin et al., 1983, Nonsense mutations affecting the lengths of the NS1 nonstructural proteins of influenza A virus isolates Virology 128(2):512-17.
Pekosz et al., 2009, Sialic acid recognition is a key determinant of influenza A virus tropism in murine trachea epithelial cell cultures. Virology 386(1):61-67.
Perrone et al., 2008, H5N1 and 1918 pandemic influenza virus infection results in early and excessive infiltration of macrophages and neutrophils in the lungs of mice. PLoS Pathog 4(8):e1000115.
Pielak et al., 2009, Mechanism of drug inhibition and drug resistance of influenza A M2 channel. Proc Natl Acad Sci U S A 106(18):7379-7384.
Pleschka et al., 1996, A plasmid based reverse genetics system for influenza A virus. J Virol. 70(6):4188-92.
Qian et al., 1995, An amino-terminal polypeptide fragment of the influenza virus NS1 protein possesses specific RNA-binding activity and largely helical backbone structure... RNA 1:948-56.
Quinlivan et al., 2005, Attenuation of equine influenza viruses through truncations of the NS1 protein. J Virol 79(13):8431-8439.
Reed & Muench. 1938, A simple method of estimating fifty per cent endpoints. The American Journal of Hygiene 27(3):493-497.
Richt & Garcia-Sastre, 2009. Attenuated influenza virus vaccines with modified NS1 proteins, Current Topics in Microbiology and Immunology 333:177-195.
Schickli et al., 2001 Plasmid-only rescue of influenza A virus vaccine candidates. Philos Trans R Soc Lond B Biol Sci 356:1965-73.
Scull et al., 2009, Avian Influenza virus glycoproteins restrict virus replication and spread through human airway epithelium at temperatures of the proximal airways. PLoS Pathog 5(5):e1000424.
Seo et al., 2004, No apoptotic deaths and different levels of inductions of inflammatory cytokines in alveolar macrophages infected with influenza viruses. Virology 329(2):270-279.
Sereinig et al., 2006, Influenza Virus NS Vectors Expressing the Mycobacterium tuberculosis ESAT-6 Protein Induce CD4+ Th1

(56) References Cited

OTHER PUBLICATIONS

Immune Response and Protect Animals against Tuberculosis Challenge. Clinical and Vaccine Immunology 13:898-904.
Shinya et al., 2006, Avian flu: influenza virus receptors in the human airway. Nature 440(7083):435-436.
Steel et al., 2008, A combination in-ovo vaccine for avian influenza virus and Newcastle disease virus. Vaccine 26:522-31.
Stasakova et al.. 2005, Influenza A mutant viruses with altered NS1 protein function provoke caspase-1 activation in primary human macrophages, resulting in fast apoptosis and release of high levels of interleukins 1β and 18. J. Gen. Virol. 85:185-95.
Sugrue et al., 2008. Antiviral drugs for the control of pandemic influenza virus. Ann Acad Med Singapore 37(6):518-524.
Talon et al., 2000, Influenza A and B viruses expressing altered NS1 proteins: A vaccine Approach. Proc Natl Acad Sci USA 96(8):4309-14.
Tobita et al., 1990, Nucleotide sequence and some biological properties of the NS gene of a newly isolated influenza B virus mutant which has a long carboxyl terminal deletion in the NS1 protein. Virology 174(1):314-9.
Tumpey et al.. 2002, Existing antivirals are effective against influenza viruses with genes from the 1918 pandemic virus. Proc Natl Acad Sci U S A 99(21):13849-13854.
Tumpey et al., 2004, Pathogenicity and immunogenicity of influenza viruses with genes from the 1918 pandemic virus. Proc Natl Acad Sci U S A 101(9):3166-3171.
Tumpey et al., 2005. Pathogenicity of influenza viruses with genes from the 1918 pandemic virus: functional roles of alveolar macrophages and neutrophils in limiting virus replication and mortality in mice. J Virol 79(23):14933-14944.
Tumpey et al., 2000, Depletion of lymphocytes and diminished cytokine production in mice infected with a highly virulent influenza A (H5N1) virus isolated from humans. J Virol 74(13):6105-6116.
Van Riel et al., 2006 H5N1 Virus Attachment to Lower Respiratory Tract. Science 312(5772):399.
Vincent et al., 2007, Efficacy of intranasal administration of a truncated NS1 modified live influenza virus vaccine in swine. Vaccine. 25:7990-8009.
Von Itzstein, 2007. The war against influenza: discovery and development of sialidase inhibitors. Nat Rev Drug Discov 6(12):967-974.
Wang et al., 2002, Functional replacement of the carboxy-terminal two-thirds of the influenza A virus NS1 protein with short heterologous dimerization domains. J Virol. Dec:76(24):12951-62.
Wang & Duke. 2007. Cloning of the canine RNA polymerase 1 promoter and establishment of reverse genetics for influenza A and E3 in MDCK cells. Virol. J. 4:102.
Watanabe et al., 2008, Novel approach to the development of effective H5N1 influenza A virus vaccines: use of M2 cytoplasmic tail mutants. J. Virol. 82(5): 2486-2492.
Yannarell et al., 1997 Factors affecting the yield of cold-adapted influenza virus vaccine. J Virol Methods. 64 (2):161-9.
Yoshida et al., 1981, Characterization of the RNA Associated with Influenza A Cytoplasmic Inclusions and the Interaction of NS1 Protein with RNA. . . Virology 110:87-97.
Young et al. 1983, Efficient Expression of Influenza Virus NS1. Proc. Natl. Acad. Sci. 80:6105-9.
Hashimoto et al., 2007, Evidence for phagocytosis of influenza virus-infected, apoptotic cells by neutrophils and macrophages in mice. J Immunol 178(4):2448-2457.
Goodpasture et al., 1934, The cultivation of vaccine and other viruses in the chorioallantoic membrane of chick embryos. Science 74(1919):371-2.
De Felipe et al., 2006, E unum pluribus: multiple proteins from a self-processing polyprotein. Trends in Biotechnology 24(2): 68-75.

\* cited by examiner

SEQUENCE LISTING

<160> NUMBER OF SEQ ID NOS: 36

<210> SEQ ID NO 1
<211> LENGTH: 3
<212> TYPE: PRT
<213> ORGANISM: Artificial Sequence
<220> FEATURE:
<223> OTHER INFORMATION: linker sequence

<400> SEQUENCE: 1

Gly Ser Gly
 1

<210> SEQ ID NO 2
<211> LENGTH: 7
<212> TYPE: PRT
<213> ORGANISM: Artificial Sequence
<220> FEATURE:
<223> OTHER INFORMATION: linker sequence

<400> SEQUENCE: 2

Gly Ser Gly Gly Gly Ser Gly
 1               5

<210> SEQ ID NO 3
<211> LENGTH: 6
<212> TYPE: PRT
<213> ORGANISM: Artificial Sequence
<220> FEATURE:
<223> OTHER INFORMATION: linker sequence

<400> SEQUENCE: 3

Gly Ser Gly Gly Gly Gly
 1               5

<210> SEQ ID NO 4
<211> LENGTH: 18
<212> TYPE: PRT
<213> ORGANISM: Artificial Sequence
<220> FEATURE:
<223> OTHER INFORMATION: linker sequence

<400> SEQUENCE: 4

Gly Ser Gly Gly Gly Gly Gly Ser Gly Gly Gly Gly Gly Ser Gly Gly
 1               5                  10                  15

Gly Gly

<210> SEQ ID NO 5
<211> LENGTH: 4
<212> TYPE: PRT
<213> ORGANISM: Artificial Sequence
<220> FEATURE:
<223> OTHER INFORMATION: linker sequence

<400> SEQUENCE: 5

Gly Gly Gly Gly
 1

<210> SEQ ID NO 6
<211> LENGTH: 8
<212> TYPE: PRT
<213> ORGANISM: Artificial Sequence
<220> FEATURE:
<223> OTHER INFORMATION: linker sequence

<400> SEQUENCE: 6

```
Gly Gly Gly Gly Gly Gly Gly Gly
 1               5

<210> SEQ ID NO 7
<211> LENGTH: 15
<212> TYPE: PRT
<213> ORGANISM: Artificial Sequence
<220> FEATURE:
<223> OTHER INFORMATION: linker sequence

<400> SEQUENCE: 7

Gly Gly Gly Gly Ser Gly Gly Gly Ser Gly Gly Gly Gly Ser
 1               5                  10                  15

<210> SEQ ID NO 8
<211> LENGTH: 20
<212> TYPE: PRT
<213> ORGANISM: Artificial Sequence
<220> FEATURE:
<223> OTHER INFORMATION: linker sequence

<400> SEQUENCE: 8

Gly Gly Gly Gly Ser Gly Gly Gly Gly Ser Gly Gly Gly Gly Ser Gly
 1               5                  10                  15

Gly Gly Gly Ser
            20

<210> SEQ ID NO 9
<211> LENGTH: 4
<212> TYPE: PRT
<213> ORGANISM: Artificial Sequence
<220> FEATURE:
<223> OTHER INFORMATION: linker sequence

<400> SEQUENCE: 9

Glu Ala Ala Lys
 1

<210> SEQ ID NO 10
<211> LENGTH: 8
<212> TYPE: PRT
<213> ORGANISM: Artificial Sequence
<220> FEATURE:
<223> OTHER INFORMATION: linker sequence

<400> SEQUENCE: 10

Glu Ala Ala Lys Glu Ala Ala Lys
 1               5

<210> SEQ ID NO 11
<211> LENGTH: 12
<212> TYPE: PRT
<213> ORGANISM: Artificial Sequence
<220> FEATURE:
<223> OTHER INFORMATION: linker sequence

<400> SEQUENCE: 11

Glu Ala Ala Lys Glu Ala Ala Lys Glu Ala Ala Lys
 1               5                  10

<210> SEQ ID NO 12
<211> LENGTH: 16
<212> TYPE: PRT
<213> ORGANISM: Artificial Sequence
<220> FEATURE:
<223> OTHER INFORMATION: linker sequence
```

<400> SEQUENCE: 12

Glu Ala Ala Lys Glu Ala Ala Lys Glu Ala Ala Lys Glu Ala Ala Lys
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: linker sequence

<400> SEQUENCE: 13

Glu Ala Ala Lys Glu Ala Ala Lys Glu Ala Ala Lys Glu Ala Ala Lys
1               5                   10                  15

Glu Ala Ala Lys
            20

<210> SEQ ID NO 14
<211> LENGTH: 4
<212> TYPE: PRT
<213> ORGANISM: Artificial Sequence
<220> FEATURE:
<223> OTHER INFORMATION: linker sequence

<400> SEQUENCE: 14

Gly Ser Gly Gly
1

<210> SEQ ID NO 15
<211> LENGTH: 38
<212> TYPE: DNA
<213> ORGANISM: Artificial Sequence
<220> FEATURE:
<223> OTHER INFORMATION: PTV-1 2A cleavage site

<400> SEQUENCE: 15
aagaaaaccc gggcccgatg gatccaaaca ctgtgtca                           38

<210> SEQ ID NO 16
<211> LENGTH: 41
<212> TYPE: PRT
<213> ORGANISM: Artificial Sequence
<220> FEATURE:
<223> OTHER INFORMATION: PTV-1 2A cleavage site

<400> SEQUENCE: 16

Ile Ala Phe Ala Gly Ser Gly Ala Thr Asn Phe Ser Leu Leu Lys Gln
1               5                   10                  15

Ala Gly Asp Val Glu Glu Asn Pro Gly Pro Met Asp Pro Asn Thr Val
            20                  25                  30

Ser Ser Phe Gln Asp Ile Leu Leu Arg
        35                  40

<210> SEQ ID NO 17
<211> LENGTH: 20
<212> TYPE: PRT
<213> ORGANISM: Artificial Sequence
<220> FEATURE:
<223> OTHER INFORMATION: FDMV 2A cleavage site

<400> SEQUENCE: 17

Gln Leu Leu Asn Phe Asp Leu Leu Lys Leu Ala Gly Asp Val Glu Ser
1               5                   10                  15

Asn Pro Gly Pro

```
<210> SEQ ID NO 18
<211> LENGTH: 20
<212> TYPE: PRT
<213> ORGANISM: Artificial Sequence
<220> FEATURE:
<223> OTHER INFORMATION: Cardioviruses encephalomyocarditis virus EMCV
      cleavage site

<400> SEQUENCE: 18

His Tyr Ala Gly Tyr Phe Ala Asp Leu Leu Ile His Asp Ile Glu Thr
1               5                   10                  15

Asn Pro Gly Pro
            20

<210> SEQ ID NO 19
<211> LENGTH: 20
<212> TYPE: PRT
<213> ORGANISM: Artificial Sequence
<220> FEATURE:
<223> OTHER INFORMATION: Equine rhinitis A virus ERAV cleavage site

<400> SEQUENCE: 19

Gln Cys Thr Asn Tyr Ala Leu Leu Lys Leu Ala Gly Asp Val Glu Ser
1               5                   10                  15

Asn Pro Gly Pro
            20

<210> SEQ ID NO 20
<211> LENGTH: 19
<212> TYPE: PRT
<213> ORGANISM: Artificial Sequence
<220> FEATURE:
<223> OTHER INFORMATION: Porcine teschovirus PTV-1 cleavage site

<400> SEQUENCE: 20

Ala Thr Asn Phe Ser Leu Leu Lys Gln Ala Gly Asp Val Glu Glu Asn
1               5                   10                  15

Pro Gly Pro

<210> SEQ ID NO 21
<211> LENGTH: 19
<212> TYPE: PRT
<213> ORGANISM: Artificial Sequence
<220> FEATURE:
<223> OTHER INFORMATION: Drosophila C virus DrosC cleavage site

<400> SEQUENCE: 21

Ala Ala Arg Gln Met Leu Leu Leu Leu Ser Gly Asp Val Glu Thr Asn
1               5                   10                  15

Pro Gly Pro

<210> SEQ ID NO 22
<211> LENGTH: 20
<212> TYPE: PRT
<213> ORGANISM: Artificial Sequence
<220> FEATURE:
<223> OTHER INFORMATION: Thosea asigna virus TaV cleavage site

<400> SEQUENCE: 22

Arg Ala Glu Gly Arg Gly Ser Leu Leu Thr Cys Gly Asp Val Glu Glu
1               5                   10                  15

Asn Pro Gly Pro
```

```
<210> SEQ ID NO 23
<211> LENGTH: 20
<212> TYPE: PRT
<213> ORGANISM: Artificial Sequence
<220> FEATURE:
<223> OTHER INFORMATION: Infectious flacherie virus IFV cleavage site

<400> SEQUENCE: 23

Thr Arg Ala Glu Ile Glu Asp Glu Leu Ile Arg Ala Gly Ile Glu Ser
 1               5                  10                  15

Asn Pro Gly Pro
            20

<210> SEQ ID NO 24
<211> LENGTH: 20
<212> TYPE: PRT
<213> ORGANISM: Artificial Sequence
<220> FEATURE:
<223> OTHER INFORMATION: Trypanosoma cruzi AP endonuclease-like sequence
      cleavage site

<400> SEQUENCE: 24

Cys Asp Ala Gln Arg Gln Lys Leu Leu Leu Ser Gly Asp Ile Glu Gln
 1               5                  10                  15

Asn Pro Gly Pro
            20

<210> SEQ ID NO 25
<211> LENGTH: 17
<212> TYPE: PRT
<213> ORGANISM: Artificial Sequence
<220> FEATURE:
<223> OTHER INFORMATION: Foot-and-mouth disease virus P2A cleavage site

<400> SEQUENCE: 25

Asn Phe Asp Leu Leu Lys Leu Ala Gly Asp Val Glu Ser Asn Pro Gly
 1               5                  10                  15

Pro

<210> SEQ ID NO 26
<211> LENGTH: 4
<212> TYPE: PRT
<213> ORGANISM: Artificial Sequence
<220> FEATURE:
<223> OTHER INFORMATION: caspase cleavage site

<400> SEQUENCE: 26

Asp Glu Val Asp
 1

<210> SEQ ID NO 27
<211> LENGTH: 4
<212> TYPE: PRT
<213> ORGANISM: Artificial Sequence
<220> FEATURE:
<223> OTHER INFORMATION: caspase cleavage site

<400> SEQUENCE: 27

Asp Asp Val Asp
 1

<210> SEQ ID NO 28
<211> LENGTH: 4
```

```
<212> TYPE: PRT
<213> ORGANISM: Artificial Sequence
<220> FEATURE:
<223> OTHER INFORMATION: caspase cleavage site

<400> SEQUENCE: 28

Met Glu Leu Asp
 1

<210> SEQ ID NO 29
<211> LENGTH: 4
<212> TYPE: PRT
<213> ORGANISM: Artificial Sequence
<220> FEATURE:
<223> OTHER INFORMATION: caspase cleavage site

<400> SEQUENCE: 29

Ala Glu Val Asp
 1

<210> SEQ ID NO 30
<211> LENGTH: 4
<212> TYPE: PRT
<213> ORGANISM: Artificial Sequence
<220> FEATURE:
<223> OTHER INFORMATION: caspase cleavage site

<400> SEQUENCE: 30

Tyr Val His Asp
 1

<210> SEQ ID NO 31
<211> LENGTH: 4
<212> TYPE: PRT
<213> ORGANISM: Artificial Sequence
<220> FEATURE:
<223> OTHER INFORMATION: caspase cleavage site

<400> SEQUENCE: 31

Asp Glu Glu Asp
 1

<210> SEQ ID NO 32
<211> LENGTH: 4
<212> TYPE: PRT
<213> ORGANISM: Artificial Sequence
<220> FEATURE:
<223> OTHER INFORMATION: caspase cleavage site

<400> SEQUENCE: 32

Glu Ser Val Asp
 1

<210> SEQ ID NO 33
<211> LENGTH: 4
<212> TYPE: PRT
<213> ORGANISM: Artificial Sequence
<220> FEATURE:
<223> OTHER INFORMATION: ubiquitin-like protease cleavage site

<400> SEQUENCE: 33

Leu Arg Gly Gly
 1

<210> SEQ ID NO 34
<211> LENGTH: 15
<212> TYPE: DNA
```

```
<213> ORGANISM: Artificial Sequence
<220> FEATURE:
<223> OTHER INFORMATION: splice donor site for influenza virus A/Puerto
      Rico/8/34

<400> SEQUENCE: 34
ctttcaggta gattg                                                    15

<210> SEQ ID NO 35
<211> LENGTH: 41
<212> TYPE: DNA
<213> ORGANISM: Artificial Sequence
<220> FEATURE:
<223> OTHER INFORMATION: splice acceptor site for influenza virus
      A/Puerto Rico/8/34

<400> SEQUENCE: 35
caccattgcc ttctcttcca ggacatactg ctgaggatgt c                        41

<210> SEQ ID NO 36
<211> LENGTH: 8
<212> TYPE: PRT
<213> ORGANISM: Artificial Sequence
<220> FEATURE:
<223> OTHER INFORMATION: 2A-like sequence
<220> FEATURE:
<221> NAME/KEY: VARIANT
<222> LOCATION: 2, 4
<223> OTHER INFORMATION: Xaa = Any Amino Acid

<400> SEQUENCE: 36

Asp Xaa Glu Xaa Asn Pro Gly Pro
 1               5
```

RECOMBINANT INFLUENZA VIRUSES AND USES THEREOF

This application is the national stage entry of international patent application No. PCT/US2010/043377, filed Jul. 27, 2010, which claims priority to U.S. provisional application No. 61/228,965, filed Jul. 27, 2009, each of which is incorporated herein by reference in its entirety.

This invention was made, in part, with United States Government support under award number HHSN2662007010C from the National Institutes of Health and award numbers U19AI083025, P01AI058113 and R01AI046954 from the National Institutes of Allergy and Infectious Disease. The United States Government has certain rights to this invention.

1. INTRODUCTION

Described herein are modified influenza virus NS gene segments and nucleic acid sequences encoding such modified influenza virus NS gene segments. In certain embodiments, a modified influenza virus NS gene segment described herein comprises an influenza virus NS1 open reading frame (ORF) lacking a stop codon, a heterologous nucleotide sequence, a 2A autoproteolytic cleavage site or another cleavage site, an NEP ORF, wherein the gene segment has one or more mutations in either the splice acceptor site, splice donor site, or both the splice acceptor and splice donor sites that prevents splicing of mRNA. Also described herein are recombinant influenza viruses comprising a modified influenza virus NS gene segment and the use of such viruses. The recombinant influenza viruses may be use in the prevention and/or treatment of influenza virus disease or as a delivery vector.

2. BACKGROUND

Influenza A virus infection is one of the major causes of human respiratory diseases with an average mortality rate of 36,000/year in the United States alone (CDC, 2007). Respiratory disease caused by Influenza A virus infection can be very severe especially in very young children and the elderly (Fiore et al., 2008, "Prevention and control of influenza: recommendations of the Advisory Committee on Immunization Practices (ACIP)," MMWR Recomm Rep 57(RR-7):1-60). Apart from yearly seasonal outbreaks, IAV can cause frequent epidemics and occasional pandemics in humans (Cox et al., 2005, "Orthomyxoviruses: influenza," IN Topley and Wilson's Microbiology and Microbial Infections. London: Hodder Arnold Press, pp. 634-98; and Palese & Shaw, 2007, "Orthomyxoviridae: the viruses and their replication," In Howley, ed., Fields Virology, 5th Edition, Philadelphia, Pa.: Lippincott Williams & Wilkins, pp 1647-1689). The recent emergence of highly pathogenic avian H5N1 virus and the pandemic swine-origin 2009 A (H1N1) influenza virus underscore the threat posed by influenza viruses not only to humans but also to domestic animals and birds (Beigel, J. H., J. Farrar, A. M. Han, F. G. Hayden, R. Hyer, M. D. de Jong, S. Lochindarat, T. K. Nguyen, T. H. Nguyen, T. H. Tran, A. Nicoll, S. Touch, and K. Y. Yuen. 2005. Avian influenza A (H5N1) infection in humans. N Engl J Med 353:1374-85, Korteweg, C., and J. Gu. 2008. Pathology, molecular biology, and pathogenesis of avian influenza A (H5N1) infection in humans. Am J Pathol 172:1155-70, Ong, C. W., K. Y. Ho, L. Y. Hsu, A. Y. Lim, D. A. Fisher, and P. A. Tambyah. 2009. Reacting to the emergence of swine-origin influenza A H1N1. Lancet Infect Dis 9:397-8). Vaccination has been one of the most effective means of protection against influenza virus infection. In addition, there are two categories of FDA approved drugs used for treatment of IAV infections, M2 inhibitors, which block viral uncoating and entry (amantadine and rimantadine) and NA inhibitors, which block viral spreading (oseltamivir and zanamivir; reviewed in von Itzstein, 2007, "The war against influenza: discovery and development of sialidase inhibitors," Nat Rev Drug Discov 6(12):967-974; De Clercq, 2006, "Antiviral agents active against influenza A viruses," Nat Rev Drug Discov 5(12): 1015-1025; Hayden & Pavia, 2006, "Antiviral management of seasonal and pandemic influenza," J Infect Dis 194 Suppl 2:S119-126; Sugrue et al., 2008, "Antiviral drugs for the control of pandemic influenza virus," Ann Acad Med Singapore 37(6):518-524). However, Influenza virus undergoes rapid antigenic evolution through constant genetic reassortment and by accumulating mutations. Consequently, the imperative need for new vaccine strategies and annual vaccination puts an enormous burden on the healthcare system.

Influenza A virus, a member of the Orthomyxovirus family, is an enveloped virus. Its genome consists of eight single-stranded, negative sense RNA segments (PB1, PB2, PA, HA, NP, NA, M and NS) (Palese, P., and M. L. Shaw. 2007. Orthomyxoviridae: the viruses and their replication, p. 1647-1689. In D. M. K. P. M. Howley (ed.), Fields virology, 5th Edition ed. Lippincott Williams & Wilkins, Philadelphia, Pa.). During infection 10 or 11 viral proteins are expressed in the cells. The M and NS segments express two proteins each from alternatively spliced mRNAs (Gibbs, J. S., D. Malide, F. Hornung, J. R. Bennink, and J. W. Yewdell. 2003.) The influenza A virus PB1-F2 protein targets the inner mitochondrial membrane via a predicted basic amphipathic helix that disrupts mitochondrial function. J Virol 77:7214-24). NS1 and NEP are made from the NS segment, the smallest segment in influenza virus. NS1 is a multifunctional protein that counteracts host antiviral response by blocking numerous pathways (Hale, B. G., R. E. Randall, J. Ortin, and D. Jackson. 2008. The multifunctional NS1 protein of influenza A viruses. J Gen Virol 89:2359-76). NEP is involved in the export of vRNA from the nucleus (O'Neill, R. E., J. Talon, and P. Palese. 1998. The influenza virus NEP (NS2 protein) mediates the nuclear export of viral ribonucleoproteins. EMBO J 17:288-96). Development of a reverse genetics system for influenza viruses has tremendously helped in the identification of several viral genetic factors that contribute to severe pathogenicity (Fodor, E., L. Devenish, O. G. Engelhardt, P. Palese, G. G. Brownlee, and A. Garcia-Sastre. 1999. Rescue of influenza A virus from recombinant DNA. J Virol 73:9679-82, Neumann, G., T. Watanabe, H. Ito, S. Watanabe, H. Goto, P. Gao, M. Hughes, D. R. Perez, R. Donis, E. Hoffmann, G. Hobom, and Y. Kawaoka. 1999. Generation of influenza A viruses entirely from cloned cDNAs. Proc Natl Acad Sci USA 96:9345-50), as well as in the study different aspects of the virus life cycle. The reverse genetics system can also be used for faster generation of pandemic vaccines and development influenza based vaccine (Gao, Q., E. W. Brydon, and P. Palese. 2008. A seven-segmented influenza A virus expressing the influenza C virus glycoprotein HEF. J Virol 82:6419-26, Koudstaal, W., L. Hartgroves, M. Havenga, I. Legastelois, C. Ophorst, M. Sieuwerts, D. Zuijdgeest, R. Vogels, J. Custers, E. de Boer-Luijtze, O. de Leeuw, L. Cornelissen, J. Goudsmit, and W. Barclay. 2009. Suitability of PER.C6 cells to generate epidemic and pandemic influenza vaccine strains by reverse genetics. Vaccine 27:2588-93, Steel, J., S. V. Burmakina, C. Thomas, E. Spackman, A. Garcia-Sastre, D. E. Swayne, and P. Palese. 2008. A combination in-ovo vaccine for avian influenza virus and Newcastle disease virus. Vaccine 26:522-31).

Influenza viruses use sialic acid as cellular receptors to enter target cells (Palese, P., and M. L. Shaw. 2007. Orthomyxoviridae: the viruses and their replication, p. 1647-1689. In D. M. K. P. M. Howley (ed.), Fields virology, 5th Edition ed. Lippincott Williams & Wilkins, Philadelphia, Pa.). Several studies have shown that influenza virus can infect a variety of cell types, both in vitro and in vivo (Hao, X., T. S. Kim, and T. J. Braciale. 2008. Differential response of respiratory dendritic cell subsets to influenza virus infection. J Virol 82:4908-19, Kim, T. S., and T. J. Braciale. 2009. Respiratory dendritic cell subsets differ in their capacity to support the induction of virus-specific cytotoxic CD8+ T cell responses. PLoS One 4:e4204, Kumlin, U., S. Olofsson, K. Dimock, and N. Arnberg. 2008. Sialic acid tissue distribution and influenza virus tropism. Influenza Other Respi Viruses 2:147-54).

Although studies of influenza A virus using animal models and tissue culture have provided tremendous knowledge about both the virus and host factors which determine pathogenesis, following viral infection and pathogenesis in vivo may provide us with a better picture of the complex interactions between the virus and the host (8). Such in vivo studies have been hampered primarily due to the lack of fully competent reporter viruses (Knipe, D. M. 2007. Field's Virology 5th Ed; Orthomyxoviruses, Neumann, G., and Y. Kawaoka. 2006. Host range restriction and pathogenicity in the context of influenza pandemic. Emerg Infect Dis 12:881-6).

3. SUMMARY

In one aspect, provided herein are nucleic acid sequences comprising or consisting of a modified influenza virus NS gene segment (genomic RNA) or the complement thereof (antigenomic RNA). The modified influenza virus NS gene segments described herein not only comprise the NS1 and NEP open reading frames but also a heterologous nucleotide sequence. In specific embodiments, the modified influenza virus NS gene segments comprise an influenza virus NS1 open reading frame, a heterologous nucleotide sequence, an influenza virus NEP open reading frame, and a 2A autoproteolytic cleavage site or another cleavage site. In specific embodiments, the NS1 ORF of the modified influenza virus NS gene segments lacks a stop codon in order to produce a polyprotein that can then be cleaved by autocleavage or a protease found in the cell containing the gene segment. In addition, in specific embodiments, a heterologous nucleotide sequence of the modified influenza virus NS1 gene segments does not contain a stop codon. Some of the modified influenza virus NS gene segments described herein also comprise a linker sequence and depending upon whether or not the modified influenza virus NS gene segment comprises the entire influenza virus NS1 open reading frame or a fragment thereof, either the splice acceptor site, the splice donor site, or both the splice acceptor and splice donor sites might be mutated in order to prevent splicing the mRNA. The linker sequence is generally added to ensure proper folding of the protein encoded by either the NS1 ORF, the heterologous nucleotide sequence, and/or the NEP ORF.

In one embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic cleavage site or another cleavage site, and an influenza virus NEP ORF. In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic cleavage site or another cleavage site, and an influenza virus NEP ORF, and wherein the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a linker sequence, a 2A autoproteolytic cleavage site or another cleavage site, and an influenza virus NEP ORF. In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, heterologous nucleotide sequence, a linker sequence, a 2A autoproteolytic cleavage site or another cleavage site, and an influenza virus NEP ORF, and wherein the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a linker, a heterologous nucleotide sequence, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a heterologous nucleotide sequence, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of a heterologous nucleotide sequence, a 2A autoproteolytic cleavage site or another cleavage site, an influenza virus NS1 ORF lacking a stop codon, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a first heterologous nucleotide sequence, a 2A autoproteolytic cleavage site or another cleavage site, a second heterologous nucleotide sequence, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order. In some embodiments, the first and second heterologous nucleotide sequences encode different peptides or polypeptides. In other embodiments, the first and second heterologous nucleotide sequences encode the same peptide or polypeptide.

In another aspect, provided herein are nucleic acid sequences encoding a nucleotide sequence comprising or consisting of a modified influenza virus NS gene segment (genomic RNA) or the complement thereof (antigenomic RNA). In one embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic cleavage site or other cleavage site, and an influenza virus NEP ORF. In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic cleavage site or another cleavage site, and an influenza virus NEP ORF, and wherein the modified NS gene segment has one or more mutations in either the splice acceptor site, the splice donor site or both the splice acceptor and the splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a linker sequence, a 2A autoproteolytic cleavage site or another cleavage site, and an NEP ORF. In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a linker sequence, a 2A autoproteolytic cleavage site or other cleavage site, and an NEP ORF, and wherein the modified NS gene segment has one or more mutations in either the splice acceptor site, the splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a linker, a heterologous nucleotide sequence, a 2A autoproteolytic cleavage site or another cleavage site, and an influenza virus NEP ORF. In certain embodiments, the modified NS gene segment has one or more mutations in either the splice acceptor site, the splice donor site or both the splice acceptor and the splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a heterologous nucleotide sequence, a 2A autoproteolytic cleavage site or another cleavage site, and an influenza virus NEP ORF. In certain embodiments, the modified NS gene segment has one or more mutations in either the acceptor site, the splice donor site, or both the splice acceptor and splice donor sties that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of heterologous nucleotide sequence, a 2A autoproteolytic cleavage site or another cleavage site, an influenza virus NS1 ORF lacking a stop codon, a 2A autoproteolytic cleavage site or another cleavage site, and an influenza virus NEP ORF. In certain embodiments, the modified NS gene segment has one or more mutations in either the splice acceptor site, the splice donor site, or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a first heterologous nucleotide sequence, a 2A autoproteolytic cleavage site or another cleavage site, a second heterologous nucleotide sequence, a 2A autoproteolytic cleavage site or another cleavage site, and an influenza virus NEP ORF. In certain embodiments, the modified NS gene segment has one or more mutations in either the splice acceptor site, the splice donor site or both the splice acceptor and splice donor sites that prevents splicing of mRNA. In certain embodiments, the components of the modified influenza virus gene segment are in the order that they are listed in 3' to 5' order. In some embodiments, the first and second heterologous nucleotide sequences encode different peptides or polypeptides. In other embodiments, the first and second heterologous nucleotide sequences encode the same peptides or polypeptides.

In another aspect, provided herein are recombinant influenza viruses comprising a modified influenza virus NS gene segment described herein. In some embodiments, a recombinant influenza virus comprising a modified influenza virus NS gene segment described herein is replication competent. In specific embodiments, a recombinant influenza virus comprising a modified influenza virus NS gene segment described herein achieves titers of approximately $3 \times 10^5$ pfu/ml, $3.5 \times 10^5$ pfu/ml, $4 \times 10^5$ pfu/ml, $5 \times 10^5$ pfu/ml, $1 \times 10^6$ pfu/ml, $5 \times 10^6$ pfu/ml, $1 \times 10^7$ pfu/ml, $5 \times 10^7$ pfu/ml, $1 \times 10^8$ pfu/ml, $5 \times 10^8$ pfu/ml, $1 \times 10^9$ pfu/ml or more after 1, 2, 3, 4, 5, 6, 7, 8, 9, 10 or more passages in cells (e.g., MDCK cells) or embryonated chick eggs. In certain embodiments, a recombinant influenza virus described herein comprises an attenuating mutation.

In another aspect, provided herein are substrates (e.g., host cells and eggs) comprising a nucleic acid sequence described herein. In one embodiment, provided herein are substrates comprising a modified influenza virus NS gene segment or a complement thereof. In another embodiment, provided herein are substrates comprising a nucleic acid sequence, wherein the nucleic acid sequence comprises a nucleotide sequence encoding a modified influenza virus NS gene segment or a complement thereof.

In another aspect, provided herein are substrates comprising a recombinant influenza virus, wherein the recombinant influenza virus comprises a modified influenza virus NS gene segments described herein. In another aspect, provided herein are compositions comprising a recombinant influenza virus, wherein the recombinant influenza virus comprises a modified influenza virus NS gene segments described herein.

In another aspect, provided herein are kits comprising a nucleic acid sequence or recombinant influenza virus described herein. In one embodiment, a kit provided herein comprises, in one or more containers, a nucleic acid sequence described herein. In another embodiment, a kit provided herein, comprises, in one or more containers, a recombinant influenza virus described herein.

In yet another aspect, provided herein are methods of using a recombinant influenza virus, wherein the recombinant influenza virus comprises a modified influenza virus NS gene segment. In one embodiment, provided herein is a method for eliciting an immune response against an influenza virus in a subject, wherein the method comprises administering a recombinant influenza virus described herein or a composition thereof to the subject. In another embodiment, provided herein is a method of preventing and/treating an influenza virus infection in a subject, wherein the method comprises administering a recombinant influenza virus described herein or a composition thereof to the subject. In another embodiment, provided herein is a method for preventing and/or treating an influenza virus disease in a subject, wherein the method comprises administering a recombinant influenza virus described herein or a composition thereof to the subject.

In another embodiment, provided herein are methods for eliciting an immune response against an antigen in a subject, comprising administering a recombinant influenza virus described herein or a composition thereof to the subject. In another embodiment, provided herein are methods for generating or identifying antibodies that bind to an influenza virus utilizing a recombinant influenza virus described herein or a composition thereof.

In another aspect, the recombinant influenza viruses described herein can be used to assess the antiviral activity of a compound or understand the life cycle of an influenza virus.

3.1 Terminology

As used herein, the term "about" or "approximately" when used in conjunction with a number refers to any number within 1, 5 or 10% of the referenced number.

As used herein, the term "effective amount" in the context of administering a therapy to a subject refers to the amount of a therapy which has a prophylactic and/or therapeutic effect(s). In certain embodiments, in the context of administration of a therapy to a subject refers to the amount of a therapy which is sufficient to achieve one, two, three, four, or more of the following effects: (i) reduction or amelioration in the severity of a disease or a symptom associated therewith; (ii) reduction in the duration of a disease or a symptom associated therewith; (iii) prevention of the progression of a disease or a symptom associated therewith; (iv) regression of a disease or a symptom associated therewith; (v) prevention of the development or onset of a disease or a symptom associated therewith; (vi) prevention of the recurrence of a disease or a symptom associated therewith; (vii) reduction in organ failure associated with a disease; (viii) reduction in the hospitalization of a subject; (ix) reduction in the hospitalization length; (x) an increase in the survival of a subject with a disease; (xi) elimination of a disease; (xi) inhibition or reduction in replication of a pathogen; (xii) inhibition or reduction in the spread or transmission of a pathogen from one cell, one tissue or one organ to another cell, tissue or organ; (xiii) inhibition or reduction in the spread or transmission from one subject to another subject; (xiv) reduction in pathogen numbers; (xv) reduction in the number of symptoms associated with a disease; and (xvi) enhancement, improvement, supplementation, complementation, or augmentation of the prophylactic or therapeutic effect(s) of another therapy.

In specific embodiments, an "effective amount" in the context of administration of a therapy to a subject refers to the amount of a therapy which is sufficient to achieve one, two, three, four, or more of the following effects: (i) reduction or amelioration in the severity of an influenza virus infection, an influenza virus disease or symptom associated therewith; (ii) reduction in the duration of an influenza virus infection, an influenza virus disease or symptom associated therewith; (iii) prevention of the progression of an influenza virus infection, an influenza virus disease or symptom associated therewith; (iv) regression of an influenza virus infection, an influenza virus disease or symptom associated therewith; (v) prevention of the development or onset of an influenza virus infection, an influenza virus disease or symptom associated therewith; (vi) prevention of the recurrence of an influenza virus infection, an influenza virus disease or symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of the replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) reduction in the number of symptoms associated with an influenza virus infection or an influenza virus disease; (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections. Exemplary doses of an effective amount are provided herein below.

In certain embodiments, the effective amount of a therapy does not result in complete protection from an influenza virus disease, but results in a lower titer or reduced number of influenza viruses compared to an untreated subject. In certain embodiments, the effective amount of a therapy results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In certain embodiments, the effective amount of a therapy results in a reduction by 0.5 log, 1 log, 2 logs, 3 logs, 4 logs, 5, logs, 6, logs, 7 logs, or 10 logs or more in titer of influenza virus relative to an untreated subject. Benefits of a reduction in the titer, number or total burden of influenza virus include, but are not limited to, less severe symptoms of the infection, fewer symptoms of the infection, reduction in the length of the disease associated with the infection, and prevention of the onset or diminution of disease severity of bacterial pneumonias occurring secondary to influenza virus infections.

As used herein, the term "elderly human" refers to a human 65 years or older.

As used herein, the term "fragment" in the context of a nucleic acid sequence refers to a nucleotide sequence comprising at least 2 or at least 3 consecutive nucleotides from a parent sequence. In a specific embodiment, the term refers to a nucleotide sequence of 2 to 30, 5 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence.

As used herein, the term "fragment" in the context of an amino acid sequence refers to an amino acid sequence comprising at least 2 consecutive amino acid residues from a parent sequence. In a specific embodiment, the term refers to an amino acid sequence of 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive amino acid residues of a parent sequence.

As used herein, the term "heterologous" refers to a unit that is not found naturally be associated with another unit. For example, a first nucleotide sequence is said be a heterologous to a second nucleotide sequence if the two nucleotide sequences are not found in nature to be associated with each other.

As used herein, the term "host cell" refers to any type of cell, e.g., a primary cell or a cell from a cell line. In specific embodiments, the term "host cell" refers a cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "human adult" refers to a human that is 18 years or older.

As used herein, the term "human child" refers to a human that is 1 year to 18 years old.

As used herein, the term "human infant" refers to a newborn to 1 year old human.

As used herein, the term "in combination" in the context of the administration of a therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" and phrases referring to a disease associated with an influenza virus infection refer to the pathological state resulting from the presence of an influenza virus (e.g., influenza A or B virus) in a cell or subject or the invasion of a cell or subject by an influenza virus. In specific embodiments, the term refers to a respiratory illness caused by an influenza virus.

As used herein, the phrases "IFN-deficient systems" or "IFN-deficient substrates" refer to systems, e.g., cells, cell lines and animals, such as mice, chickens, turkeys, rabbits, rats, horses etc., which (a) do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), (b) do not respond or respond less efficiently to one, two or more types of IFN, or do not respond to any type of IFN, and/or (c) are deficient in the activity of antiviral genes induced by one, two or more types of IFN, or induced by any type of IFN.

An "isolated" protein (e.g., an antibody) is substantially free of cellular material or heterologous proteins (also referred to herein as contaminating proteins) from the cell or tissue source from which the protein is derived, or substantially free of chemical precursors or other chemicals when chemically synthesized. The language "substantially free of cellular material" includes preparations of a protein (e.g., an antibody) in which the protein is separated from cellular components of the cells from which it is isolated or recombinantly produced. Thus, a protein (e.g., an antibody) that is substantially free of cellular material includes preparations of protein having less than about 30%, 20%, 10%, or 5% (by dry weight) of heterologous protein. When the protein is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the protein of interest. In another specific embodiment, antibodies described herein are isolated.

As used herein, the term "isolated" in the context of nucleic acids refers to a nucleic acid molecule which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized; however, "isolated" excludes members of a library of clones such as a cDNA library. In a specific embodiment, a nucleic acid described herein is isolated. In another specific embodiment, antibodies described herein are isolated. The language "substantially free of other cellular material" includes preparations of a nucleic acid molecule in which the nucleic acid molecule is separated from cellular components of the cells from which it is isolated or recombinantly produced. Thus, a nucleic acid molecule that is substantially free of cellular material includes preparations having less than about 30%, 20%, 10%, or 5% (by dry weight) of heterologous nucleic acid molecules or other cellular components. When the nucleic acid molecule is recombinantly produced, it is also preferably substantially free of culture medium, i.e., culture medium represents less than about 20%, 10%, or 5% of the volume of the nucleic acid molecule preparation. When the nucleic acid molecule is produced by chemical synthesis, it is preferably substantially free of chemical precursors or other chemicals, i.e., it is separated from chemical precursors or other chemicals which are involved in the synthesis of the nucleic acid molecule. Accordingly such preparations of the nucleic acid molecule have less than about 30%, 20%, 10%, 5% (by dry weight) of chemical precursors or compounds other than the nucleic acid molecule of interest.

As used herein, the phrase "multiplicity of infection" or "MOI" is the average number of virus per infected cell. The MOI is determined by dividing the number of virus added (ml added x plaque forming units (pfu)) by the number of cells added (ml added x cells/ml).

As used herein, the term "N-terminus" and the like in the context of NS1 refers to the first 300 nucleotides of NS1 starting from the amino-terminus of NS1.

As used herein, the term "C-terminus" and the like in the context of NS1 refers to the first 300 nucleotides of NS1 starting from the stop codon of NS1.

As used herein, the terms "nucleic acid" and "nucleotides" refer to deoxyribonucleotides, deoxyribonucleic acids, ribonucleotides, and ribonucleic acids, and polymeric forms thereof, and includes either single- or double-stranded forms. In certain embodiments, such terms include known analogues of natural nucleotides, for example, peptide nucleic acids ("PNA"s), that have similar binding properties as the reference nucleic acid. In some embodiments, such terms refers to deoxyribonucleic acids (e.g., cDNA or DNA). In other embodiments, such terms refers to ribonucleic acids (e.g., mRNA or RNA).

As used herein, the terms "prevent," "preventing" and "prevention" in the context of the administration of a therapy(ies) to a subject refer to a prophylactic effect that results from the administration of a therapy or a combination of therapies. In a specific embodiment, the terms "prevent," "preventing" and "prevention" in the context of the administration of a therapy(ies) to a subject to prevent a disease refer to one or more of the following effects resulting from the administration of a therapy or a combination of therapies: (i) the inhibition or reduction in the development or onset of a disease or a symptom thereof (e.g., fever, myalgia, edema, inflammatory infiltrates); (ii) the inhibition or reduction in the recurrence of a disease or a symptom associated therewith; and (iii) the reduction or inhibition in a pathogen infection and/or replication. In other specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition or reduction in the development or onset of an influenza virus disease or a symptom thereof (e.g., fever, myalgia, edema, inflammatory infiltrates); (ii) the inhibition or reduction in the recurrence of an influenza virus disease or a symptom associated therewith; and (iii) the reduction or inhibition in influenza virus infection and/or replication.

In another specific embodiment, the terms "prevent", "preventing" and "prevention" in the context of the administration of a therapy(ies) to a subject to prevent an influenza virus infection refer to one or more of the following effects resulting from the administration of a therapy or a combination of therapies: (i) the reduction or inhibition of the spread of influenza virus from one cell to another cell; (ii) the reduction or inhibition of the spread of influenza virus from one organ or tissue to another organ or tissue; and/or (iii) the reduction or inhibition of the spread of influenza virus from one region of an organ or tissue to another region of the organ or tissue (e.g., the reduction in the spread of influenza virus from the upper to the lower respiratory tract).

As used herein, the terms "subject" and "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In another embodiment, a subject is a non-human mammal. In another embodiment, a subject is a human. In another embodiment, a subject is a human infant. In another embodiment, a subject is a human child. In another embodiment, the subject is a human adult. In another embodiment, a subject is an elderly human.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to an immunogenic composition (e.g., an influenza virus vaccine).

As used herein, the terms "treat," "treatment," and "treating" in the context of the administration of a therapy(ies) to a subject refer a beneficial or therapeutic effect resulting from the administration of a therapy or a combination of therapies. In specific embodiments, such terms refer to one, two, three, four, five or more of the following effects resulting from the administration of a therapy or a combination of therapies: (i) reduction or amelioration in the severity of a disease or a symptom associated therewith; (ii) reduction in the duration of a disease or a symptom associated therewith; (iii) prevention of the progression of a disease or symptom associated therewith; (iv) regression of a disease or a symptom associated therewith; (v) prevention of the development or onset of a disease or a symptom associated therewith; (vi) prevention of the recurrence of a disease or a symptom associated therewith; (vii) reduction or prevention of the spread of a pathogen from one cell to another cell, one tissue to another tissue, or one organ to another organ; (viii) prevention or reduction of the spread/transmission of a pathogen from one subject to another subject; (ix) reduction in organ failure associated with a disease; (x) reduction in the hospitalization of a subject; (xi) reduction in the hospitalization length; (xii) an increase in the survival of a subject with a disease associated therewith; (xiii) elimination of a disease; (xiv) inhibition or reduction in pathogen replication; (xv) reduction in pathogen numbers; (xv) the reduction in the number of symptoms associated with a disease; and (xvi) enhancement, improvement, supplementation, complementation, or augmentation of the prophylactic or therapeutic effect(s) of another therapy.

In specific embodiments, such terms refer to one, two, three, four, five or more of the following effects resulting from the administration of a therapy or a combination of therapies: (i) reduction or amelioration in the severity of an influenza virus infection, an influenza virus disease or symptom associated therewith; (ii) reduction in the duration of an influenza virus infection, an influenza virus disease or symptom associated therewith; (iii) prevention of the progression of an influenza virus infection, an influenza virus disease or symptom associated therewith; (iv) regression of an influenza virus infection, an influenza virus disease or symptom associated therewith; (v) prevention of the development or onset of an influenza virus infection, an influenza virus disease or symptom associated therewith; (vi) prevention of the recurrence of an influenza virus infection, an influenza virus disease or symptom associated therewith; (vii) reduction or prevention of the spread of an influenza virus from one cell to another cell, one tissue to another tissue, or one organ to another organ; (viii) prevention or reduction of the spread/transmission of an influenza virus from one subject to another subject; (ix) reduction in organ failure associated with an influenza virus infection or influenza virus disease; (x) reduction in the hospitalization of a subject; (xi) reduction in the hospitalization length; (xii) an increase in the survival of a subject with an influenza virus infection or a disease associated therewith; (xiii) elimination of an influenza virus infection or a disease associated therewith; (xiv) inhibition or reduction in influenza virus replication; (xv) inhibition or reduction in the binding or fusion of influenza virus to a host cell(s); (xvi) inhibition or reduction in the entry of an influenza virus into a host cell(s); (xvii) inhibition or reduction of replication of the influenza virus genome; (xviii) inhibition or reduction in the synthesis of influenza virus proteins; (xix) inhibition or reduction in the assembly of influenza virus particles; (xx) inhibition or reduction in the release of influenza virus particles from a host cell(s); (xxi) reduction in influenza virus titer; (xxii) the reduction in the number of symptoms associated with an influenza virus infection or an influenza virus disease (xxiii) enhancement, improvement, supplementation, complementation, or augmentation of the prophylactic or therapeutic effect(s) of another therapy; (xxiv) prevention of the onset or progression of a secondary infection associated with an influenza virus infection; and/or (xxv) prevention of the onset or diminution of disease severity of bacterial pneumonias occurring secondary to influenza virus infections.

As used herein, in some embodiments, the term "wild-type" in the context of a virus refers to the types of viruses that are prevalent, circulating and naturally producing typical outbreaks of disease.

4. BRIEF DESCRIPTION OF THE DRAWINGS

FIG. 1. Generation of recombinant influenza virus carrying NS-green fluorescent protein (GFP). (A) Schematic representation of the NS gene of NS-GFP virus as compared to the wild-type virus. The splice acceptor site in NS was mutated to prevent mRNA splicing. NS1 was fused to GFP via a GSGG (SEQ ID NO:14) linker, followed by PTV-1 2A autoproteolytic cleavage site and NEP open reading frame (ORF). (B) Immunostaining of NP protein. A549 cells were infected with recombinant PR8 virus carrying NS-GFP. At 10 hpi, cells were fixed stained for NP. (C) Fluorescent micrographs NS1-GFP virus plaques taken at 20× magnification.

FIG. 2. In vitro characterization of NS1-GFP virus. (A) Single and multicycle growth kinetics in MDCK cells. (B) Western blot analysis of NS1 and NS1-GFP expression in MDCK cells. (C) Analysis of interferon-β promoter activation by NS1-GFP virus. (D) Comparison of vRNA incorporation levels in NS1-GFP and Wt PR8 viruses.

FIG. 3. In vivo characterization of NS1-GFP virus. (A) Pathogenicity of PR8 and NS1-GFP viruses in mice. Five-week old female Balb/C mice were intranasally inoculated with $10^4$ pfu of PR8 (n=6) or NS1-GFP virus (n=6) or control (n=4). The body weight loss and survival were measured every day and are represented as percentage of Day 0. (B) Viral titers in lungs of mice infected with wild-type PR8 virus and with NS1-GFP virus. (C) Five-week old female Balb/c mice were intranasally inoculated with either PR8 or NS1-GFP virus at the indicated doses. The lungs were excised out on day 4 post-infection and the fluorescence from the infected lungs was imaged using a IVIS-200 imaging system (Xenogen). (D) Fluorescent micrographs of mice lung cryosection taken at a magnification of 10×.

FIG. 4. Dynamics of influenza infection in lungs. (A) Kinetics of epithelial cell infections. Five-week old female Balb/c mice were intranasally inoculated with NS1-GFP virus at the indicated doses and the lung homogenates analyzed for GFP expressing non-immune cells (CD45⁻) using a LSR11 flow cytometer. (B) Comparison kinetics of immune and non-immune cell infection in the mice lungs. Five-week old female Balb/c mice were intranasally inoculated with $10^6$ pfu NS1-GFP virus and analyzed for GFP expression in cells types differentially expressing CD11c and CD11b.

FIG. 5. Oseltamivir treatment restricts infection to localized areas. (A) Ex vivo imaging of mice lungs on day 2 post-infection. Balb/C mice infected with NS1-GFP virus were either left untreated or treated with oseltamivir, daily once with 50 mg/Kg. On day 2 after infection the mice lungs were excised out and imaged using the IVIS-200 system. (B)

Ex vivo imaging of mice lungs on day 4. Oseltamivir treatment was started on day 0 or 2 post infection.

Figures 6A, 6B, 6C, 6D:
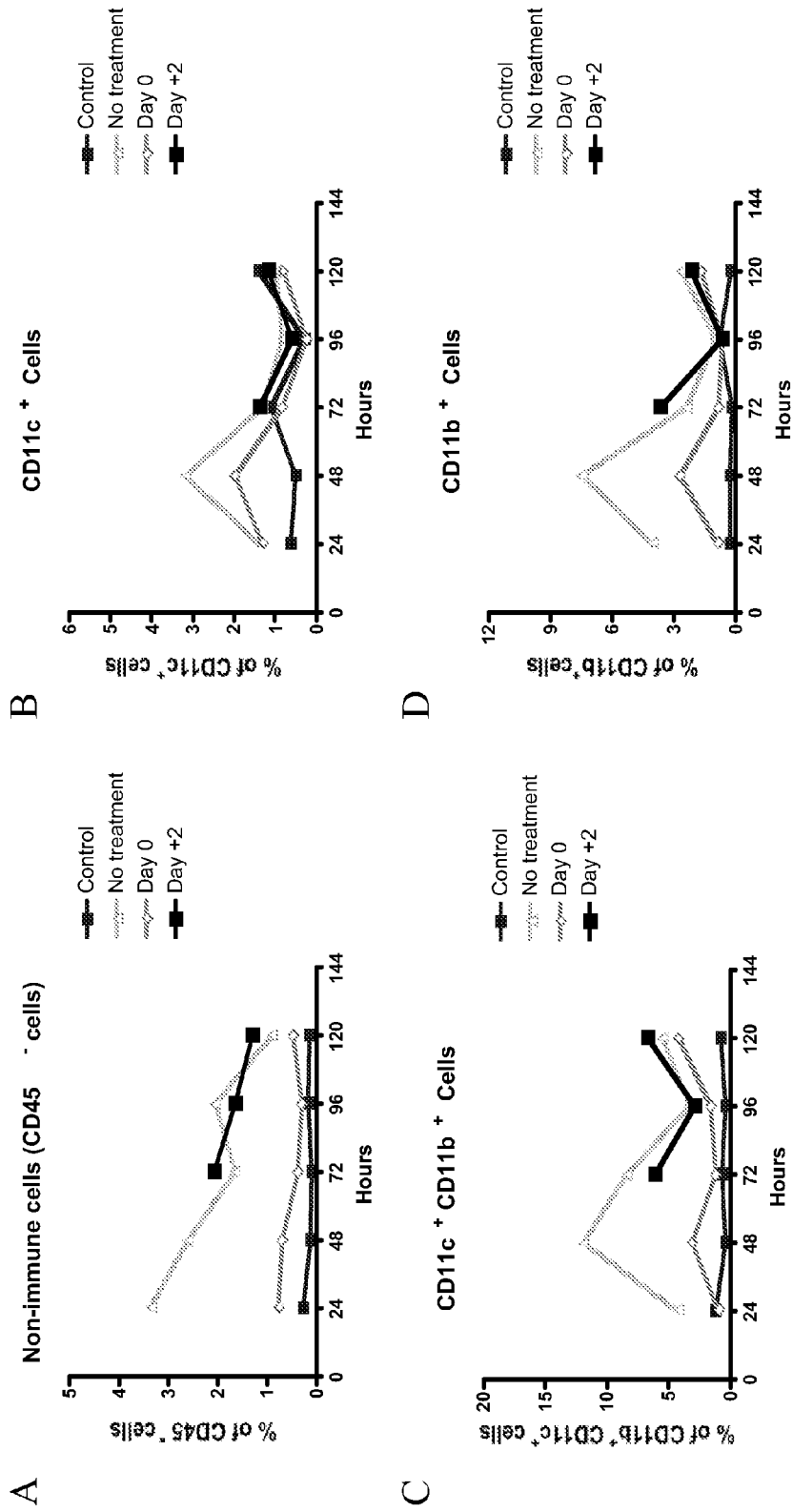
Figures 6E, 6F, 6G:
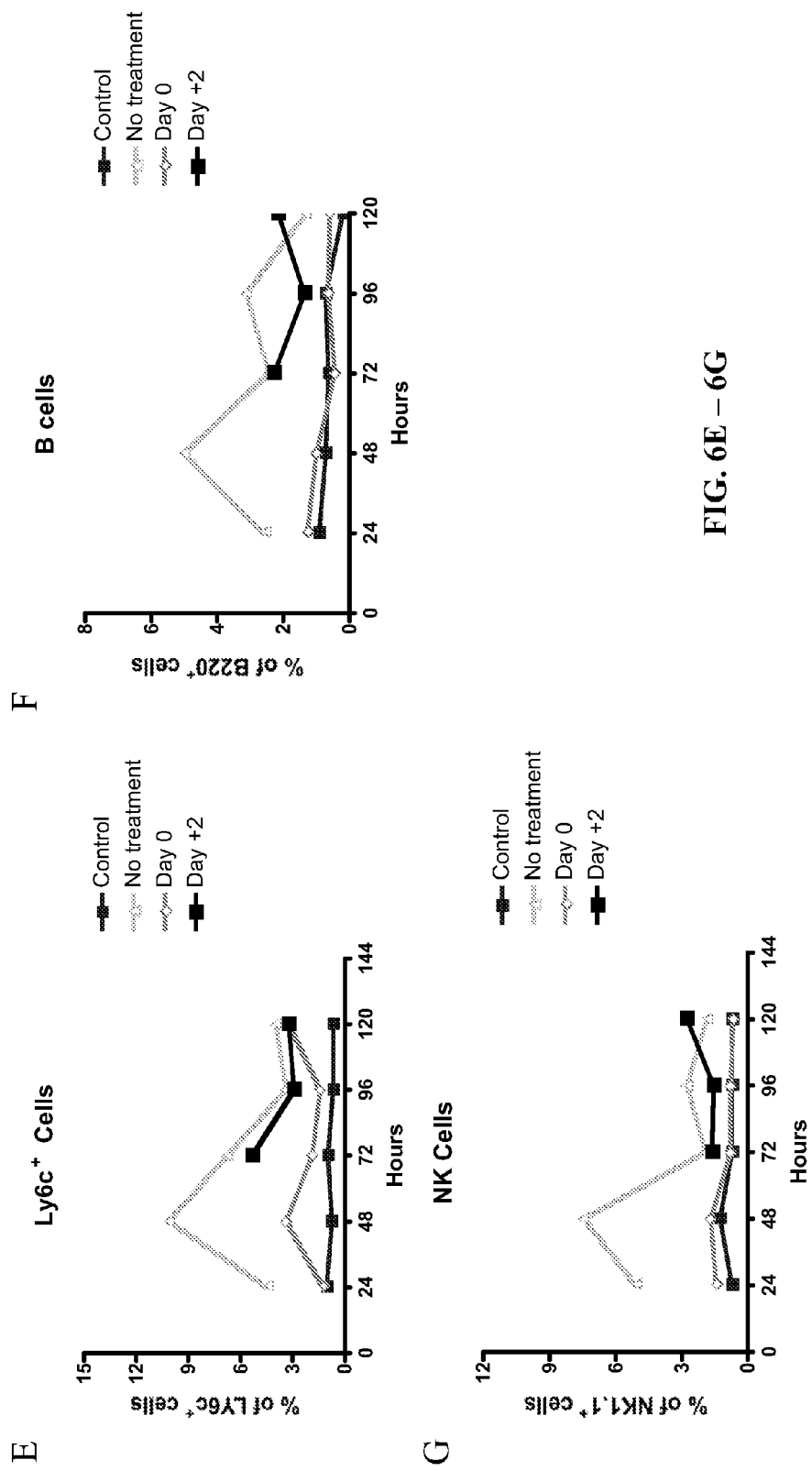

FIG. 6. Oseltamivir treatment significantly reduces the infection of immune and non-immune cells. Mice infected with NS1-GFP virus was either left untreated or treated with oseltamivir starting day 0 or 2 post-infection. The kinetics of infection progression in different cells types were analyzed using a BD LSR II flow cytometer. Panels A-G shows the kinetics of GFP expression in different cell types in treated and untreated groups.

FIG. 7. Generation of recombinant influenza virus carrying a GFP reporter. (A) Schematic representation of the NS segment of Wt PR8 virus and NS1-GFP virus. The splice acceptor site in NS was mutated to prevent mRNA splicing (SD-splice donor site, SA-splice acceptor site). The common regions present in both NS1 (light grey) and NEP (dark grey, labeled) are shown in dark grey (unlabeled). NS1 was fused to GFP (grey, labeled) via a GSGG (SEQ ID NO:14) linker, followed by PTV-1 2A autoproteolytic cleavage site (lightest grey) and the NEP ORF (labeled with flanking dark grey unlabeled rectangle). (B) A549 cells were infected with recombinant PR8 virus carrying NS1-GFP. At 10 hpi, cells were fixed stained for NP. NP staining is shown in red and NS1-GFP is shown in green. (C) Fluorescent micrographs of NS1-GFP virus plaques taken at 20× magnification.

FIG. 8. In vitro characterization of NS1-GFP virus. (A) Single-cycle (MOI=1) and multi-cycle (MOI=0.001) growth kinetics in MDCK cells. (B) Western blot analysis of NS1 and NS1-GFP expression in MDCK cells. (C) Analysis of IFN-β promoter activation by NS1-GFP virus.

FIG. 9. In vivo characterization of NS1-GFP virus. Comparison of pathogenicity of PR8 and NS1-GFP viruses in mice. Five-week old female BALB/c mice were intranasally inoculated with indicated doses of PR8 (n=5 per group) or NS1-GFP virus. The body weight was measured daily and represented as percentage of day 0 weight.

FIG. 10. In vivo characterization of NS1-GFP virus. (A-B) Comparison of survival of PR8 and NS1-GFP virus infected mice. BALB/c mice were intranasally inoculated with indicated doses of PR8 or NS1-GFP virus. The survival was monitored daily. (C) Viral titers in lungs of mice infected with Wt PR8 virus and with NS1-GFP viruses. (D) Mice were intranasally inoculated with either PR8 or NS1-GFP virus at the indicated doses. The lungs were excised on day 4 post-infection and the fluorescence from the infected lungs was imaged using IVIS-200 imaging system (Xenogen). (E) Fluorescent micrographs of mice lung cryosections (10× magnification).

Figure 11:
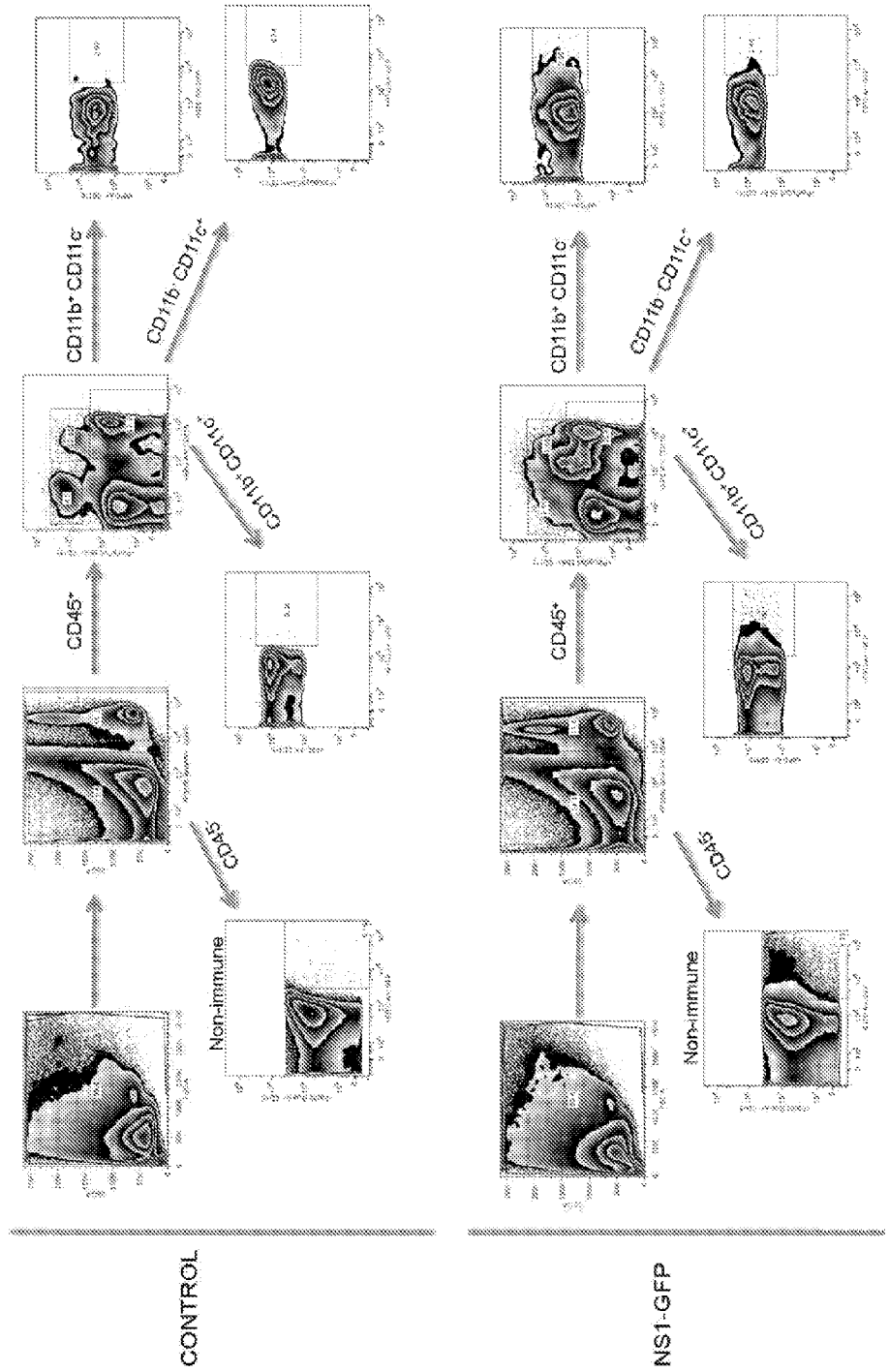

FIG. 11: Analysis of GFP expression in different APC's differentially expressing CD11b and CD11c. Top: Representative analysis of cells from control mice (uninfected). Bottom: Representative analysis of cells from NS1-GFP virus infected mice lungs at 48 hpi.

Figure 12:
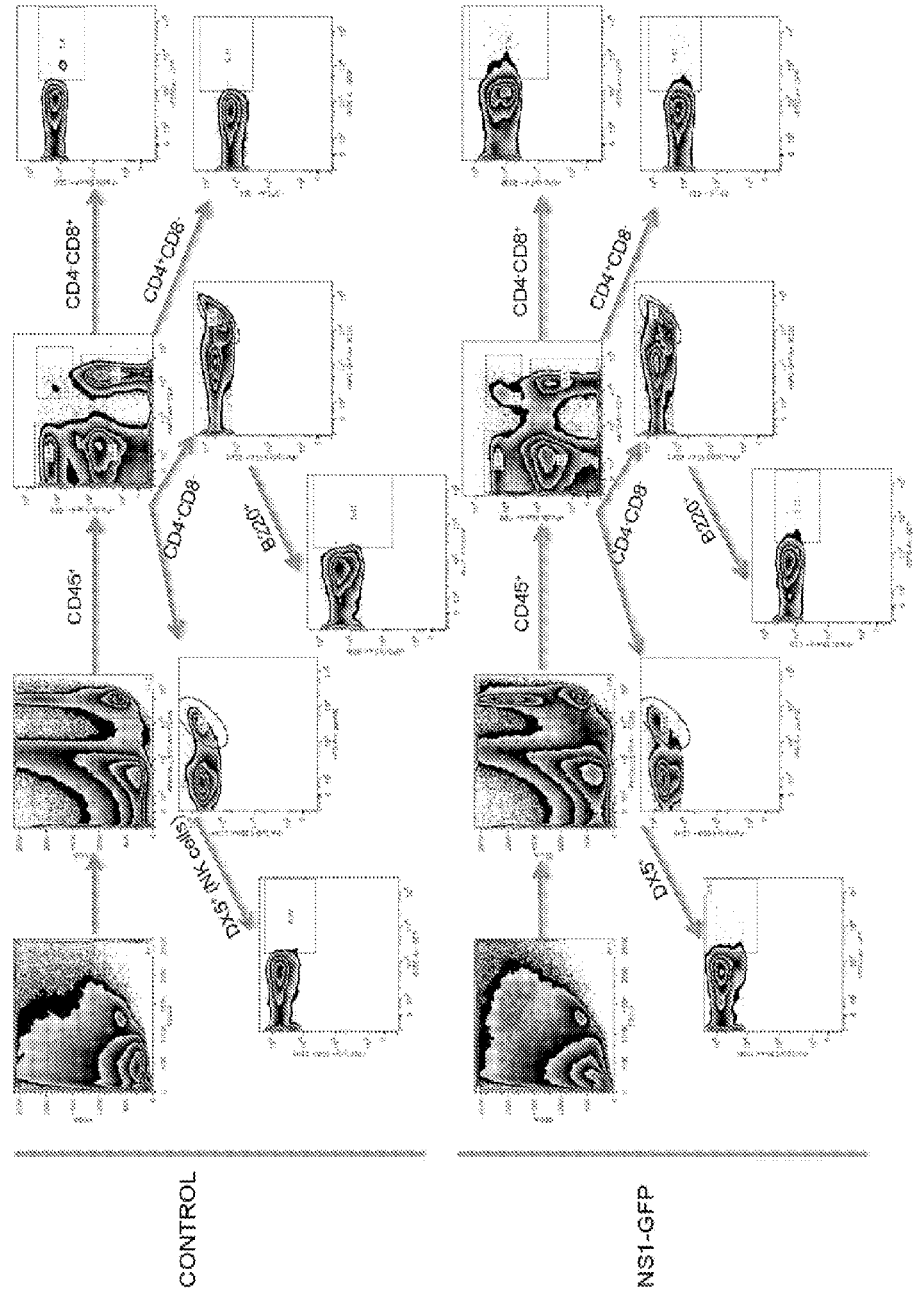

FIG. 12: Analysis of GFP expression in CD4, CD8, B and NK cells based on cellular markers. Top: Representative analysis of cells from control mice (uninfected). Bottom: Representative analysis of cells from NS1-GFP virus infected mice lungs at 48 hpi.

FIG. 13. Dynamics of influenza virus infection in lungs. (A) Kinetics of epithelial cell infection. BALB/c mice were intranasally inoculated with NS1-GFP virus at the indicated doses and the lung homogenates were analyzed for GFP expression in non-hematopoietic cells (CD45$^-$) using a LSR11 flow cytometer. (B) Comparison of the kinetics of hematopoietic and non-hematopoietic cell infection in the lungs. BALB/c mice were intranasally inoculated with $10^6$ pfu NS1-GFP virus and analyzed for GFP expression in cells types differentially expressing CD11c and CD11b. Each data point represents the average from at least 3 mice.

FIG. 14. Oseltamivir and amantadine treatment significantly reduces NS1-GFP virus infection. Mice infected with NS1-GFP virus were either left untreated or treated with oseltamivir (50 mg/Kg) or amantadine (40 mg/Kg), starting 1 hr after infection. The kinetics of infection progression in different cells types were analyzed using a BD LSR II flow cytometer. Panels A-G show the kinetics of GFP expression in different cell types as indicated in treated and untreated groups.

FIG. 15. Oseltamivir treatment restricts influenza virus infection to localized areas. Ex vivo imaging of mice lungs on day 2 (A) and day 4 (B) post-infection. BALB/c mice infected with NS1-GFP virus ($10^6$ pfu) were either left untreated or treated daily once with oseltamivir (50 mg/Kg). The mice lungs were excised at indicated time and imaged using the IVIS-200 system.

FIG. 16. Characterization of in vivo and in vitro stability of NS1-GFP virus. (A) Stability of NS1-GFP virus in vivo. Mice were infected with $10^4$ pfu of NS1-GFP virus and percentage of NS1-GFP carrying viruses in the lung homogenates were analyzed by standard plaque assay followed by scoring for GFP positive or GFP negative plaques. Each data point represents the average from at least 3 mice. (B) Kinetics of NP and GFP expression in CD45$^-$ cells from NS1-GFP virus infected mice. Female BALB/c mice were infected with NS1-GFP virus at a dose of $10^6$ pfu. The levels of NP and GFP expression in CD45$^-$ cells were analyzed using Anti-NP and -GFP specific antibodies in BD-LSR11 flow cytometer. Each data point represents the average from at least 3 mice. (C) Stability of NS1-GFP virus in vitro. MDCK cells were infected with an MOI of 0.001 and supernatant were collected at indicated hpi and scored for levels of GFP positive and GFP negative in the supernatant.

5. DETAILED DESCRIPTION

5.1 Nucleic Acids

In one aspect, provided herein are nucleic acid sequences comprising or consisting of a modified influenza virus NS gene segment (genomic RNA) or the complement thereof (antigenomic RNA).

In specific embodiments, the modified influenza virus gene segments described herein comprise or consist of the following components: (i) an NS1 ORF; (ii) a heterologous nucleotide sequence; (iii) a 2A autoproteolytic cleavage site or another cleavage site; (iv) a NEP ORF; and, optionally, (v) a linker. The presence of the 2A autoproteolytic cleavage site or another cleavage site allows for cleavage of a polyprotein expressed from the modified influenza virus NS gene segment. In some embodiments, either the NS1 splice acceptor site, NS1 splice donor site or both the NS1 splice acceptor and splice donor sites are mutated. The components of the modified influenza virus NS gene segment can be arranged such that the following proteins are produced from the polyprotein encoded by the gene segment: (i) an NS1 protein that is a fusion protein of NS1 and the heterologous nucleotide sequence; and (ii) NEP protein. The components of the modified influenza virus NS gene segment can also be arranged such that the following proteins are produced from the polyprotein encoded by the gene segment: (i) an NS1 protein; (ii) a heterologous protein, and (iii) an NEP protein. The NS1 protein and/or NEP proteins may or may not be full length. In specific embodiments, the NS1 ORF included in the modified influenza virus NS gene segment lacks a stop codon. In some embodiments, either the NS1 ORF splice acceptor site, NS1 splice donor site or both the NS1 splice acceptor and splice donor sites are mutated.

In one embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic site or another cleavage site, and an NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a linker sequence, a 2A autoproteolytic site or another cleavage site, and an NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a linker, a heterologous nucleotide sequence, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a heterologous nucleotide sequence, a 2A autoproteolytic cleavage site or another cleavage site, and an influenza virus NEP ORF.

In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of a heterologous nucleotide sequence, a 2A autoproteolytic cleavage site or another cleavage site, an influenza virus NS1 ORF lacking a stop codon, a 2A autoproteolytic cleavage site or another cleavage site, and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a first heterologous nucleotide sequence, a 2A autoproteolytic cleavage site or another cleavage site, a second heterologous nucleotide sequence, a 2A autoproteolytic cleavage site or another cleavage site and an influenza virus NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In specific embodiments of the foregoing embodiments, the modified influenza NS gene segment does not contain an influenza virus NS1 ORF that encodes an NS1 protein with less than 120, 121, 122, 123, 124, 125, 126, 127, 128, 129, or 130 amino acids. In some specific embodiments, the modified influenza NS gene segment does not contain an NS1 ORF that is truncated at approximately nucleotide 395, 396, 397, 398, 399, 400, 401, 402, 403, 404, 405, 410, 415, or 420, as counted with respect to, e.g., influenza virus PR8. In some embodiments, the modified influenza virus NS gene segment comprises an NS1 ORF that comprises the NS1 splice donor site and/or the splice acceptor site. In some embodiments, a nucleic acid sequence provided herein does not comprise or consist of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a heterologous nucleotide sequence, and an influenza virus NEP ORF. In certain embodiments, a nucleic acid sequence provided herein does not comprise or consist of a modified influenza virus NS gene segment or the complement thereof, wherein the modified influenza virus NS gene segment comprises or consists of a truncated influenza virus NS1 ORF, a 2A autoproteolytic cleavage site or another cleavage site, a heterologous nucleotide sequence and an influenza virus NEP ORF.

In specific embodiments of the foregoing embodiments, the position of the cleavage site to be included in the modified influenza NS segment will be determined based on consideration of the size of the heterologous nucleotide sequence to be included.

In another aspect, provided herein are nucleic acid sequences encoding a nucleotide sequence comprising or consisting of a modified influenza virus NS gene segment (genomic RNA) or the complement thereof (antigenomic RNA). In one embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a 2A autoproteolytic cleavage site or another cleavage site, and an NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a heterologous nucleotide sequence, a linker sequence, a 2A autoproteolytic cleavage site or another cleavage site, and an NEP ORF. In certain embodiments, the modified NS gene segment has one or more mutations in either the splice acceptor site, splice donor site or both the splice acceptor and splice donor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a linker, a heterologous nucleotide sequence, a 2A autoproteolytic cleavage site or another cleavage site, and an influenza virus NEP ORF. In certain embodiments, the modified NS gene segment has one or more mutations in either the splice acceptor site, the splice donor site, or both the splice donor and the splice acceptor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a heterologous nucleotide sequence, a 2A autoproteolytic cleavage site or another cleavage site, and an influenza virus NEP ORF. In certain embodiments, the modified NS gene segment has one or more mutations in either the splice acceptor site, the splice donor site, or both the splice donor and splice acceptor sites that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of heterologous nucleotide sequence, a 2A autoproteolytic cleavage site or another cleavage site, an influenza virus NS1 ORF lacking a stop codon, a 2A autoproteolytic cleavage site or another cleavage site, and an influenza virus NEP ORF. In certain embodiments, the modified NS gene segment has one or more mutations in either the splice acceptor site, the splice donor site, or both the splice acceptor and splice donor sites, that prevents splicing of mRNA. In certain embodiments, the components of the modified influenza virus gene segment are in the order that they are listed in 3' to 5' order.

In another embodiment, provided herein is a nucleic acid sequence encoding a nucleotide sequence comprising or consisting of a modified influenza virus NS gene segment or the complement thereof, wherein the modified influenza virus NS gene segment comprises or consists of an influenza virus NS1 ORF lacking a stop codon, a 2A autoproteolytic cleavage site or another cleavage site, a first heterologous nucleotide sequence, a 2A autoproteolytic cleavage site or another cleavage site, a second heterologous nucleotide sequence, a 2A autoproteolytic cleavage site or another cleavage site and an influenza virus NEP ORF. In certain embodiments, the modified NS gene segment has one or more mutations in either the splice acceptor site, the splice donor site, or both the splice acceptor and splice donor sites that prevents splicing of mRNA. In certain embodiments, the components of the modified influenza virus gene segment are in the order that they are listed in 3' to 5' order.

In specific embodiments of the foregoing embodiments, the modified influenza NS gene segment does not contain an influenza virus NS1 ORF that encodes an NS1 protein with less than 120, 121, 122, 123, 124, 125, 126, 127, 128, 129 or 130 amino acids. In some specific embodiments, the modified influenza virus NS gene segment does not contain an NS1 ORF that is truncated at approximately nucleotide 395, 396, 397, 398, 399, 400, 401, 402, 403, 404, 405, 406, 407, 408, 409 or 410 counted with respect to, e.g., influenza virus A/Puerto Rico 8/34 (PR8). In some embodiments, the modified influenza virus NS gene segment comprises an NS1 ORF that contains the NS1 splice acceptor site and/or splice donor site. In some embodiments, a nucleic acid sequence provided herein does not encode a nucleotide sequence comprising or consisting of a modified influenza virus NS gene segment or the complement thereof, wherein the modified influenza virus NS gene segment comprises or consists of (in 3' to 5' order) an influenza virus NS1 ORF lacking a stop codon, a 2A autoproteolytic cleavage site or another cleavage site, a heterologous nucleotide sequence, and an influenza virus NEP ORF. In certain embodiments, a nucleic acid sequence provided herein does not encode a nucleotide sequence comprising a modified influenza virus NS gene segment, wherein the modified influenza virus gene segment comprises or consists of (in 3' to 5' order) a truncated influenza virus NS1 ORF, a 2A autoproteolytic cleavage site, a heterologous nucleotide sequence, and an influenza virus NEP ORF.

In specific embodiments of the foregoing embodiments, the position of the cleavage site to be included in the modified influenza NS segment will be determined based on consideration of the size of the heterologous nucleotide sequence to be included.

In specific embodiments, the modified influenza virus NS gene segment comprises the signals necessary to package the segment. The packaging signals for the influenza virus NS gene segment are known in the art. In specific embodiments, the NS1 and heterologous nucleotide sequence are expressed as a fusion protein.

In certain embodiments, a nucleic acid sequence that encodes a modified influenza virus NS1 gene segment described herein or the complement thereof comprises a promoter. Specific examples of promoters include an RNA polymerase I promoter, an RNA polymerase II promoter, an RNA polymerase III promoter, a T7 promoter and a T3 promoter. In a specific embodiment, a nucleic acid sequence that encodes a modified influenza virus NS1 gene segment or the complement thereof comprises a human RNA polymerase I promoter. In certain embodiments, a nucleic acid sequence that encodes a modified influenza virus NS1 gene segment described herein or the complement thereof comprises a transcription termination sequence. Specific examples of transcription termination sequences include an RNA polymerase I terminator sequence, an RNA polymerase II terminator sequence, or an RNA polymerase III terminator sequence. In some embodiments, a nucleic acid sequence that encodes a modified influenza virus NS1 gene segment described herein or the complement thereof comprises a ribozyme recognition sequence. In a specific embodiment, a nucleic acid sequence that encodes a modified influenza virus NS1 gene segment described herein or the complement thereof comprises an RNA polymerase I promoter sequence and an RNA polymerase I terminator sequence. In certain embodiments, a nucleic acid sequence that encodes a modified influenza virus NS1 gene segment or the complement thereof comprises an RNA polymerase I promoter, an RNA polymerase I termination sequence, an RNA polymerase II promoter, and a polyadenylation signal.

In certain embodiments, a nucleic acid sequence described herein is part of or incorporated into a vector. In a specific embodiment, a nucleic acid sequence described herein is part of or incorporated into a vector that facilitates the production of a modified influenza virus NS1 gene segment or the complement thereof. In one embodiment, a nucleic acid sequence described herein is part of or incorporated into the pDZ vector (see, e.g., Quinlivan et al., 2005, J. of Virology 79: 8431-8439 for information relating to the pDZ vector). In another embodiment, a nucleic acid sequence described herein is part of or incorporated into the pHW2000 vector (see, e.g., Hoffmann et al., 2000, Proc Natl Acad Sci USA. 97(11):6108-13 for information relating to the pHW2000 vector). In another embodiment, a nucleic acid sequence described herein is part of or incorporated into the pAD3000 vector (see, e.g., Hoffmann et al., 2000, Proc Natl Acad Sci USA. 97(11):6108-13 for information relating to the pAD3000 vector). In another embodiment, a nucleic acid sequence described herein is part of or incorporated into the pAD4000 vector (see, e.g., Wang et al., 2007, J. of Virology 4: 102 for information relating to the pAD4000 vector).

Techniques for the production or use of the nucleic acids will employ, unless otherwise indicated, routine conventional techniques of molecular biology and recombinant DNA manipulation and production. Any cloning technique known to the skilled artisan can be used to assemble the nucleic acids described herein and to mutate nucleotides where necessary. Such techniques are well-known and are available to the skilled artisan in laboratory manuals such as Sambrook and Russell, Molecular Cloning: A Laboratory Manual, 3$^{rd}$ edition, Cold Spring Harbor Laboratory Press, Cold Spring Harbor, N.Y. (2001). In particular, polymerase chain reaction, restriction enzymes, ligase enzyme, mutagenic primers, and amplification of nucleic acid fragments in vectors can be used to generate the individual elements of the nucleic acids described herein and then to assemble them.

In some embodiments, a nucleic acid sequence described herein is introduced (e.g., transfected) into a substrate, such as a host cell or an embryonated egg. Thus, in some embodiments, provided herein is a substrate (e.g., host cells or eggs) comprising a nucleic acid sequence described herein. In other embodiments, a nucleic acid sequence described herein that is part of or incorporated into a vector is introduced (e.g., transfected) into a substrate, such as a host cell or an embryonated egg. Thus, in some embodiments, provided herein is a substrate (e.g., host cells or eggs) comprising a nucleic acid sequence described herein that is part of or incorporated into a vector. Host cells and embryonated eggs are known in the art and examples are provided herein, e.g., in Section 5.4, infra.

5.1.1 Influenza Virus NS Gene Segment

The open reading frames of influenza virus gene segments are known in the art or can readily be determined using standard molecular biology and virology techniques. In particular, influenza virus NS gene segments and the open reading frames of the NS1 and NEP proteins encoded by such segments are known in the art or can readily be determined. For example and not by limitation, the influenza virus A/WSN/33 (WSN) NS gene segment can be found in GenBank (GenBank No. Z21498; GI: 296585). The open reading frame for the WSN NS1 is from nucleotides 27 to 719. The open reading frame for the WSN NS2 is from nucleotides 27 to 56 of exon 1 and nucleotides 529 to 864. The influenza virus A/Puerto Rico/8/34 (PR8) NS gene segment can be found in GenBank (e.g., GenBank No. AF389122.1 GI:21693177). The open reading frame for the PR8 NS1 is from nucleotides 27 to 719. The open reading frame for the PR8 NEP (otherwise known as NS2) is from 27 to 56 of exon 1 and nucleotides 529 to 864. In specific embodiments, either the NS1 ORF, the NEP ORF or both are codon optimized (without changing the protein sequence) to, e.g., avoid repetitive sequences, to increase protein expression and/or to increase the stability of the NS gene segment. Techniques for codon optimization are known in the art.

Any influenza virus NS segment may be modified to produce a modified influenza virus NS gene segment described herein. In one embodiment, the modified influenza virus NS gene segment described herein is derived from an influenza A virus. In another embodiment, the modified influenza virus NS gene segment described herein is derived from an influenza B virus. In another embodiment, the modified influenza virus NS gene segment described herein is derived from an influenza C virus. In certain embodiments, the modified influenza virus NS gene segment is a chimera of two influenza virus types, subtypes or strains. For example, the modified influenza virus NS gene segment may comprise the open reading frame of NS1 from an influenza A virus and the open reading frame of NEP from an influenza B virus. As another example, the modified influenza virus NS gene segment may comprise the open reading frame of NS1 from one influenza A virus strain and the open reading of NEP from a different influenza A virus strain.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/sw/Iowa/15/30 (H1N1); A/WSN/33 (H1N1); A/eq/Prague/1/56 (H7N7); A/PR/8/34; A/mallard/

Potsdam/178-4/83 (H2N2); A/herring gull/DE/712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N1); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren IDT2570/03 (H1N2); A/sw/Gescher/IDT2702/03 (H1N2); A/sw/Haseltinne/2617/03hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Mueslerigen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/swNoglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1); A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos AiresNL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, and strain Rochester/02/2001.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the entire NS1 open reading frame is included in a modified influenza virus NS gene segment described herein. In specific embodiments, the NS1 open reading frame included in a modified influenza virus NS gene segment encodes a full-length influenza virus NS1 protein. In some embodiments, the NS1 open reading frame that is included in a modified influenza virus NS gene segment comprises the NS1 splice acceptor site and/or the NS1 splice donor site. In certain embodiments, a mutated NS1 open reading frame is included in a modified influenza NS virus gene segment described herein. In specific embodiments, the mutated NS1 open reading frame impairs the ability of the virus to antagonize the cellular interferon (IFN) response. Examples of the types of mutations that can be introduced into the open reading frame of influenza virus NS1 include deletions, substitutions, insertions and combinations thereof. One or more mutations can be introduced anywhere throughout the open reading frame of NS1 (e.g., the N-terminus, the C-terminus or somewhere in between) and/or the regulatory elements of the NS1 gene. In one embodiment, a mutation in an influenza virus NS1 open reading frame results in a deletion of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, a mutation in an influenza virus NS1 open reading frame results in an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety. In some embodiments, the mutation in an influenza virus NS1 open reading frame does not result in an NS1 protein of amino acid residues 1-125, wherein the N-terminus amino acid is number 1. In some embodiments, the mutation in an influenza virus NS1 open reading frame does not result in an NS1 protein of amino acid residues 1-124, wherein the N-terminus amino acid is number 1. In some embodiments, the mutation in an influenza virus NS1 open reading frame does not result in a truncated influenza virus NS1 open reading frame of nucleotides 1 to 400 nucleotides. In some embodiments, the mutation in an influenza virus NS1 open reading frame does not result in a truncated influenza virus NS1 open reading frame composed of the first 400 or fewer nucleotides. In some embodiments, the mutation in an influenza virus NS1 open reading frame results in a truncated influenza virus NS1 open reading frame composed of nucleotides 1 to 401 or more.

In a specific embodiment, the NS1 open reading frame included in a modified influenza virus NS gene segment described herein is modified to eliminate the stop codon. Techniques known in the art can be used to eliminate the stop codon of the NS1 open reading frame.

In certain embodiments the entire NEP open reading frame is included in a modified influenza virus NS gene segment described herein. In specific embodiments, the NEP open reading frame included in a modified NS gene segment encodes a full length influenza virus NEP protein. In other embodiments, a mutated NEP open reading frame is included in a modified NS gene segment. The mutated NEP open reading frame may result in a truncated NEP protein.

5.1.2 Mutations in the Splice Acceptor Site

In certain embodiments, when a modified influenza virus NS gene segment comprises the splice acceptor site and the splice donor site, one, two or more mutations are introduced into either the splice acceptor site, the splice donor site, or both the splice acceptor and splice donor sites. With respect to the NS gene segment of influenza virus A/Puerto Rico/8/34, the splice donor site comprises the nucleotide sequence ctttcagG^Tagattg (SEQ ID NO:34), with the cleavage site (indicated by a "^") at nucleotide position 56; and the splice acceptor site comprises the nucleotide sequence caccattgcct-tctcttccA^Ggacatactgctgaggatgtc (SEQ ID NO:35), with the cleavage site (indicated by a "^") at nucleotide position 529. In specific embodiments, a modified influenza virus NS gene segment comprises 1, 2, 3, 4, 5, 6 or more mutations at the either the splice acceptor site, the splice donor site or both splice acceptor and splice donor sites. In a specific embodiment, the mutations in the either the splice acceptor site, the splice donor site, or both the splice acceptor and donor sites of an influenza virus NS gene segment are silent mutations, i.e., mutations that alter the nucleotide sequence of the open reading frame but do not alter the amino acid sequence encoded by the open reading frame. Most naturally occurring amino acids are encoded by multiple different codons (methionine and tryptophan are the exception)—a phenomenon that has been termed degeneracy of the genetic code. Thus, certain mutations of a codon can result in a different nucleotide sequence while encoding the same amino acid.

In certain embodiments, the mutations at the splice acceptor site of an influenza virus NS gene segment result in a conservative amino acid exchange in the protein, i.e., a mutation that results in an amino acid exchange where the new amino acid has very similar chemical properties as the original, wild type amino acid. In certain embodiments, the mutations at the splice donor site of an influenza virus NS gene segment result in a conservative amino acid exchange in the protein. Such conservative amino acid exchanges include amino acid exchanges such as acidic amino acid for acidic amino acid; basic amino acid for basic amino acid; aliphatic amino acid for aliphatic amino acid; and aromatic amino acid for aromatic amino acid.

5.1.3 Heterologous Nucleotide Sequences

Any nucleotide sequence heterologous to either an influenza virus NS ORF, an influenza virus NEP ORF, or both an influenza virus NS ORF and influenza virus NEP ORF may be included in a modified influenza virus NS gene segment described herein. In a specific embodiment, any nucleotide sequence heterologous to an influenza virus NS gene segment may be included in a modified influenza virus NS gene segment described herein. In certain embodiments, the heterologous nucleotide sequence is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous nucleotide sequence is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 10 to 1500 nucleotides in length. In some embodiments, the heterologous nucleotide encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, or 500 or more amino acids in length. In some embodiments, the heterologous nucleotide encodes a polypeptide that does not exceed 500 amino acids in length. In specific embodiments the heterologous nucleotide sequence does not contain a stop codon. In certain embodiments, the heterologous nucleotide sequence is codon-optimized. Techniques for codon optimization are known in the art and can be applied to codon optimize a heterologous nucleotide sequence.

In one embodiment, a heterologous nucleotide sequence encodes an antigen of any infectious pathogen or an antigen associated with any disease that is capable of eliciting an immune response. In a specific embodiment, the antigen is a glycoprotein. In certain embodiments, a heterologous nucleotide sequence encodes a viral antigen. In some embodiments, the viral antigen may be an influenza virus antigen from a different type, subtype or strain of influenza virus than the NS1 and/or NEP open reading frames. For example, in some embodiments, the heterologous nucleotide sequence of the modified influenza virus NS gene segment encodes an influenza virus HA and/or NA antigen of a different type, subtype or strain of influenza virus than the NS1 ORF, NEP ORF or both, and/or the other gene segments. In other embodiments, the viral antigen is an antigen from a virus other than an influenza virus.

Non-limiting examples of viral antigens include antigens from adenoviridae (e.g., mastadenovirus and aviadenovirus), herpesviridae (e.g., herpes simplex virus 1, herpes simplex virus 2, herpes simplex virus 5, herpes simplex virus 6, Epstein-Barr virus, HHV6-HHV8 and cytomegalovirus), leviviridae (e.g., levivirus, enterobacteria phase MS2, allolevirus), poxyiridae (e.g., chordopoxyirinae, parapoxvirus, avipoxvirus, capripoxvirus, leporiipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonovirinae (e.g., pneumovirus, human respiratory synctial virus), human respiratory syncytial virus and metapneumovirus (e.g., avian pneumovirus and human metapneumovirus)), picornaviridae (e.g., enterovirus, rhinovirus, hepatovirus (e.g., human hepatitis A virus), cardiovirus, and apthovirus), reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus (HIV) 1 and HIV-2 (e.g., HIV gp160), spumavirus), flaviviridae (e.g., hepatitis C virus, dengue virus, West Nile virus), hepadnaviridae (e.g., hepatitis B virus), togaviridae (e.g., alphavirus (e.g., sindbis virus) and rubivirus (e.g., rubella virus)), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus). In a specific embodiment the viral antigen, is HIV gp120, gp41, HIV Nef, RSV F glycoprotein, RSV G glycoprotein, HTLV tax, herpes simplex virus glycoprotein (e.g., gB, gC, gD, and gE) or hepatitis B surface antigen, hepatitis C virus E protein or coronavirus spike protein. In one embodiment, the viral antigen is not an HIV antigen. In one embodiment, the viral antigen is not HIV-1 Nef. In one embodiment, the viral antigen is not HIV-1 gp41.

In other embodiments, a heterologous nucleotide sequence encodes a bacterial antigen (e.g., bacterial coat protein). In other embodiments, a heterologous nucleotide sequence encodes parasitic antigen (e.g., a protozoan antigen). In yet other embodiments, a heterologous nucleotide sequence encodes a fungal antigen.

Non-limiting examples of bacterial antigens include antigens from bacteria of the Aquaspirillum family, Azospirillum family, Azotobacteraceae family, Bacteroidaceae family, *Bartonella* species, Bdellovibrio family, *Campylobacter* species, *Chlamydia* species (e.g., *Chlamydia pneumoniae*), *clostridium*, Enterobacteriaceae family (e.g., *Citrobacter* species, *Edwardsiella, Enterobacter aerogenes, Envinia* species, *Escherichia coli, Hafnia* species, *Klebsiella* species, *Morganella* species, *Proteus vulgaris, Providencia, Salmonella* species, *Serratia marcescens*, and *Shigella flexneri*), Gardinella family, *Haemophilus influenzae*, Halobacteriaceae family, Helicobacter family, Legionallaceae family, *Listeria* species, Methylococcaceae family, mycobacteria (e.g., *Mycobacterium tuberculosis*), Neisseriaceae family, Oceanospirillum family, Pasteurellaceae family, *Pneumococcus* species, *Pseudomonas* species, Rhizobiaceae family, Spirillum family, Spirosomaceae family, *Staphylococcus* (e.g., methicillin resistant *Staphylococcus aureus* and *Staphylococcus* pyrogenes), *Streptococcus* (e.g., *Streptococcus enteritidis, Streptococcus fasciae*, and *Streptococcus pneumoniae*), Vampirovibr Helicobacter family, Yersinia family, *Bacillus antracis* and Vampirovibrio family.

Non-limiting examples of parasite antigens include antigens from a parasite such as an amoeba, a malarial parasite, *Plasmodium, Trypanosoma cruzi*. Non-limiting examples of fungal antigens include antigens from fungus of *Absidia* species (e.g., *Absidia corymbifera* and *Absidia ramosa*), *Aspergillus* species, (e.g., *Aspergillus flavus, Aspergillus fumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kern, Candida krusei, Candida parapsilosis, Candida pseudotropicalis, Candida quiller-mondii, Candida rugosa, Candida stellatoidea*, and *Candida tropicalis*), *Coccidioides immitis, Conidiobolus* species, *Cryptococcus neoforms, Cunninghamella* species, *dermatophytes, Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii, zygomycetes*, and classes such as Zygomycetes, Ascomycetes, the Basidiomycetes, Deuteromycetes, and Oomycetes.

In some embodiments, a heterologous nucleotide sequence encodes a respiratory pathogen antigen. In a specific embodiment, the respiratory pathogen is a virus such as RSV, coronavirus, human metapneumovirus, parainfluenza virus, hendra virus, nipah virus, adenovirus, rhinovirus, or PRRSV. Non-limiting examples of respiratory viral antigens include Respiratory Syncytial virus F, G and M2 proteins, Coronavirus (SARS, HuCoV) spike proteins (S), human metapneumovirus fusion proteins, Parainfluenza virus fusion and hemagglutinin proteins (F, HN), Hendra virus (HeV) and Nipah virus (NiV) attachment glycoproteins (G and F), Adenovirus capsid proteins, Rhinovirus proteins, and PRRSV wild type or modified GP5 and M proteins.

In another specific embodiment, the respiratory pathogen is a bacteria such as *Bacillus anthracis, mycobacterium tuberculosis, Bordetella pertussis, streptococcus pneumoniae, yersinia pestis, staphylococcus aureus, Francisella tularensis, legionella pneumophila, chlamydia pneumoniae, pseudomonas aeruginosa, neisseria meningitides*, and *haemophilus influenzae*. Non-limiting examples of respiratory bacterial antigens include *Bacillus anthracis* Protective antigen PA, *Mycobacterium tuberculosis* mycobacterial antigen 85A and heat shock protein (Hsp65), *Bordetella pertussis* pertussis toxoid (PT) and filamentous hemagglutinin (FHA), *Streptococcus pneumoniae* sortase A and surface adhesin A (PsaA), *Yersinia pestis* F1 and V subunits, and proteins from *Staphylococcus aureus, Francisella tularensis, Legionella pneumophila, Chlamydia pneumoniae, Pseudomonas aeruginosa, Neisseria meningitides*, and *Haemophilus influenzae*.

In some embodiments, a heterologous nucleotide sequence encodes a T-cell epitope.

In some embodiments, a heterologous nucleotide sequence encodes a tumor antigen or tumor associated antigen. In some embodiments, a heterologous nucleotide sequence encodes a cytokine or growth factor. In certain embodiments, a heterologous nucleotide sequence encodes a peptide tag, such as flag tag. In some embodiments, a heterologous nucleotide sequence encodes a detectable substance.

Non-limiting examples of tumor associated antigens include MAGE-1, MAGE-3, BAGE, GAGE-1, GAGE-2, N-acetylglucosaminyltransferase-V, p-15, MART-1/MelanA, TRP-1 (gp75), Tyrosinase, cyclin-dependent kinase 4, MUM-1, CDK4, HER-2/neu, human papillomavirus-E6, human papillomavirus E7, MUC-1, caspase-8, CD5, CD20, CEA, mucin-1, LewisX, CA-125, epidermal growth factor receptor, p185HER2, IL-2R, tenascin, antigens associated with a metalloproteinase, and CAMPATH-1. Non-limiting examples of cytokines and growth factors include interleukin (IL)-2, IL-4, IL-5, IL-6, IL-7, IL-9, IL-10, IL-12, IL-15, IL-18, IL-22, IFN-alpha, IFN-beta, and IFN-beta. Non-limiting examples of detectable substances include various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; and bioluminescent materials, such as but not limited to, luciferase, luciferin, green fluorescent protein (GFP), red fluorescent protein (RFP) and aequorin. In one embodiment, the detectable substance is not GFP.

5.1.4 Linkers

In certain embodiments, a modified influenza virus NS gene segment comprises a linker sequence. In some embodiments, a modified influenza virus NS segment comprises a linker sequence between the heterologous nucleotide sequence and the 2A autoproteolytic site or other cleavage site. In some embodiments, linker sequence is in front of the 2A autoproteolytic site or other cleavage site. In some embodiments, the linker sequence is between the influenza virus NS1 ORF (with or without a stop codon) and the heterologous nucleotide sequence. In certain embodiments, a linker sequence is between the 2A autoproteolytic cleavage site or other cleavage site and the NEP ORF. In some embodiments, a modified influenza virus NS gene described herein comprises 2, 3 or more linkers. For example, a first linker may be present between the NS1 ORF and a heterologous nucleotide sequence, and a second linker may be present between a 2A autoproteolytic cleavage site or other cleavage site and the NEP ORF. In certain embodiments, the 2, 3 or more linkers are different from each other. In other embodiments, the 2, 3 or more linkers are identical to each other. In specific embodiments, the linker encodes a polypeptide linker. In one embodiment, the polypeptide linker comprises a plurality of glycine, alanine and/or serine residues. It is further preferred that said polypeptide linker comprises a plurality of consecutive copies of an amino acid sequence. Usually, the polypeptide linker comprises 1 to 15 amino acids although polypeptide linkers of more than 15 amino acids may work as well. In certain embodiments, the linker comprises or consists of a length of at least 3 residues, at least 5 residues, at least 10 residues, at least 15 residues, at least 20 residues, at least 25 residues, at least 30 residues or more. In other embodiments, the linker comprises or consists of a length of between 2-4 residues, between 2-4 residues, between 2-6 residues, between 2-8 residues, between 2-10 residues, between 2-12 residues, between 2-14 residues, between 2-16 residues, between 2-18 residues, between 2-20 residues, between 2-22 residues, between 2-24 residues, between 2-26 residues, between 2-28 residues, or between 2-30 residues.

In a specific embodiment, the linker is a glycine, serine, glycine (GSG) (SEQ ID NO:1) linker. In another embodiment, the linker is a glycine, serine, glycine, glycine, glycine, serine and glycine (GSGGGSG) (SEQ ID NO:2). In another embodiment, the linker is glycine, serine, glycine, glycine, glycine, glycine (GSGGGG) (SEQ ID NO:3). In another embodiment, the linker comprises three GSGGGG sequences (GSGGGG$_3$) (SEQ ID NO:4). In another embodiment, the linker is glycine, glycine, glycine, glycine (GGGG) (SEQ ID NO:5), or is GGGG$_2$ (SEQ ID NO:6). In another embodiment, the linker is (GGGGS)$_3$ (SEQ ID NO:7) or (GGGGS)$_4$ (SEQ ID NO:8). In another embodiment, the linker is glutamic acid, alanine, alanine, lysine (EAAK) (SEQ ID NO:9). In some embodiments, the linker comprises or consists of 2, 3, 4, or 5 EAAK sequences ((EAAK)$_2$, (EAAK)$_3$, (EAAK)$_4$, or (EAAK)$_5$) (SEQ ID NOs:10, 11, 12, or 13, respectively).

5.1.5 2A Autoproteolytic Cleavage Site and Other Cleavage Sites

Any autocleaving cleavage site or a protease cleavage site that is recognized by a protease present in cells that are infected with virus may be included in a modified influenza virus NS gene segment described herein. For example, any 2A autoproteolytic cleavage site may be included in a modified influenza virus NS gene segment described herein. In one embodiment, the 2A autoproteolytic cleavage site from FDMV is included in a modified influenza virus NS gene segment. In another embodiment, the 2A autoproteolytic cleavage site from porcine teschovirus-1 is included in a modified influenza virus NS gene segment. In a specific embodiment, a 19 amino acid 2A autoproteolytic cleavage site (one letter amino acid code, ATNFSLLKQAGDVEENPG↓P (SEQ ID NO:20)) is included in a modified influenza virus NS gene segment. In another embodiment, a 2A autoproteolytic cleavage site found in anaphthovirus or cardiovirus is included in a modified influenza virus NS gene segment. In another embodiment, a 2A autoproteolytic site found in cardioviruses encephalomyocarditis virus (EMCV) or Theiler's murine encephalitis virus (TMEV) is included in a modified influenza virus NS gene segment. In another embodiment, a 2A-like sequence with the motif DxExNPG (cleavage) P (SEQ ID NO:36) is included in a modified influenza virus NS gene segment. Other examples of 2A autoproteolytic sequences that may be included in a modified influenza virus NS gene segment may be found, e.g., in Donnelly et al., 2001, J. of General Virology 82: 1027-1041, which is incorporated herein by reference in its entirety.

In a specific embodiment of a modified influenza virus NS segment based on influenza A/Puerto Rico/8/34 comprising and NS1 open reading frame with a mutated splice acceptor site, a 4 amino acid linker (e.g., GSGG) (SEQ ID NO:14), green fluorescent protein, a PTV-1 2A autoproteolytic cleavage site, followed by the NEP open reading frame, the cleavage site is located between nucleotides 1454 and 1455 (single letter nucleotide code: aagaaaacccgggc↓ccgatggatccaaacactgtgtca) (SEQ ID NO:15), which corresponds to between amino acids 476 and 477 of the NS1 protein (single letter amino acid code: IAFAGSGATNFSLLKQAGDVEENPG↓PMDPNTVS-SFQDILLR) (SEQ ID NO:16).

In one embodiment, a cleavage site that may be included in a modified influenza virus NS segment described herein is the foot and mouth disease virus P2A cleavage site NFDLLKLAGDVESNPG/P (SEQ ID NO:25) (SEQ ID NO: 2 in U.S. Pat. No. 6,800,288, issued Oct. 5, 2004). In one embodiment, a cleavage site to be included in a modified influenza virus NS segment described herein is not the foot and mouth disease virus P2A cleavage site NFDLLKLAGD-VESNPG/P (SEQ ID NO:25) (SEQ ID NO: 2 in U.S. Pat. No. 6,800,288, issued Oct. 5, 2004).

In some embodiments, the cleavage site that may be included in a modified influenza virus NS gene segment described herein is a self-cleaving 2A-like sequence. Non-limiting examples of proteins containing cleavage sequences that may be included in a modified influenza virus NS gene segment described herein, and the identity of the sequences with cleavage sites indicated, are provided in the following Table.

| Source | Sequence (cleavage site marked by an arrow) |
|---|---|
| Foot-and-mouth disease virus FDMV 2A | QLLNFDLLKLAGDVESNPG↓P (SEQ ID NO: 17) |
| Cardioviruses encephalomyocarditis virus EMCV | HYAGYFADLLIHDIETNPG↓P (SEQ ID NO: 18) |
| Equine rhinitis A virus ERAV | QCTNYALLKLAGDVESNPG↓P (SEQ ID NO: 19) |
| Porcine teschovirus PTV-1 | ATNFSLLKQAGDVEENPG↓P (SEQ ID NO: 20) |
| Drosophila C virus DrosC | AARQMLLLLSGDVETNPG↓P (SEQ ID NO: 21) |
| Thosea asigna virus TaV | RAEGRGSLLTCGDVEENPG↓P (SEQ ID NO: 22) |
| Infectious flacherie virus IFV | TRAEIEDELIRAGIESNPG↓P (SEQ ID NO: 23) |
| Trypanosoma cruzi AP endonuclease-like sequence | CDAQRQKLLLSGDIEQNPG↓P (SEQ ID NO: 24) |

See, Donnelly et al., 2001, "The 'cleavage' activities of foot-and-mouth disease virus 2A site-directed mutants and naturally occurring '2A-like' sequences," *J Gen Virol* 82: 1027-41.

In some embodiments, the cleavage site is recognized by a cellular protease, such as, but not limited to, a caspase cleavage site, ubiquitin protease cleavage site, or ubiquitin-like protease cleavage site. Non-limiting examples of caspase cleavage sites that may be included in a modified influenza virus NS gene segment described herein include (denoted by one-letter amino acid codes) DEVD (SEQ ID NO:26), DDVD (SEQ ID NO:27), MELD (SEQ ID NO:28), AEVD (SEQ ID NO:29), YVHD (SEQ ID NO:30), DEED (SEQ ID NO:31), and ESVD (SEQ ID NO:32) and similar sequences. See Fischer et al., 2003, "Many cuts to ruin: a comprehensive update of caspase substrates," *Cell Death and Differentiation* 10:76-100. An exemplary ubiquitin-like protease cleavage site that may be included in a modified influenza virus NS gene segment described herein comprises leucine arginine (cleavage location) glycine glycine (-LR↓GG-) (SEQ ID NO:33).

5.2 Recombinant Influenza Virus

In one aspect, provided herein are recombinant influenza viruses comprising a modified influenza virus NS gene segments described herein. In accordance with such an aspect, such a virus further comprises gene segments to complete the full set of gene segments found in a genome of an influenza virus (i.e., complementing influenza virus gene segments). In certain embodiments, the complementing influenza virus gene segments may all be derived from the same type or subtype of an influenza virus. In other embodiments, the complementing influenza virus gene segments may be derived from one, two or more different types or subtypes of an influenza virus. In some embodiments, the complementing influenza virus gene segments may all be derived from the same strain of an influenza virus. In other embodiments, the complementing influenza virus gene segments may be derived from one, two or more different strains of an influenza virus. In certain embodiments, the complementing influenza virus gene segments can be derived from an attenuated influenza virus strain.

In certain embodiments, the modified influenza virus NS gene segment and one, two or more of the complementing influenza virus gene segments may be derived from the same type or subtype of an influenza virus. In other embodiments, the modified influenza virus NS gene segment and one, two or more of the complementing influenza virus gene segments may be derived from different types or subtypes of an influenza virus. In some embodiments, the modified influenza virus NS gene segment and one, two or more of the complementing influenza virus gene segments may be derived from the same strain of an influenza virus. In other embodiments, the modified influenza virus NS gene segment and one, two or more of the complementing influenza virus gene segments may be derived from different strains of an influenza virus.

In certain embodiments, a recombinant influenza virus described herein comprises at least one complementing influenza virus gene segment that encodes a fusion protein. A fusion protein can be a fusion of an influenza virus protein or a fragment thereof with a heterologous protein (such as a viral antigen, a bacterial antigen, a parasitic antigen, a fungal antigen, a tumor antigen, a tumor associated antigen, a cytokine, a growth factor, a peptide tag, or a detectable substance (see Section 5.1.3 for examples of such antigens, cytokines, growth factors, peptide tags, and detectable substances)).

In certain embodiments, a recombinant influenza virus described herein comprises at least one complementing influenza virus gene segment that encodes a bicistronic mRNA. Techniques for creating an influenza virus gene segment that encodes a bicistronic mRNA are known in the art. Bicistronic techniques allow the engineering of coding sequences of multiple proteins into a single mRNA through the use of internal ribosome entry site (IRES) sequences. Briefly, a coding region of one protein is inserted into the open reading frame of a second protein. The insertion is flanked by an IRES and any untranslated signal sequences necessary for proper expression and/or function. The insertion must not disrupt the open reading frame, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. No. 6,887,699, U.S. Pat. No. 6,001,634, U.S. Pat. No. 5,854,037 and U.S. Pat. No. 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). One of the open reading frames of the bicistronic mRNA may encode an influenza virus protein or a fragment thereof and the other open reading frame of the bicistronic mRNA may encode a heterologous protein (such as a viral antigen, a bacterial antigen, a parasitic antigen, a fungal antigen, a tumor antigen, a tumor associated antigen, a cytokine, a growth factor, a peptide tag, or a detectable substance (see Section 5.1.3 for examples of such antigens, cytokines, growth factors, peptide tags, and detectable substances).

In specific embodiments, a recombinant influenza virus described herein is attenuated. In a particular embodiment, the recombinant influenza virus is attenuated such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response.

In some embodiments, a recombinant influenza virus described herein comprises one or more attenuating mutations in a modified influenza virus NS gene segment. In some embodiments, a recombinant influenza virus described herein comprises one or more attenuating mutations in a complementing influenza virus gene segment. In certain embodiments, a recombinant influenza virus described herein comprises one or more attenuating mutations in two, three or more complementing influenza virus gene segments. In some embodiments, a recombinant influenza virus described herein comprises one or more attenuating mutations in a modified influenza virus NS gene segment and one or more attenuating mutations in a complementing influenza virus gene segment.

In certain embodiments, the one or more attenuating mutations may be in the open reading frame of a gene segment encoding one or more of the following: NS1, NP, HA, NA, PB1, PB2 and/or PA. In a specific embodiment, the one or more attenuating mutations may be in the open reading frame of an HA gene segment. In another specific embodiment, the one or more attenuating mutations may be in the open reading of an NP gene segment. In another embodiment, the one or more attenuating mutations may be in the open reading frame of an PB1 gene segment In another embodiment, the one or more attenuating mutations may be in the open reading frame of an PB2 gene segment. In certain embodiments, the one or more attenuating mutations in a gene segment of an influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). In a specific embodiment, one or more temperature sensitive mutations that are attenuating may be introduced in an open reading frame of a gene segment. In some embodiments, the one or more temperature sensitive mutations include one or more of the following: PB1 (K391E, E581G, A661T), PB2 (N265S), and NP (D34G).

In some embodiments, an attenuated recombinant influenza virus expresses the following NP, PB1 and PB2 proteins encoded by cold adapted vaccine master strain A/Ann Arbor/6/60 (see, e.g., Jin et al., 2003, Virology 306: 18-24 for a description of the virus). In some embodiments, an attenuated recombinant influenza virus expresses a mutated M2 protein such as described by Watanabe et al., 2008, J. Virol. 82(5): 2486-2492.

In a specific embodiment, an attenuated recombinant influenza virus comprises a complementing influenza virus gene segment encoding an HA from a pandemic or seasonal influenza virus and a second complementing influenza virus gene segment encoding a viral polymerase subunit (i.e., e.g., PA, PB1 or PB2) with one or more attenuating mutations.

In another aspect, a recombinant influenza virus described herein has a genomic segment "rewired" with one or more other viral genomic segments to prevent reassortment-mediated loss of the chosen segment (see, Gao & Palese 2009, PNAS 106:15891-15896).

5.3 Construction of Recombinant Influenza Virus

Techniques known to one skilled in the art may be used to produce a recombinant influenza virus containing a modified influenza virus NS gene segment described herein. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce a recombinant influenza virus containing a modified influenza virus gene segment. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

In specific embodiments, a nucleic acid sequences encoding a modified influenza virus NS gene segment or the complement thereof is transfected into a host cell that provides the remainder of the gene segments found in an influenza virus genome and expresses the proteins necessary for production of viral particles. Techniques known in the art can be used to isolate/purify the recombinant influenza virus that results (see, e.g., Section 5.4, infra for techniques for isolation/purification of influenza virus).

5.4 Propagation of Recombinant Influenza Virus

The recombinant influenza viruses described herein can be propagated in any substrate that allows the virus to grow to titers that permit the uses of the viruses described herein. In one embodiment, the substrate allows the recombinant influenza viruses described herein to grow to titers comparable to those determined for the corresponding wild-type viruses.

The recombinant influenza virus described herein may be grown in host cells (e.g., avian cells, chicken cells, etc.) that are susceptible to infection by the viruses, embryonated eggs or animals (e.g., birds). Specific examples of host cells include Vero cells, MDCK cells, MBCK cells, COS cells, 293 cells, 293T cells, A549 cells, MDBK cells, etc. Such methods are well-known to those skilled in the art. In a specific embodiment, the recombinant influenza viruses described herein may be propagated in cell lines. In another embodiment, the recombinant influenza viruses described herein are propagated in chicken cells or embryonated eggs. Representative chicken cells include, but are not limited to, chicken embryo fibroblasts and chicken embryo kidney cells.

The recombinant influenza viruses described herein may be propagated in embryonated eggs, e.g., from 6 to 14 days old, 6 to 9 days old, or 10 to 12 days old. Young or immature embryonated eggs can be used to propagate the recombinant influenza viruses described herein. Immature embryonated eggs encompass eggs which are less than ten day old eggs, e.g., eggs 6 to 9 days that are interferon (IFN)-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. In one embodiment, the recombinant influenza viruses may be propagated in 10 day old embryonated eggs. The recombinant influenza viruses described herein can be propagated in different locations of the embryonated egg, e.g., the allantoic cavity. In a specific embodiment, the embryonated egg is an embryonated chicken egg. For a detailed discussion on the growth and propagation viruses, see, e.g., U.S. Pat. No. 6,852,522 and U.S. Pat. No. 6,852,522, both of which are hereby incorporated by reference in their entireties.

For virus isolation, the recombinant influenza viruses described herein can be removed from cell culture and separated from cellular components, typically by well known clarification procedures, e.g., such as gradient centrifugation and column chromatography, and may be further purified as desired using procedures well known to those skilled in the art, e.g., plaque assays.

5.5 Compositions & Routes of Administration

The recombinant influenza viruses described herein may be incorporated into compositions. In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing and/or treating an influenza virus infection. The compositions may also be used in methods or preventing and/or treating influenza virus disease. The composition may be used in methods of eliciting an immune response to a particular antigen(s) or in methods of delivering a certain protein to a subject.

In one embodiment, a pharmaceutical composition comprises a recombinant influenza virus in an admixture with a pharmaceutically acceptable carrier. In some embodiments, a pharmaceutical composition may comprise one or more other therapies in addition to a recombinant influenza virus. In specific embodiments, a recombinant influenza virus described herein that is incorporated into a pharmaceutical composition (e.g., an immunogenic composition such as a vaccine) is a live virus. An immunogenic composition comprising a live recombinant influenza virus for administration to a subject may be preferred because multiplication of the virus in the subject may lead to a prolonged stimulus of similar kind and magnitude to that occurring in natural infections, and therefore, confer substantial, long lasting immunity.

In some embodiments, a recombinant influenza virus described herein that is incorporated into a pharmaceutical composition (e.g., an immunogenic composition such as a vaccine) is inactivated. Techniques known to one of skill in the art may be used to inactivate recombinant influenza viruses described herein. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In specific embodiments, immunogenic compositions described herein are monovalent formulations. In other embodiments, immunogenic compositions described herein are multivalent formulations. In one example, a multivalent formulation comprises one or more recombinant influenza viruses that expresses antigens from an influenza A virus and one or more recombinant influenza viruses that expresses antigens from an influenza B virus.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. Liposomes or micelles can also be used as pharmaceutically acceptable carriers. These can be prepared according to methods known to those skilled in the art, for example, as described in U.S. Pat. No. 4,522,811.

In a specific embodiment, pharmaceutical compositions are formulated to be suitable for the intended route of administration to a subject. For example, the pharmaceutical composition may be formulated to be suitable for parenteral, oral, intradermal, intranasal, transdermal, pulmonary, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, the compositions described herein comprise, or are administered in combination with, an adjuvant. The adjuvant for administration in combination with a composition described herein may be administered before, concomitantly with, or after administration of the composition. In specific embodiments, an inactivated virus immunogenic composition described herein comprises one or more adjuvants. In some embodiments, the term "adjuvant" refers to a compound that when administered in conjunction with or as part of a composition described herein augments, enhances and/or boosts the immune response to a recombinant influenza virus, but when the compound is administered alone does not generate an immune response to the virus. In some embodiments, the adjuvant generates an immune response to a recombinant influenza virus and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211) and QS21 (see Kensil et al., in Vaccine Design: The Subunit and Adjuvant Approach (eds. Powell & Newman, Plenum Press, NY, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine.

The pharmaceutical compositions described herein can be included in a container, pack, or dispenser together with instructions for administration.

5.5.1 Immunogenic Compositions Comprising Live Viruses

In one embodiment, provided herein are immunogenic compositions (e.g., vaccines) comprising one or more live recombinant influenza viruses comprising a modified influenza virus NS segment described herein. In some embodiments, the live virus is attenuated. In some embodiments, an immunogenic composition comprises two, three, four or more live viruses.

In certain embodiments, provided herein are immunogenic compositions (e.g., vaccines) comprising about $10^5$ to about $10^{10}$ fluorescent focus units (FFU) of live attenuated recombinant influenza virus described herein, about 0.1 to about 0.5 mg monosodium glutamate, about 1.0 to about 5.0 mg hydrolyzed porcine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 µg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated recombinant influenza virus described herein, 0.188 mg monosodium glutamate, 2.0 mg hydrolyzed porcine gelatin, 2.42 mg arginine, 13.68 mg sucrose, 2.26 mg dibasic potassium phosphate, 0.96 mg monobasic potassium phosphate, and <0.015 µg/ml gentamicin sulfate per dose. In some embodiments, the immunogenic compositions (e.g., vaccines) are packaged as pre-filled sprayers containing single 0.2 ml doses.

In a specific embodiment, the live virus is propagated in embryonated chicken eggs before its use in an immunogenic composition described herein. In another specific embodiment, the live virus is not propagated in embryonated chicken eggs before its use in an immunogenic composition described herein. In another specific embodiment, the live virus is propagated in mammalian cells, e.g., immortalized human cells (see, e.g., International Application No. PCT/EP2006/067566 published as International Publication No. WO 07/045,674 which is herein incorporated by reference in its entirety) or canine kidney cells such as MDCK cells (see, e.g., International Application No. PCT/IB2007/003536 published as International Publication No. WO 08/032,219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and, therefore, confer substantial, long lasting immunity.

5.6 Generation of Antibodies

The recombinant influenza viruses described herein may be used to elicit neutralizing antibodies against influenza virus or a heterologous nucleotide sequence. In a specific embodiment, a recombinant influenza virus described herein or a composition thereof may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

In certain embodiments, the non-human subjects administered a recombinant influenza virus described herein or an immunogenic composition thereof in accordance with the methods described herein are transgenic animals (e.g., transgenic mice) that are capable of producing human antibodies. Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, *Int. Rev. Immunol.* 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. Companies such as Abgenix, Inc. (Freemont, Calif.), Genpharm (San Jose, Calif.), and Medarex, Inc. (Princeton, N.J.) can be engaged to provide human antibodies directed against a selected antigen.

Alternatively, a recombinant influenza virus described herein may be used to screen for antibodies from antibody libraries. For example, a recombinant influenza virus may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to a recombinant influenza virus described herein. Any screening assay, such as a panning assay, ELISA, surface plasmon resonance, or other antibody screening assay known in the art may be used to screen for antibodies that bind to a recombinant influenza virus. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies elicited or identified in accordance with the methods described herein may be tested for specificity for influenza virus antigens and the ability to neutralize influenza virus using the biological assays known in the art or described herein. In one embodiment, an antibody identified or isolated from a non-human animal antibody specifically binds to an influenza virus antigen. In another embodiment, an antibody identified or isolated from a non-human animal specifically binds to an influenza virus antigen expressed by two or more types, subtypes or strains of influenza virus. In one embodiment, an antibody identified or isolated from a non-human animal neutralizes one, two or more influenza virus types, subtypes or strains. In some embodiments, an antibody elicited or identified using a recombinant influenza virus described herein neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more strains or subtypes of influenza A viruses. In another embodiment, the neutralizing antibody neutralizes one or more strains of influenza B viruses. In another embodiment, the neutralizing antibody neutralizes one or more strains of influenza A virus and one or more strains of influenza B viruses.

Antibodies elicited or identified in accordance with the methods described herein may be tested for specificity to, and the ability to neutralize, a peptide or polypeptide antigen encoded by a heterologous nucleotide sequence described herein using the biological assays known in the art or described herein. In one embodiment, an antibody identified or isolated from a non-human animal antibody specifically binds to a peptide or polypeptide antigen encoded by a heterologous nucleotide sequence described herein. In one embodiment, the neutralizing antibody neutralizes the viral, bacterial, fungal or other pathogen, or a tumor (e.g., described in Section 5.1.3) that expresses the peptide or polypeptide antigen encoded by a heterologous nucleotide sequence described herein.

Antibodies elicited or identified using a recombinant influenza virus described herein include immunoglobulin molecules and immunologically active portions of immunoglobulin molecules, i.e., molecules that contain an antigen binding site that specifically binds to a hemagglutinin polypeptide. The immunoglobulin molecules may be of any type (e.g., IgG, IgE, IgM, IgD, IgA and IgY), class (e.g., IgG1, IgG2, IgG3, IgG4, IgA1 and IgA2) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a recombinant influenza virus described herein may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize influenza virus and the specificity of the antibodies for influenza virus antigens may be tested prior to using the antibodies in passive immunotherapy. See Section 5.7, infra for a discussion regarding use of neutralizing antibodies for the prevention and/or treatment of an influenza virus infection and the disease caused by an influenza virus infection.

The antibodies elicited or identified using a recombinant influenza virus described herein may be incorporated into compositions. In a specific embodiment, the compositions are pharmaceutical compositions. In some embodiments, a pharmaceutical composition may comprise one or more other therapies in addition to an antibody. The pharmaceutical compositions provided herein can be in any form that allows for the composition to be administered to a subject. In a specific embodiment, the pharmaceutical compositions are suitable for veterinary and/or human administration. In another specific embodiment, the antibody compositions are formulated for the intended route of administration (e.g., parenteral, intranasal, or pulmonary administration). The antibody compositions may be used in methods of preventing and/or treating an influenza virus infection. The antibody compositions may also be used in methods or preventing and/or treating influenza virus disease.

Antibodies elicited or identified using a recombinant influenza virus described herein may be used to monitor the efficacy of a therapy and/or disease progression. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few.

Antibodies elicited or identified using a recombinant influenza virus described herein may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann Immunol. (Paris) 125c:373; Jerne et al., 1982, EMBO J. 1:234, incorporated herein by reference in its entirety).

5.7 Prophylactic & Therapeutic Uses

In one aspect, provided herein are methods for inducing an immune response in a subject utilizing a recombinant influenza virus described herein or an immunogenic composition thereof. In a specific embodiment, a method for inducing an immune response to an influenza virus in a subject comprises administering to a subject in need thereof an effective amount of a recombinant influenza virus or an immunogenic composition thereof. In certain embodiments, the recombinant influenza virus or immunogenic composition thereof expresses influenza virus proteins from two or more types, subtypes or strains of influenza virus, and thus, may be used to induce an immune response to two or more types, subtypes or strains of influenza virus. In a specific embodiment, a method for inducing an immune response to an influenza virus in a subject comprises administering to a subject in need thereof a recombinant influenza virus described herein as a live virus vaccine. In particular embodiments, the live virus vaccine comprises an attenuated virus. In another embodiment, a method for inducing an immune response to an influenza virus in a subject comprises administering to a subject in need thereof a recombinant influenza virus described herein as an inactivated virus vaccine.

In another aspect, provided herein are methods for preventing and/or treating an influenza virus infection in a subject utilizing a recombinant influenza virus described herein or a pharmaceutical composition thereof. In one embodiment, a method for preventing or treating an influenza virus infection in a subject comprises administering to a subject in need thereof an effective amount of a recombinant influenza virus or a composition thereof. In another embodiment, a method for preventing or treating an influenza virus infection in a subject comprises administering to a subject in need thereof an effective amount of a recombinant influenza virus or a pharmaceutical composition thereof and one or more other therapies. In another embodiment, a method for preventing or treating an influenza virus infection in a subject comprises administering to a subject in need thereof a recombinant influenza virus described herein as a live virus vaccine. In particular embodiments, the live virus vaccine comprises an attenuated virus. In another embodiment, a method for preventing or treating an influenza virus infection in a subject comprises administering to a subject in need thereof a recombinant influenza virus described herein as an inactivated virus vaccine.

In another aspect, provided herein are methods for preventing and/or treating an influenza virus disease in a subject utilizing a recombinant influenza virus described herein or a pharmaceutical composition thereof. In a specific embodiment, a method for preventing or treating an influenza virus disease in a subject comprises administering to a subject in need thereof an effective amount of a recombinant influenza virus or a pharmaceutical composition thereof. In another embodiment, a method for preventing or treating an influenza virus disease in a subject comprises administering to a subject in need thereof an effective amount of a recombinant influenza virus or a pharmaceutical composition thereof and one or more other therapies. In another embodiment, a method for preventing or treating an influenza virus disease in a subject comprises administering to a subject in need thereof a recombinant influenza virus described herein as a live virus vaccine. In particular embodiments, the live virus vaccine comprises an attenuated virus. In another embodiment, a method for preventing or treating an influenza virus disease in a subject comprises administering to a subject in need thereof a recombinant influenza virus described herein as an inactivated virus vaccine.

In another aspect, a recombinant influenza virus described herein may be used as a delivery vector. In a specific embodiment, a recombinant influenza virus described herein that expresses a protein heterologous to influenza virus may be used as a vector to deliver the protein to a subject. For example, a recombinant influenza virus described herein may express a cytokine or growth factor which is beneficial to a subject. In another specific embodiment, a recombinant influenza virus described herein that expresses an antigen heterologous to influenza virus may be used as a vector to deliver the antigen to a subject to induce an immune response to the antigen. In some embodiments, the antigen is derived from an infectious pathogen, such as a non-influenza virus antigen, a bacterial antigen, a fungal antigen, or a parasitic antigen. In certain embodiments, the antigen is a tumor antigen or a tumor-associated antigen. Recombinant influenza viruses described herein that express influenza virus antigens and one or more antigens heterologous to influenza virus may induce an immune response to influenza virus and the heterologous antigen(s). In one embodiment, recombinant influenza viruses described herein that express influenza virus antigens and one or more antigens heterologous to influenza virus may induce an immune response to influenza virus and a peptide or polypeptide encoded by a heterologous nucleotide sequence described herein. In one embodiment, such a recombinant virus is used in combination therapy against influenza and an infection or disease associated with the heterologous peptide or polypeptide described herein.

In a specific embodiment, a live recombinant influenza virus described herein that expresses a protein heterologous to influenza virus is administered via a route different than the natural route of infection. For example, such a recombinant influenza virus may be administered intravenously to a subject. In one embodiment, the recombinant influenza virus is administered via the natural route of influenza infection. For example, in some embodiments, the recombinant influenza virus is administered via the respiratory tract, e.g., intranasally.

In another aspect, provided herein are methods of preventing and/or treating an influenza virus infection in a subject by administering neutralizing antibodies described herein. In a specific embodiment, a method for preventing or treating an influenza virus infection in a subject comprises administering to a subject in need thereof an effective amount of a neutralizing antibody described herein, or a pharmaceutical composition thereof. In another embodiment, a method for preventing or treating an influenza virus infection in a subject comprises administering to a subject in need thereof an effective amount of a neutralizing antibody described herein, or a pharmaceutical composition thereof and one or more other therapies. In particular embodiments, the neutralizing antibody is a monoclonal antibody.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In another embodiment, a method for preventing or treating an influenza virus disease in a subject comprises administering to a subject in need thereof an effective amount of a neutralizing antibody described herein, or a pharmaceutical composition thereof and one or more other therapies. In particular embodiments, the neutralizing antibody is a monoclonal antibody.

5.7.1 Patient Population

In one embodiment, a patient treated or prevented in accordance with the methods provided herein is a naïve subject, i.e., a subject that does not have a disease caused by influenza virus infection or has not been and is not currently infected with an influenza virus infection. In another embodiment, a patient treated or prevented in accordance with the methods provided herein is a naïve subject that is at risk of acquiring an influenza virus infection. In another embodiment, a patient treated or prevented in accordance with the methods provided herein is a patient suffering from or expected to suffer from an influenza virus disease. In another embodiment, a patient treated or prevented in accordance with the methods provided herein is a patient diagnosed with an influenza virus infection or a disease associated therewith. In some embodiments, a patient treated or prevented in accordance with the methods provided herein is a patient infected with an influenza virus that does not manifest any symptoms of influenza virus disease.

In another embodiment, a patient treated or prevented in accordance with the methods provided herein is a patient experiencing one or more symptoms of influenza virus disease. Symptoms of influenza virus disease include, but are not limited to, body aches (especially joints and throat), fever, nausea, headaches, irritated eyes, fatigue, sore throat, reddened eyes or skin, and abdominal pain. In another embodiment, a patient treated or prevented in accordance with the methods provided herein is a patient with influenza virus disease who does not manifest symptoms of the disease that are severe enough to require hospitalization.

In another embodiment, a patient treated or prevented in accordance with the methods provided herein is a patient infected with an influenza A virus, an influenza B virus or influenza C virus. In another embodiment, a patient treated or prevented in accordance with the methods provided herein is a patient infected with a particular subtype of influenza A virus. In another embodiment, a patient treated or prevented in accordance with the methods provided herein is a patient infected with an H1 or H3 subtype influenza A virus. In accordance with such embodiments, the patients that are infected with the virus may manifest symptoms of influenza virus disease.

In some embodiments, a patient administered a recombinant influenza virus in accordance with the methods provided herein is an animal. In certain embodiments, the animal is a bird. In certain embodiments, the animal is a mammal, e.g., a horse, swine, mouse, or primate, preferably a human.

In a specific embodiment, a patient administered a recombinant influenza virus in accordance with the methods provided herein is a human. In certain embodiments, a patient administered a recombinant influenza virus in accordance with the methods provided herein is a human infant. In some embodiments, a patient administered a recombinant influenza virus in accordance with the methods provided herein is a human toddler. In certain embodiments, a patient administered a recombinant influenza virus in accordance with the methods provided herein is a human child. In other embodiments, a patient administered a recombinant influenza virus in accordance with the methods provided herein is a human adult. In some embodiments, a patient administered a recombinant influenza virus in accordance with the methods provided herein is an elderly human.

In certain embodiments, a patient administered a recombinant influenza virus in accordance with the methods provided herein is patient that is pregnant. In another embodiment, a patient administered a recombinant influenza virus in accordance with the methods provided herein is a patient who may or will be pregnant during the influenza season (e.g., November to April in the Northern hemisphere).

In some embodiments, a patient treated or prevented in accordance with the methods provided herein is any subject at increased risk of influenza virus infection or disease resulting from influenza virus infection (e.g., an immunocompromised or immunodeficient individual). In some embodiments, a patient treated or prevented in accordance with the methods provided herein is any subject in close contact with an individual with increased risk of influenza virus infection or disease resulting from influenza virus infection (e.g., immunocompromised or immunosuppressed individuals).

In some embodiments, a patient treated or prevented in accordance with the methods provided herein is a subject affected by any condition that increases susceptibility to influenza virus infection or complications or disease resulting from influenza virus infection. In other embodiments, a patient treated or prevented in accordance with the methods provided herein is a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, asthma, or bacterial infections; cardiovascular disease; or diabetes. Other conditions that may increase influenza virus complications include kidney disorders; blood disorders (including anemia or sickle cell disease); or weakened immune systems (including immunosuppression caused by medications, malignancies such as cancer, organ transplant, or HIV infection).

In some embodiments, a patient treated or prevented in accordance with the methods provided herein is a subject that resides in a group home, such as a nursing home or orphanage. In some embodiments, a patient treated or prevented in accordance with the methods provided herein is subject that works in, or spends a significant amount of time in, a group home, e.g., a nursing home. In some embodiments, a patient treated or prevented in accordance with the methods provided herein is a health care worker (e.g., a doctor or nurse).

In some embodiments, a patient treated or prevented in accordance with the methods provided herein is a subject at increased risk of developing complications from influenza virus infection including: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, a patient administered a recombinant influenza virus in accordance with the methods provided herein includes healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza virus disease.

In specific embodiments, a patient administered a recombinant influenza virus in accordance with the methods provided herein is an individual who is susceptible to adverse reactions to conventional therapies. In other embodiments, the patient may be a person who has proven refractory to therapies other than a recombinant influenza virus or antibody described herein but are no longer on these therapies. In certain embodiments, a patient with an influenza virus disease is refractory to a therapy when the infection has not significantly been eradicated and/or the symptoms have not been significantly alleviated. The determination of whether a patient is refractory can be made either in vivo or in vitro by any method known in the art for assaying the effectiveness of a therapy for a disease or infections, using art-accepted meanings of "refractory" in such a context. In various embodiments, a patient with an influenza virus disease is refractory when viral replication has not decreased or has increased following therapy.

In certain embodiments, patients administered a recombinant influenza virus in accordance with the methods provided herein are patients already being treated with antibiotics, anti-virals, anti-fungals, or other biological therapy/immunotherapy. Among these patients are refractory patients, patients who are too young for conventional therapies, and patients with reoccurring influenza virus disease or a symptom relating thereto despite treatment with existing therapies.

In certain embodiments, patients receiving a recombinant influenza virus described herein that expresses a protein heterologous to influenza virus are patients that may benefit from the expression of such a protein. For example, if the heterologous protein is a cytokine or growth factor and the patient has a condition or disease, the expression of the cytokine or growth factor may beneficial for the treatment of the condition or disease.

In certain embodiments, patients receiving a recombinant influenza virus described herein that expresses an antigen heterologous to influenza virus are patients that are infected or susceptible to infection with the pathogen from which the heterologous antigen is derived. In some embodiments, patients receiving a recombinant influenza virus described herein that expresses an antigen heterologous to influenza virus are patients that are diagnosed with an infection with the pathogen from which the heterologous antigen is derived. In some embodiments, patients receiving a recombinant influenza virus described herein that expresses an antigen heterologous to influenza virus are patients manifest one or more symptoms of a disease associated with an infection with the pathogen from which the heterologous antigen is derived. In some embodiments, patients receiving a recombinant influenza virus described herein that expresses an antigen heterologous to influenza virus are patients that are diagnosed with a disease associated with an infection with the pathogen from which the heterologous antigen is derived.

In certain embodiments, patients receiving a recombinant influenza virus described herein that expresses a tumor antigen or tumor associated antigen are patients with cancer, susceptible to cancer or at risk of getting cancer. In some embodiments, patients receiving a recombinant influenza virus described herein that expresses a tumor antigen or tumor associated antigen are patients with a genetic predisposition for cancer. In certain embodiments, patients receiving a recombinant influenza virus described herein that expresses a tumor antigen or tumor associated antigen are patients with diagnosed with cancer. In specific embodiments, the tumor antigen or tumor associated antigen expressed by a recombinant influenza virus makes sense with respect to the cancer being treated. For example, if a subject has lung cancer, a recombinant influenza virus that expresses an antigen associated with the lung cancer is administered the subject. In a specific embodiment, the cancer is a solid tumor cancer, such as, e.g., a sarcoma, melanoma, lymphoma and carcinoma. In another embodiment, the cancer is a non-solid cancer, such as leukemia. Non-limiting examples of cancers include brain cancer, lung cancer, colon cancer, pancreatic cancer, liver cancer, skin cancer, breast cancer, prostate cancer, skin cancer, kidney cancer, bone cancer, and uterine cancer.

5.7.2 Dosage & Frequency of Administration

A recombinant influenza virus, an antibody or a composition described herein may be delivered to a subject by a variety of routes. These include, but are not limited to, intranasal, intratracheal, oral, intradermal, intramuscular, topical intraperitoneal, transdermal, intravenous, pulmonary, conjunctival and subcutaneous routes. In some embodiments, a composition is formulated for topical administration, for example, for application to the skin. In specific embodiments, the composition is formulated for nasal administration, e.g., as part of a nasal spray. In certain embodiments, a composition is formulated for intramuscular administration. In some embodiments, a composition is formulated for subcutaneous administration. In some embodiments, a composition is formulated for administration via the natural route of influenza viral infection. In certain embodiments, a composition is formulated for administration via a route other than the natural route of influenza virus infection. For example, the composition may be formulated for intravenous administration. In specific embodiments for live virus vaccines, the vaccine is formulated for administration by a route other than injection.

When a recombinant influenza virus is to be administered to a subject, it may be preferable to introduce an immunogenic composition via the natural route of infection of influenza virus. The ability of a recombinant influenza virus to induce a vigorous secretory and cellular immune response can be used advantageously. For example, infection of the respiratory tract by a recombinant influenza virus may induce a strong secretory immune response, for example in the urogenital system, with concomitant protection against an influenza virus. In addition, in some embodiments it may be desirable to introduce the pharmaceutical compositions into the lungs by any suitable route. Pulmonary administration can also be employed, e.g., by use of an inhaler or nebulizer, and formulation with an aerosolizing agent for use as a spray.

In some embodiments, when a recombinant influenza virus or a composition thereof is administered to a non-human subject (e.g., a non-human subject), the virus or composition is administered orally to the subject in the subject's food. In other embodiments, when a recombinant influenza virus or a composition thereof is administered to a subject (e.g., a non-human subject), the virus or composition is administered orally to the subject in the subject's water. In other embodiments, when a recombinant influenza virus or a composition thereof is administered to a non-human subject, the virus or composition is administered by spraying the subject with the virus or composition.

The amount of a recombinant influenza virus, an antibody or composition described herein which will be effective in the treatment and/or prevention of an influenza virus infection or an influenza virus disease will depend on the nature of the disease, and can be determined by standard clinical techniques. The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, whether other medications are administered, and whether treatment is prophylactic or therapeutic. Similarly, the amount of a recombinant influenza virus or a composition thereof that will be effective as a delivery vector will vary and can be determined by standard clinical techniques. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for live recombinant influenza virus may vary from 10-100, or more, virions per dose. In some embodiments, suitable dosages of a live recombinant influenza virus are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed. In another embodiment, a live recombinant influenza virus is formulated such that a 0.2-mL dose contains $10^{6.5}$-$10^{7.5}$ fluorescent focal units of live recombinant influenza viruses. In another embodiment, an inactivated vaccine is formulated such that it contains about 15 µg to about 100 µg, about 15 µg to about 75 µg, about 15 µg to about 50 µg, or about 15 µg to about 30 µg of an influenza hemagglutinin.

In certain embodiments, a recombinant influenza virus described herein or a composition thereof is administered to a subject as a single dose followed by a second dose 3 to 6 weeks later. In accordance with these embodiments, booster inoculations may be administered to the subject at 6 to 12 month intervals following the second inoculation. In certain embodiments, the booster inoculations may utilize a different recombinant influenza virus or a composition thereof. In some embodiments, the administration of the same recombinant influenza virus or a composition thereof may be repeated and the administrations may be separated by at least 1 day, 2 days, 3 days, 5 days, 10 days, 15 days, 30 days, 45 days, 2 months, 75 days, 3 months, or at least 6 months.

In specific embodiments for administration to children, two doses of a recombinant influenza virus described herein or a composition thereof, given at least one month apart, are administered to a child. In specific embodiments for administration to adults, a single dose of a recombinant influenza virus described herein or a composition thereof is given. In another embodiment, two doses of a recombinant influenza virus described herein or a composition thereof, given at least one month apart, are administered to an adult. In another embodiment, a young child (six months to nine years old) may be administered a recombinant influenza virus described herein or a composition thereof for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an immunogenic composition described herein, for the first time. In certain embodiments, for children 6-35 months of age, a half dose (0.25 ml) may be preferred, in contrast to 0.5 ml which may be preferred for subjects over three years of age.

In particular embodiments, a recombinant influenza virus or a composition thereof is administered to a subject in the fall or winter, i.e., prior to or during the influenza season in each hemisphere. In one embodiment, children are administered their first dose early in the season, e.g., late September or early October for the Northern hemisphere, so that the second dose can be given prior to the peak of the influenza season.

For passive immunization with an antibody, the dosage ranges from about 0.0001 to 100 mg/kg, and more usually 0.01 to 50 mg/kg or 0.1 to 15 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the recombinant influenza virus in the patient.

5.7.3 Additional Therapies

In various embodiments, a recombinant influenza virus or an antibody described herein may be administered to a subject in combination with one or more other therapies (e.g., antiviral or immunomodulatory therapies). In some embodiments, a pharmaceutical composition described herein may be administered to a subject in combination with one or more therapies. The one or more other therapies may be beneficial in the treatment or prevention of an influenza virus disease or may ameliorate a condition associated with an influenza virus disease.

In some embodiments, the one or more other therapies that are supportive measures, such as pain relievers, anti-fever medications, or therapies that alleviate or assist with breathing. Specific examples of supportive measures include humidification of the air by an ultrasonic nebulizer, aerolized racemic epinephrine, oral dexamethasone, intravenous fluids, intubation, fever reducers (e.g., ibuprofen, acetaminophen), and antibiotic and/or anti-fungal therapy (i.e., to prevent or treat secondary bacterial and/or fungal infections).

In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may be used in combination with a recombinant influenza virus or an antibody described herein or pharmaceutical composition thereof. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, alpha-interferons and other interferons, AZT, zanamivir, and oseltamivir. In certain embodiments, a recombinant influenza virus described herein, an antibody generated in accordance with the methods described herein or a pharmaceutical composition described herein is administered in combination with an influenza virus vaccine, e.g., Fluarix® (GlaxoSmithKline), FluMist® (Medlmmune Vaccines), Fluvirin® (Chiron Corporation), Fluzone® (Aventis Pasteur). In specific embodiments, the anti-viral agent is an immuno-modulatory agent that is specific for a viral antigen. In particular embodiments, the viral antigen is an influenza virus antigen.

In a specific embodiment, one or more therapies that prevent or treat secondary responses to a primary influenza virus infection are administered in combination with a recombinant influenza virus described herein, an antibody generated in accordance with the methods provided herein, or a pharmaceutical composition described herein. Examples of secondary responses to a primary influenza virus infection include, but are not limited to, asthma-like responsiveness to mucosal stimuli, elevated total respiratory resistance, increased susceptibility to secondary viral, bacterial, and fungal infections, and development of conditions such as, but not limited to, bronchiolitis, pneumonia, croup, and febrile bronchitis.

In some embodiments, a recombinant influenza virus described herein or a pharmaceutical composition thereof is administered in combination with an antibody that specifically binds to an influenza virus antigen.

In some embodiments, a recombinant influenza virus described herein or a pharmaceutical composition thereof is administered in combination with an anti-viral agent (e.g., an anti-influenza agent described herein, or an anti-bacterial, anti-fungal, or anti-cancer agent described herein or known in the art).

5.8 Screening Assays

In one aspect, a recombinant influenza virus described herein may be used to study the life cycle of an influenza virus. For example, a recombinant influenza virus described herein that expresses a detectable heterologous sequence (e.g., a detectable substance such as described above) is introduced into a host cell and the life cycle of the virus is monitored by the assessing the expression of the detectable heterologous sequence. A recombinant influenza virus described herein that expresses a detectable heterologous sequence may also be administered to a non-human animal and the infection monitored by assessing the expression of the detectable heterologous sequence.

In another aspect, a recombinant influenza virus described herein may be used to study the effect of a compound on the life cycle of an influenza virus. For example, a recombinant influenza virus described herein that expresses a detectable heterologous sequence (e.g., a detectable substance such as described supra) is introduced into a host cell together with the compound and the compound's effect on the life cycle of the virus is monitored by the assessing the expression of the detectable heterologous sequence. A recombinant influenza virus described herein that expresses a detectable heterologous sequence may also be administered to a non-human animal and the infection monitored by assessing the expression of the detectable heterologous sequence.

In another aspect, provided herein are high throughput screening assays for the identification or validation of compounds that modulate the replication of negative-sense, single-stranded RNA viruses, in particular influenza viruses. In a specific embodiment, the high throughput screening assay to identify a compound that modulates the replication of a negative-sense, single-stranded RNA virus (in particular influenza virus) comprises: (a) contacting a compound or a member of a library of compounds with a host cell infected with a recombinant influenza virus described herein that expresses a detectable heterologous nucleotide sequence; and (b) measuring the expression or activity of a product encoded by the detectable heterologous nucleotide sequence. In another embodiment, the high throughput screening assay to identify a compound that modulates the replication of a negative-sense, single-stranded RNA virus (in particular influenza virus) comprises: (a) infecting a host cell with a recombinant influenza virus described herein that expresses a detectable heterologous nucleotide sequence in the presence of a compound or a member of a library of compounds; and (b) measuring the expression or activity a product encoded by the detectable heterologous nucleotide sequence. In another embodiment, the high throughput screening assay to identify a compound that modulates the replication of a negative-sense, single-stranded RNA virus (in particular influenza virus) comprises: (a) contacting a host cell with a compound or a member of a library of compounds: (b) infecting the host cell with a recombinant influenza virus described herein that expresses a detectable heterologous nucleotide sequence; and (c) measuring the expression or activity a product encoded by the detectable heterologous nucleotide sequence.

In some embodiments, the high throughput screening assays involve: (a) contacting a compound or a member of a library of compounds with a cell before (e.g., 15 minutes, 30 minutes, 1 hour, 2 hours, 4 hours, 6 hours, 12 hours, 24 hours or more before), concurrently and/or subsequent to (e.g., 15 minutes, 30 minutes, 1 hour, 2 hours, 4 hours, 6 hours, 12 hours, 24 hours or more after) infection with a recombinant influenza virus described herein that expresses a detectable heterologous nucleotide sequence; and (b) measuring the expression or activity a product encoded by the detectable heterologous nucleotide sequence. The cells can be infected with different MOIs (e.g., 0.001, 0.005, 0.01, 0.05, 0.1, 0.5, 1, 2.5, or 5) and the effect of compounds can be assessed in the screening assays. The effect of different concentrations of the compounds can also be assessed using in the screening assays. The expression or activity of a product encoded by the detectable heterologous nucleotide sequence can be measured at different times post-infection. For example, the expression or activity of the detectable heterologous nucleotide sequence may be measured 6 hours, 12 hours, 24 hours, 48 hours or 72 hours post-infection. A compound that increases the replication of a negative-sense, single-stranded RNA virus (in particular, influenza virus) is identified if the level of expression or activity a product encoded by the detectable heterologous nucleotide sequence is increased in the host cell contacted with the compound relative to the level of expression or activity a product encoded by the detectable heterologous nucleotide sequence in a host cell contacted with a negative control. In contrast, a compound that decreases the replication of a negative-sense, single-stranded RNA virus (in particular, influenza virus) is identified if the level of expression or activity a product encoded by the detectable heterologous nucleotide sequence is decreased in the host cell contacted with the compound relative to the level of expression or activity of a product encoded by the detectable heterologous nucleotide sequence in a host cell contacted with a negative control.

In some embodiments, an embryonated egg or any other substrate that permits the replication of an influenza virus may be used in place of the cells used in the high throughput screening assays described herein.

In a specific embodiment, the host cell used in the high throughput assay for screening for compounds that modulate replication of an influenza virus is a host cell that permits infection with the influenza virus. In some embodiments, the high throughput assay for screening for compounds that modulate replication of a negative-sense, single-stranded RNA virus (in particular, an influenza virus) uses any substrate that allows the virus to grow to titers that permits the use of such viruses in the screening assays. By way of non-limiting example, substrates useful in the high throughput screening assays described herein include cells (e.g. avian cells, chicken cells (e.g., primary chick embryo cells or chick kidney cells), Vero cells, MDCK cells, human respiratory epithelial cells (e.g., A549 cells), calf kidney cells, mink lung cells, etc.) that are susceptible to infection by the viruses or embryonated eggs or animals (e.g., birds). In one embodiment, the cells used in the high throughput screening assay are biologically relevant to the type of infection.

In a specific embodiment, a product encoded by the detectable heterologous nucleotide sequence measured in the high throughput screening assays described above is an RNA product. In another embodiment, a product encoded by the detectable heterologous nucleotide sequence measured in the high throughput screening assays described above is a protein product. In another embodiment, the activity of a product encoded by the detectable heterologous nucleotide sequence is measured in the high throughput screening assays described above and the product is protein.

Any method known to one of skill in the art can be used measure the expression or activity of a product encoded by the detectable heterologous nucleotide sequence. In one embodiment, the product encoded by the detectable heterologous nucleotide sequence is RNA and a technique known to one of skill in the art, such as RT-PCR or Northern blot analysis, is used to measure the expression of the RNA product. In another embodiment, the product encoded by the detectable heterologous nucleotide sequence is protein and a technique known to one of skill in the art, such as western blot analysis or an ELISA, is used to measure the expression of the protein product. In another embodiment, the product encoded by the detectable heterologous nucleotide sequence is protein and the activity of the protein is measured using a technique known to one of skill in the art.

Any screening assay described herein can be performed individually, e.g., just with the test compound, or with appropriate controls. For example, a parallel assay without the test compound, or other parallel assays without other reaction components (e.g., virus) can be performed. In one embodiment, a parallel screening assay as described above is performed except that a negative control and/or a positive control are used in place of a test compound. In another embodiment, to eliminate cytotoxic compounds that appear as false positives, a counter screen is performed in which uninfected cells are transfected with a nucleic acid construct (e.g., a plasmid) comprising a detectable heterologous nucleotide sequence and the expression or activity of a product encoded by the detectable heterologous nucleotide sequence is measured. Alternatively, it is possible to compare assay results to a reference, e.g., a reference value, e.g., obtained from the literature, a prior assay, and so forth. Appropriate correlations and art known statistical methods can be used to evaluate an assay result.

In some embodiments, the average expression or activity of the product encoded by the detectable heterologous nucleotide sequence when a negative control (e.g., PBS) is contacted with cell is determined and the percent expression or activity of the product for each compound is determined in relation to this internal control. In one embodiment, the average percent expression or activity the product encoded by the detectable heterologous nucleotide sequence is calculated and the compounds are classified as strong or medium inhibitors of virus replication based on a 90% to 100% or 70% to 89% reduction in the expression or activity of the product, respectively. In another embodiment, the compounds are classified as enhancers of viral replication if at least a 2 fold increase in the expression or activity of a product encoded by the detectable heterologous nucleotide sequence above relative to the negative control is obtained.

In another aspect, the antiviral effect of a compound on influenza virus can be assessed in a non-human animal using a recombinant influenza virus described herein. In one embodiment, the antiviral effect of a compound on influenza virus can be assessed by a method comprising: (a) administering (for example, parenterally, subcutaneously, intranasally, or intraperitoneally) to a non-human subject, concurrently, subsequently or prior to administration of a compound, an effective amount of a recombinant influenza virus described herein; b) waiting for a time interval following the administration of the recombinant influenza virus; and d) detecting the recombinant influenza virus in the subject or in a biological specimen from the subject.

5.9 Kits

In one aspect, provided herein is a kit comprising, in one or more containers, one or more nucleic acid sequences described herein. In a specific embodiment, a kit comprises, in a container, a modified influenza virus NS gene segment or a complement thereof. In another embodiment, a kit comprises, in one, two or more containers, a nucleic acid sequence encoding a modified influenza virus NS gene segments or a complement thereof. The kit may further comprise one or more of the following: host cells suitable for rescue of the virus, reagents suitable for transfecting plasmid DNA into a host cell, helper virus, plasmids encoding one or more types of influenza virus gene segments, one or more expression plasmids encoding viral proteins, and/or one or more primers specific for a modified influenza virus NS gene segment or a complement thereof, or nucleic acid sequences encoding the same.

In another aspect, provided herein is a kit comprising one or more containers filled with one or more of the one or more recombinant influenza virus described herein or a composition thereof. In a specific embodiment, provided herein is a pharmaceutical pack or kit comprising, in one or more containers, a composition comprising one or more recombinant influenza viruses described herein. In another aspect, provided herein is a kit comprising, in one or more containers, primers specific for a particular modified influenza virus NS gene segment.

In another aspect, provided herein is a kit comprising one or more containers filled with one or more antibodies generated or identified using a recombinant influenza virus described herein. In one embodiment, a kit comprises an antibody described herein, preferably an isolated antibody, in one or more containers. In a specific embodiment, a kit encompassed herein contains an isolated influenza virus antigen that the antibodies encompassed herein react with as a control. In a specific, a kit provided herein further comprise a control antibody which does not react with an influenza virus antigen that an antibody encompassed herein reacts with. In another specific embodiment, a kit provided herein contains a means for detecting the binding of an antibody to an influenza virus antigen that an antibody encompassed herein reacts with (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, a kit may include a recombinantly produced or chemically synthesized influenza virus antigen. The influenza virus antigen provided in the kit may also be attached to a solid support. In a more specific embodiment the detecting means of the above described kit includes a solid support to which an influenza virus antigen is attached. Such a kit may also include a non-attached reporter-labeled anti-human antibody. In this embodiment, binding of the antibody to the Influenza virus antigen can be detected by binding of the said reporter-labeled antibody.

Optionally associated with such a kit can be a notice in the form prescribed by a governmental agency regulating the manufacture, use or sale of pharmaceuticals or biological products, which notice reflects approval by the agency of manufacture, use or sale for human administration.

5.10 Biological Assays

Presence of Modified Influenza Virus Gene Segment

The skilled artisan could detect a modified influenza virus NS gene segment or the gene products of a modified influenza virus NS gene segment of interest using techniques known in the art. For example, RT-PCR can be used with primers that are specific to a modified influenza virus NS gene segment to detect and quantify a modified influenza virus NS gene segment of interest. Western blot, ELISA, radioimmunoassay, immunoprecipitation, immunocytochemistry, or immunocytochemistry in conjunction with FACS can be used to quantify the gene products of a modified influenza virus NS gene segment of interest.

Viral Assays

Viral assays include those that measure viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of a recombinant influenza virus described herein can be assessed by any method known in the art or described herein (e.g., in cell culture (e.g., cultures of chicken embryonic kidney cells or cultures of chicken embryonic fibroblasts (CEF)). Viral titer may be determined by inoculating serial dilutions of a recombinant influenza virus described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. An hemagglutinin (HA) assay may be carried out in V-bottom 96-well plates. Serial twofold dilutions of each sample in PBS are incubated for 1 h on ice with an equal volume of a 0.5% suspension of chicken erythrocytes in PBS. Positive wells contain an adherent, homogeneous layer of erythrocytes; negative wells contain a nonadherent pellet. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50).

Antibody Assays

Antibodies generated or identified in accordance with the methods described herein may be characterized in a variety of ways well-known to one of skill in the art (e.g., ELISA, Surface Plasmon resonance display (BIAcore), Western blot, immunofluorescence, immunostaining and/or microneutralization assays). In particular, antibodies generated or identified in accordance may be assayed for the ability to specifically bind to an antigen of the recombinant influenza virus. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S.

Pat. Nos. 5,571,698; 5,403,484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference). Antibodies that specifically bind to an antigen of a recombinant influenza virus can then be assayed for their specificity to said antigen.

Antibodies generated or identified in accordance with the methods described herein may be assayed for specific binding to an antigen of a recombinant virus described herein and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody can be determined from the data by Scatchard plot analysis. Competition with a second antibody can also be determined using radioimmunoassays. In this case, a recombinant virus of described herein or an antigen thereof is incubated with an antibody against the antigen conjugated to a labeled compound (e.g., $^3$H or $^{125}$I) in the presence of increasing amounts of an unlabeled second antibody.

BIAcore kinetic analysis can be used to determine the binding on and off rates of an antibody to an antigen of a recombinant influenza virus described herein. BIAcore kinetic analysis comprises analyzing the binding and dissociation of polypeptide comprising the antigen of interest from chips with immobilized antibodies generated or identified in accordance with methods described herein on their surface. A typical BIAcore kinetic study involves the injection of 250 uL of an antibody reagent (mAb, Fab) at varying concentration in HBS buffer containing 0.005% Tween-20 over a sensor chip surface, onto which has been immobilized the antigen. The flow rate is maintained constant at 75 uL/min. Dissociation data is collected for 15 min. or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, kon, and dissociation, koff, the polypeptide comprising the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide comprising the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, KD, is estimated to be. As described above, the bound antibody is removed after each injection/dissociation cycle using an appropriate regenerant.

Antibodies generated or identified in accordance with the methods described herein can also be assayed for their ability to inhibit the binding of an antigen of a recombinant influenza virus to a host cell using techniques known to those of skill in the art. For example, cells expressing receptors known to bind to influenza virus can be contacted with influenza virus in the presence or absence of an antibody generated or identified in accordance with the methods described herein and the ability of the antibody to inhibit the binding can measured by, for example, flow cytometry or a scintillation assay. The antigen or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the influenza virus and a cell.

Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g., in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of influenza and subsequently cultured in the presence or absence of various dilutions of antibodies (e.g., 0.1 μg/ml, 1 μg/ml, 5 μg/ml, or 10 μg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, an antibody compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more.

Cytotoxicity Assays

Many assays well-known in the art can be used to assess viability of cells (infected or uninfected) or cell lines following exposure to a recombinant influenza virus, an antibody described herein or a composition thereof, and, thus, determine the cytotoxicity thereof. For example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79), ($^3$H) thymidine incorporation (see, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a film y appearance, rounding, detachment from the surface of the well, or other changes. These changes are given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cell inhibitory (cytotoxic) concentration (IC50) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

A recombinant influenza virus, an antibody or a composition thereof can be tested for in vivo toxicity in animal models. For example, animal models known in the art can also be used to determine the in vivo toxicity of to test the activities of a recombinant influenza virus, an antibody or a composition thereof. For example, animals are administered a range of concentrations of to test the activities of a recombinant influenza virus, an antibody or a composition thereof. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a recombinant influenza virus, an antibody or a composition thereof can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A recombinant influenza virus, an antibody or a composition thereof that exhibits large therapeutic indices is preferred. While a recombinant influenza virus, an antibody or a composition thereof that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a recombinant influenza virus, an antibody or a composition thereof for use in humans. The dosage of such agents lies preferably within a range of circulating concentrations that include the ED50 with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of a recombinant influenza virus, an antibody or a composition thereof, for example, by measuring viral infection or a condition or symptoms associated therewith.

Animal Model Assays

The virulence of a recombinant influenza virus described herein can be assessed in a subject, in particular an animal model. In one example, the ability to induce lung lesions and cause infection in an animal model of virus infection is compared to wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

A recombinant influenza virus, an antibody or a composition thereof is preferably assayed in vivo for the desired therapeutic or prophylactic activity prior to use in humans. For example, to assess the use of a recombinant influenza virus, an antibody or a composition thereof to prevent an influenza virus disease, the virus, antibody or composition can be administered before the animal is infected with a wild-type influenza virus. Alternatively, or in addition, a recombinant influenza virus, an antibody or a composition thereof can be administered to the animal at the same time that the animal is infected with a wild-type influenza virus. To assess the use of a recombinant influenza virus, an antibody or a composition thereof to treat an influenza virus infection or disease associated therewith, the virus, antibody or composition may be administered after infecting the animal with wild-type influenza virus. In a specific embodiment, a recombinant influenza virus, an antibody or a composition thereof is administered to the animal more than one time.

A recombinant influenza virus, an antibody or a composition thereof can be tested for antiviral activity in animal model systems including, but are not limited to, rats, mice, chicken, cows, monkeys, pigs, goats, sheep, dogs, rabbits, guinea pigs, etc. In a specific embodiment, active compounds and compositions thereof are tested in a mouse model system. Such model systems are widely used and well-known to the skilled artisan. In a specific embodiment, a recombinant influenza virus, an antibody or a composition thereof is tested in a mouse model system. Non-limiting examples of animal models for influenza virus are provided in this section.

In general, animals are infected with wild-type influenza virus and concurrently or subsequently treated with a recombinant influenza virus, an antibody or a composition thereof, or placebo. Alternatively, animals are treated with a recombinant influenza virus, an antibody or a composition thereof, or placebo and subsequently infected with wild-type influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of a recombinant influenza virus, an antibody or a composition thereof on the virulence of a virus can also be determined using in vivo assays in which the titer of the virus in an infected subject administered a recombinant influenza virus, an antibody or a composition thereof, the length of survival of an infected subject administered a recombinant influenza virus, an antibody or a composition thereof, the immune response in an infected subject administered a recombinant influenza virus, an antibody or a composition thereof, the number, duration and/or severity of the symptoms in an infected subject administered a recombinant influenza virus, an antibody or a composition thereof, and/or the time period before onset of one or more symptoms in an infected subject administered a recombinant influenza virus, an antibody or a composition thereof, is assessed. Techniques known to one of skill in the art can be used to measure such effects.

Influenza virus animal models, such as ferret, mouse, guinea pig, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of active compounds administered to the influenza-infected mice include pneumonia-associated death, serum ÿ-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

In addition to animal models for influenza virus, the effectiveness of a recombinant influenza virus described herein to prevent and/or treat a disease of interest may be assessed in an appropriate animal model known to one skilled in the art.

Assays in Humans

In one embodiment, a recombinant influenza virus, an antibody or a composition thereof is assessed in infected human subjects. In accordance with this embodiment, a recombinant influenza virus, an antibody or a composition thereof is administered to the human subject, and the effect of the virus, antibody or composition on viral replication is determined by, e.g., analyzing the level of the virus or viral nucleic acids in a biological sample (e.g., serum or plasma). A recombinant influenza virus, an antibody or a composition thereof that alters virus replication can be identified by comparing the level of virus replication in a subject or group of subjects treated with a control to that in a subject or group of subjects treated with a recombinant influenza virus, an antibody or a composition thereof. Alternatively, alterations in viral replication can be identified by comparing the level of the virus replication in a subject or group of subjects before and after the administration of a recombinant influenza virus, an antibody or a composition thereof. Techniques known to those of skill in the art can be used to obtain the biological sample and analyze the mRNA or protein expression.

In another embodiment, the effect of a recombinant influenza virus, an antibody or a composition thereof on the severity of one or more symptoms associated with an influenza virus infection/disease are assessed in an infected subject. In accordance with this embodiment, a recombinant influenza virus, an antibody or a composition thereof, or a control is administered to a human subject suffering from influenza virus infection and the effect of the virus, antibody or composition on one or more symptoms of the virus infection is determined. A recombinant influenza virus, an antibody or a composition thereof that reduces one or more symptoms can be identified by comparing the subjects treated with a control to the subjects treated with the virus, antibody or composition. Techniques known to physicians familiar with infectious diseases can be used to determine whether an active compound or composition thereof reduces one or more symptoms associated with the influenza virus disease.

For quantitation of virus in tissue samples, tissue samples are homogenized in phosphate-buffered saline (PBS), and dilutions of clarified homogenates adsorbed for 1 h at 37° C. onto monolayers of cells (e.g., CEF or MDCK cells). Infected monolayers are then overlaid with a solution of minimal essential medium containing 0.1% bovine serum albumin (BSA), 0.01% DEAE-dextran, 0.1% NaHCO3, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., CEF or MDCK cells) in 96-well plates are incubated with log dilutions of clarified tissue homogenates in media. Two to three days after inoculation, 0.05-ml aliquots from each well are assessed for viral growth by hemagglutination assay (HA assay).

In yet other assays, histopathologic evaluations are performed after infection. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

6. EXAMPLE

Analysis of In Vivo Dynamics of Influenza Virus Infection Using a GFP Reporter Virus 6.1 Materials and Methods This example demonstrates the successful generation of the first, complete influenza virus carrying GFP report gene (NS1-GFP virus). NS1-GFP virus efficiently replicates in tissue culture and causes significant pathogenicity in mice.

Cell Lines.

Human embryonic kidney (293T) cells were maintained in DMEM supplemented with 10% FBS and 1000u/ml penicillin/streptomycin. Madin-Darby canine kidney (MDCK) cells were maintained in MEM supplemented with 10% FBS and penicillin/streptomycin. Reagents for cell culture were purchased from Gibco Life Technologies.

Construction of NS-GFP Segment.

The NS-GFP (A/Puerto Rico/8/34) segment was generated by overlapping fusion PCR using standard molecular biology techniques. Briefly, NS1 ORF without the stop codon was fused to the N-terminal of codon-optimized maxGFP (Amaxa) via a GSG (SEQ ID NO:1) linker region (NS1-GFP). The maxGFP was followed by a short GSG linker, a 19aa 2A autoproteolytic site (ATNFSLLKQAGDVEENPG↓P) (SEQ ID NO:20) (Donnelly, M. L., L. E. Hughes, G. Luke, H. Mendoza, E. ten Dam, D. Gani, and M. D. Ryan. 2001. The 'cleavage' activities of foot-and-mouth disease virus 2A site-directed mutants and naturally occurring '2A-like' sequences. J Gen Virol 82:1027-41) from porcine teschovirus-1 and NEP ORF. Also, a silent splice acceptor site mutation (SAM; T524C A527G) was introduced to prevent splicing of messenger RNA (Basler, C. F., A. H. Reid, J. K. Dybing, T. A. Janczewski, T. G. Fanning, H. Zheng, M. Salvatore, M. L. Perdue, D. E. Swayne, A. Garcia-Sastre, P. Palese, and J. K. Taubenberger. 2001). Sequence of the 1918 pandemic influenza virus nonstructural gene (NS) segment and characterization of recombinant viruses bearing the 1918 NS genes. Proc Natl Acad Sci USA 98:2746-51). Initially NS1-GFP-2A-NEP would be expressed as a single polyprotein. But after proteolytic cleavage at the 2A site, NS1-GFP will be separated from NEP, with NS1-GFP carrying the 18 aa from 2A site and NEP carrying a proline at the N-terminal end. The entire NS-GFP segment was cloned in the pDZ rescue plasmid (Quinlivan, M., D. Zamarin, A. Garcia-Sastre, A. Cullinane, T. Chambers, and P. Palese. 2005. Attenuation of equine influenza viruses through truncations of the NS1 protein. J Virol 79:8431-9).

Rescue of NS1-GFP virus. NS1-GFP virus (A/Puerto Rico/8/34 background) was rescued using standard reverse genetics techniques (Fodor, E., L. Devenish, O. G. Engelhardt, P. Palese, G. G. Brownlee, and A. Garcia-Sastre. 1999. Rescue of influenza A virus from recombinant DNA. J Virol 73:9679-82, Marsh, G. A., R. Rabadan, A. J. Levine, and P. Palese. 2008. Highly conserved regions of influenza a virus polymerase gene segments are critical for efficient viral RNA packaging. J Virol 82:2295-304, Schickli, J. H., A. Flandorfer, T. Nakaya, L. Martinez-Sobrido, A. Garcia-Sastre, and P. Palese. 2001. Plasmid-only rescue of influenza A virus vaccine candidates. Philos Trans R Soc Lond B Biol Sci 356: 1965-73). Briefly, 0.5 µg of each of 8 pDZ plasmids was transfected into 293T cells. After 24 h, the 293T cells with supernatant were injected into 8-day old eggs. The NS1-GFP virus was harvested from the allantoic fluid at 48 hrs post inoculation (hpi). Although the initial rescue supernatant contained a mix of GFP positive and negative plaques, stable clones of NS1-GFP virus was isolated after three rounds of plaque purification in MDCK cells. The plaque-purified NS1-GFP virus was amplified in 9-day old embryonated eggs. The sequence of NS-GFP segment in the NS1-GFP virus was confirmed by sequencing the RT-PCR product of vRNA. The titers of viral stocks were determined by plaque assay in MDCK cells.

Immunostaining.

A549 cells were infected with NS1-GFP virus at a MOI=1. At 10 hpi, the cells were fixed in 4% formaldehyde (methanol-free) for 10 min. After permeabilization with 0.5% Triton X-100, the cells were stained with a rabbit polyclonal anti-NP antibody followed by anti-rabbit antibody conjugated to Alexa-588 (Invitrogen). Images were acquired on an Olympus XI-70 microscope at 20× using Q-Capture software.

Growth Kinetics.

MDCK cells in 6-well plates were infected at a MOI=1 (single cycle) or 0.01 (multi-cycle) in 200 µl of PBS/0.3% Bovine albumin for 1 hr. After 1 hr, the inoculum was replaced with 3 ml of MEM containing 0.3% BA and 1 µg/ml TPCK-treated trypsin. Approximately 300 µl of viral supernatant was collected at indicated times and the same amount of fresh media was added to the cells. The viral titers were determined by plaque assay in MDCK cells. All experiments were carried out in triplicate.

Western Blot.

MDCK cells in 6-well plates were infected at a MOI=1 and cells were lysed using 1% Triton X-100 lysis buffer (50 mM Tris-HCl [pH 7.5], 150 mM NaCl, 5 mM EDTA, 1% Triton X-100, and protease inhibitors) at the indicated hpi. The protein samples were subjected to sodium dodecyl sulfate-polyacrylamide gel electrophoresis (SDS-PAGE) and transferred to a polyvinylidene difluoride membrane. NS1 and NS1-GFP levels were assessed by immunoblotting with a rabbit polyclonal anti-NS1 antibody raised against the N-terminal 1-73 amino acids of NS1 from A/Swine/Texas/4199-2/98.

Interferon-β Promoter Induction Assay.

MDCK cells stably expressing firefly luciferase under the control of the human interferon-β promoter were infected with a MOI=1. At 18 hpi, the cells were lysed in 200 µl of cell culture lysis reagent (Promega). The luciferase activity was measured with a firefly luciferase assay kit (Promega). Each experiment was done in triplicates and repeated at least three times.

Analysis of vRNA Incorporation in the Virions.

vRNA was extracted from the allantoic fluid using Trizol-LS reagent according to the manufacturer's instructions. vRNA samples (500 ng) were separated on a RNA 6000 Nano Chip and analyzed using Agilent bioanalyzer (Agilent Technologies).

Mice Experiments

Body Weight Loss and Survival.

Female Balb/C mice (5-6 weeks old) were anesthetized with ketamine-Xylaxine and intranasally infected with the indicated virus dose diluted in 50 µl of PBS. Body weight and survival were measured every day. All mice experiments were carried in strict accordance with the institutional protocol. Mice showing more than 20% of body weight loss were considered to have reached the experimental end point and were euthanized.

Lung Titers.

Lungs of infected mice were excised on days 3 and 4 post-infection and homogenized using a mechanical homogenizer. The viral titers in the homogenates were quantified by plaque assay on MDCK cells. Each data point presents the average titer from 3 mice.

Oseltamivir and Amantadine Treatment.

Mice were treated with either 50 mg/Kg of Oseltamivir phosphate in PBS (Roche Laboratories, NJ) or 40 mg/Kg of Amantadine hydrochloride in water (Sigma), administered by oral gavage. The treatments were started either on the day of infection or 2 days post infection and were given once daily until the end of the experiment.

Ex Vivo Imaging of Lungs.

The lungs of infected mice were excised at indicated times post infection. After cleaning the surface with PBS, the lungs were placed on a glass plate and imaged using the IVIS-200 series imaging system (Xenogen Corporation) fitted with GFP excitation/emission filters at 4 s exposure time.

Cryosections of Lungs.

After surface cleaning with PBS, mice lungs were placed in OCT media and slowly frozen in −80° C. The lung sections of 5 µm thickness were cut using a cryostat and placed on a glass slide. The sections were fixed with 4% formaldehyde for 10 min and nuclei were stained with DAPI. Images were acquired on an Olympus XI-70 microscope at 20× using Q-Capture software.

Flow Cytometry

Single Cell Preparation.

Single cell suspensions of mice lung were prepared using collagenase/DNase treatment. Briefly, excised whole lungs were minced in 10 ml of DMEM containing 10 mM HEPES, 5% FBS, 100 u/ml Type IV Collagenase (Worthington) and 100 µg/ml DNase I (Roche), and incubated at 37° C. for 45 min. The tissue pieces were mashed through a 70 µm cell strainer. The cells were washed once with HBSS containing 10 mM HEPES buffer, 2% FBS and 2 mM EDTA followed by filtration using a 40 µm cell strainer. The red blood cells in the preparation were lysed using 1 ml of ACK lysis buffer (Lonza). The cells were pelleted and washed once with HBSS.

Staining and Analysis Cell Surface Markers.

Approximately 1×10$^6$ cells were stained in 100 µl of HBSS (10 mM HEPES, 2% FBS, 2 mM EDTA) using commercially available antibodies in the presence of Fc receptor blocking antibody (2.4G2) for 30 min on ice. The monoclonal antibodies conjugated to different Fluorochromes (PerCP-Cy5.5, APC, APC-CY7, Pacific blue, PE, PE-Cy7) were purchased form BD biosciences and Ebioscience. Flow cytometry was performed on a BD LSR11 using FACSDiva software (BD Biosciences). The data were analyzed using FlowJo Software (Tree Star Inc.)

6.2 Results

Generation of Influenza Virus Expressing GFP.

Figures 1B, 1C:
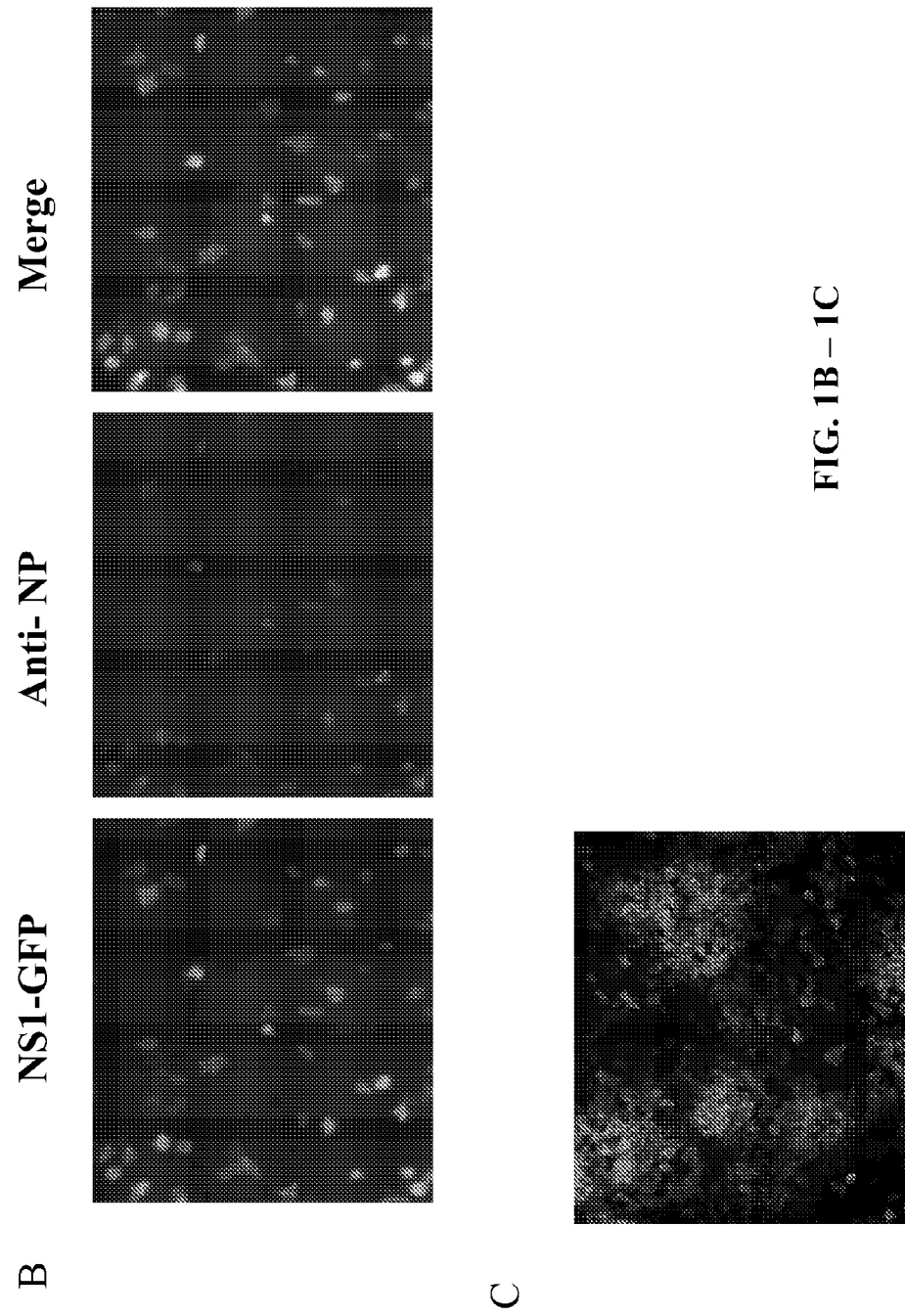

The NS segment of influenza virus encodes two proteins: NS1 produced from unspliced mRNA and NEP produced from spliced mRNA (FIG. 1A). The NS segment has been modified to express NS1-GFP and NEP as a single polyprotein with a 19aa porcine teschovirus-1 (PTV-1) 2A autoproteolytic cleavage site between them allowing NEP to be separated during translation (Basler, C. F., A. H. Reid, J. K. Dybing, T. A. Janczewski, T. G. Fanning, H. Zheng, M. Salvatore, M. L. Perdue, D. E. Swayne, A. Garcia-Sastre, P. Palese, and J. K. Taubenberger. 2001. Sequence of the 1918 pandemic influenza virus nonstructural gene (NS) segment and characterization of recombinant viruses bearing the 1918 NS genes. Proc Natl Acad Sci USA 98:2746-51, Donnelly, M. L., L. E. Hughes, G. Luke, H. Mendoza, E. ten Dam, D. Gani, and M. D. Ryan. 2001. The 'cleavage' activities of foot-and-mouth disease virus 2A site-directed mutants and naturally occurring '2A-like' sequences. J Gen Virol 82:1027-41). Also, two silent mutations have been introduced in the splice acceptor site (SAM mutation) to prevent splicing of NS mRNA (Basler, C. F., A. H. Reid, J. K. Dybing, T. A. Janczewski, T. G. Fanning, H. Zheng, M. Salvatore, M. L. Perdue, D. E. Swayne, A. Garcia-Sastre, P. Palese, and J. K. Taubenberger. 2001. Sequence of the 1918 pandemic influenza virus nonstructural gene (NS) segment and characterization of recombinant viruses bearing the 1918 NS genes. Proc Natl Acad Sci USA 98:2746-51). The NS1-GFP virus was rescued using standard reverse genetics techniques as previously described (Quinlivan, M., D. Zamarin, A. Garcia-Sastre, A. Cullinane, T. Chambers, and P. Palese. 2005. Attenuation of equine influenza viruses through truncations of the NS1 protein. J Virol 79:8431-9). Although, the initial rescue supernatants contained a mixture of both GFP positive and negative virus populations, a stable GFP carrying clone was isolated after three rounds of plaque purification. In order to test if the GFP was expressed in all infected cells, A549 cells were infected with the NS1-GFP virus at a MOI=1 and stained for the viral nucleoprotein (NP), a viral protein critical for replication (FIG. 1B). At 10 hpi, GFP expression was clearly observed in all cells expressing NP (infected cells), suggesting that GFP is expressed in all infected cells. Also, NS1-GFP virus was capable of forming visible plaques and grew to titers of $5 \times 10^8$ pfu/ml in 9-day old embryonated eggs (FIG. 1C). The quality of the GFP virus preparations was determined by examining GFP expression in 20 randomly selected visible plaques and only preparations in which all 20 plaques were GFP positive were used in the experiments.

In Vitro Characterization of NS1-GFP Virus

NS1-GFP Virus Replicates Efficiently in MDCK Cells.

Figure 2A:
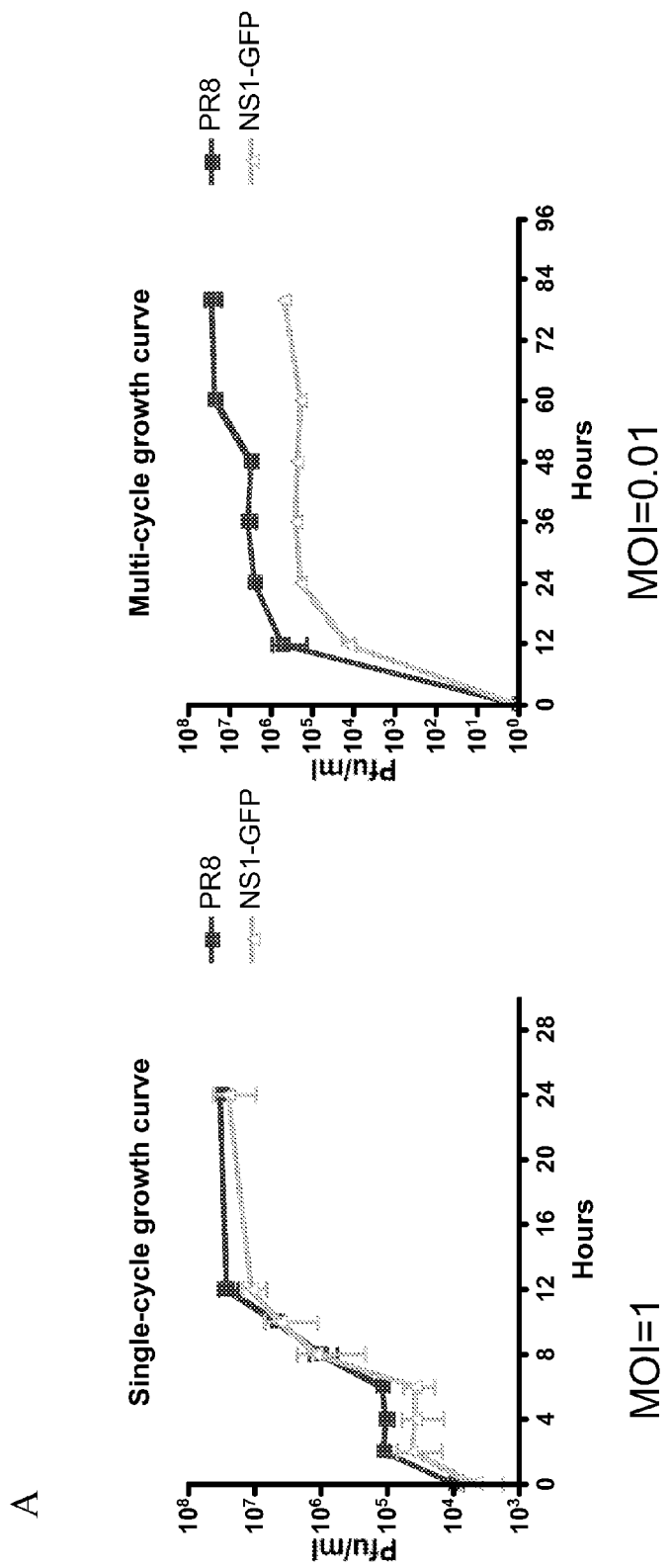

To test if the presence of a longer NS segment in NS1-GFP virus, which is at least twice the size of the wild-type (Wt) NS segment (1.89 kb vs. 0.89 kb), affects the viral life cycle, the growth kinetics of NS1-GFP virus and parental virus Wt PR8 in MDCK cells was compared (FIG. 2A). MDCK cells were infected with either NS1-GFP or Wt PR8 virus at high or low MOI (1 or 0.01) and viral titers in the supernatant were measured at various times post infection. In a single cycle replication assay (MOI=1), NS1-GFP virus showed a similar growth pattern to Wt PR8 virus with titers reaching up to $2 \times 10^7$ pfu/ml. However, in a multi-cycle replication assay (MOI=0.01), NS1-GFP virus showed a slight delay in replication kinetics compared to Wt PR8 with nearly 10-fold difference in the virus titer. This suggests that NS1-GFP virus is slightly less efficient in replication.

Figures 2B, 2C, 2D:
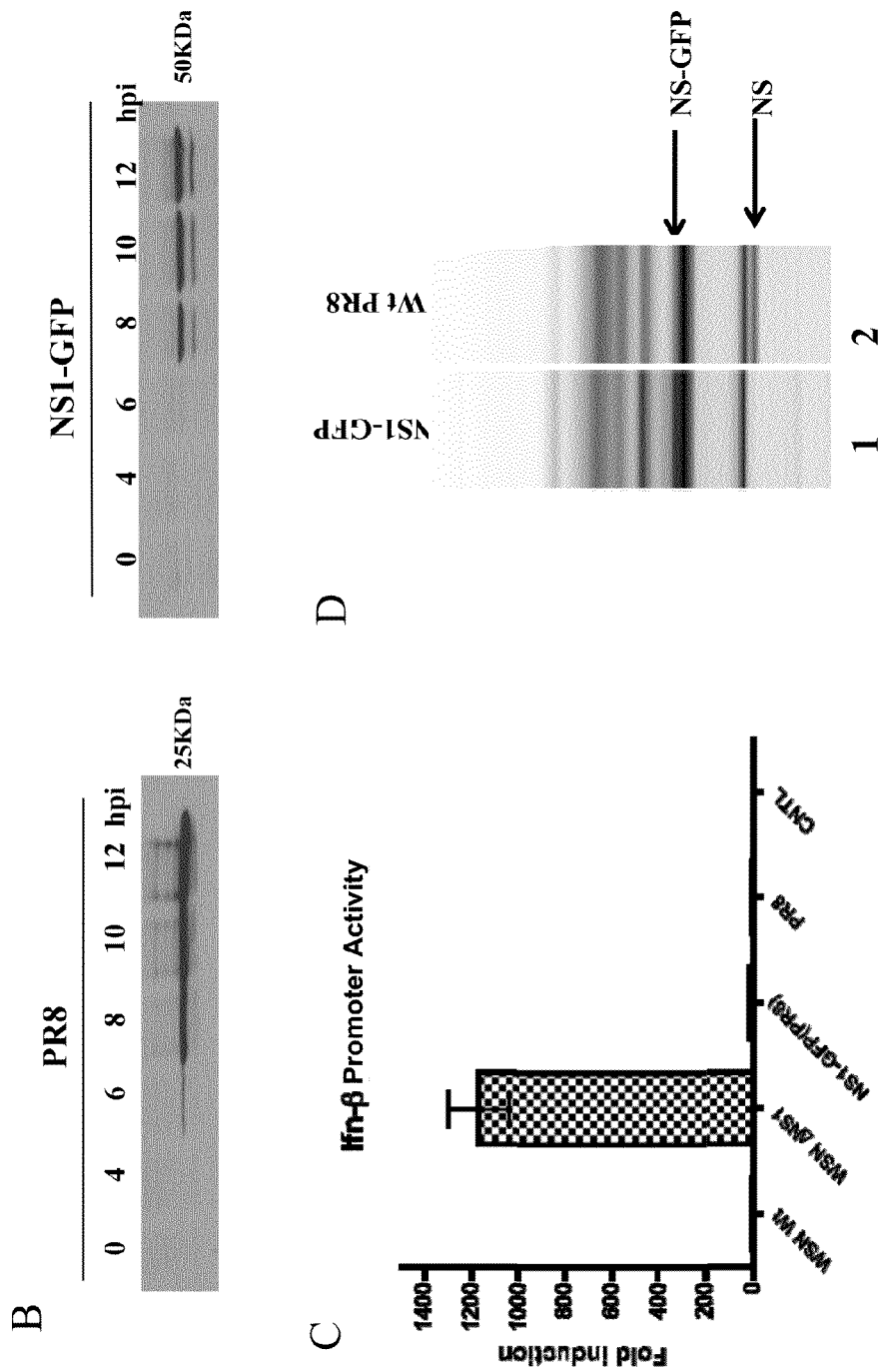

Next, the NS1 protein expression profile was examined in infected MDCK cells by western blot (FIG. 2B). In the Wt PR8 infected cells, NS1 expression can be seen as early as 6 hpi. However, in NS1-GFP virus-infected cells, NS1-GFP expression could be detected only after 8 hpi, again indicating slightly slower replication kinetics.

NS1-GFP Virus Suppress Interferon-β Promoter Activation.

One of the well-characterized functions of influenza A virus NS1 protein is the suppression of interferon-β induction via IRF-3 activation (Kochs et al., 2007, "Multiple anti-interferon actions of the influenza A virus NS1 protein," J Virol 81(13):7011-7021). Therefore, this antagonist function of NS1 was examined to find out if it is intact in the NS1-GFP virus. MDCK cells stably expressing firefly luciferase under the control of the interferon-β promoter were infected with either Wt PR8 or NS1-GFP virus at a MOI=1. Cell lysates were analyzed for firefly luciferase activity at 18 hpi as an indirect measure of IFN-β promoter activity. If the NS1-GFP virus is defective in blocking IFN-β promoter induction higher luciferase activity would be detected. However, if the NS1 function of the NS1-GFP virus is intact, the luciferase activity in NS1-GFP virus infected cells will be similar to Wt PR8 infected cells. An influenza virus carrying a deletion of NS1 (WSN ΔNS1) was used as a positive control. From FIG. 2C, it is apparent that the luciferase activity in NS1-GFP virus infected cells is similar to uninfected cells (control) indicating that NS1-GFP virus is fully competent in blocking IFN-β induction similar to Wt PR8 virus. As expected, WSN ANSI infected cells showed nearly a 1000-fold activation of IFN-β promoter. These results show that fusion of GFP to NS1 did not affect NS1 function.

NS-GFP Segment is Efficiently Packaged in the Virions.

Incorporation of viral genomic RNA in the progeny virions is one of the critical and highly orchestrated processes in the virus life cycle. The efficiency of incorporation will directly affect the infection efficacy of progeny virions. Although previous studies have shown that the 3' and 5' end of the genomic RNA are critical and sufficient for packaging of a segment, it is still unclear if increasing the length will affect the efficiency of incorporation (Marsh, G. A., R. Rabadan, A. J. Levine, and P. Palese. 2008. Highly conserved regions of influenza a virus polymerase gene segments are critical for efficient viral RNA packaging. J Virol 82:2295-304, Muramoto, Y., A. Takada, K. Fujii, T. Noda, K. Iwatsuki-Horimoto, S. Watanabe, T. Horimoto, H. Kida, and Y. Kawaoka. 2006. Hierarchy among viral RNA (vRNA) segments in their role in vRNA incorporation into influenza A virions. J Virol 80:2318-25). Given that the NS segment of NS1-GFP virus is nearly twice the size of Wt NS segment, the efficiency of incorporation of the NS-GFP segment into the virions was examined. The levels of NS segment in NS1-GFP and Wt PR8 virus were analyzed using a RNA 6000 Nano Chip (Agilent Technologies). Analysis of NS1-GFP vRNA, showed an NS segment appearing at a size of approximately 1800 bases (FIG. 2D, Lane 1). In the Wt PR8 vRNA, the NS segment appeared around the length of 900 bases, corresponding to the size of Wt NS segment (Lane 2). No significant difference in the incorporation of other viral segments was observed.

In Vivo Characterization of NS1-GFP Virus.

NS1-GFP Virus Causes Significant Pathogenicity in Mice.

Figures 3A, 3B:
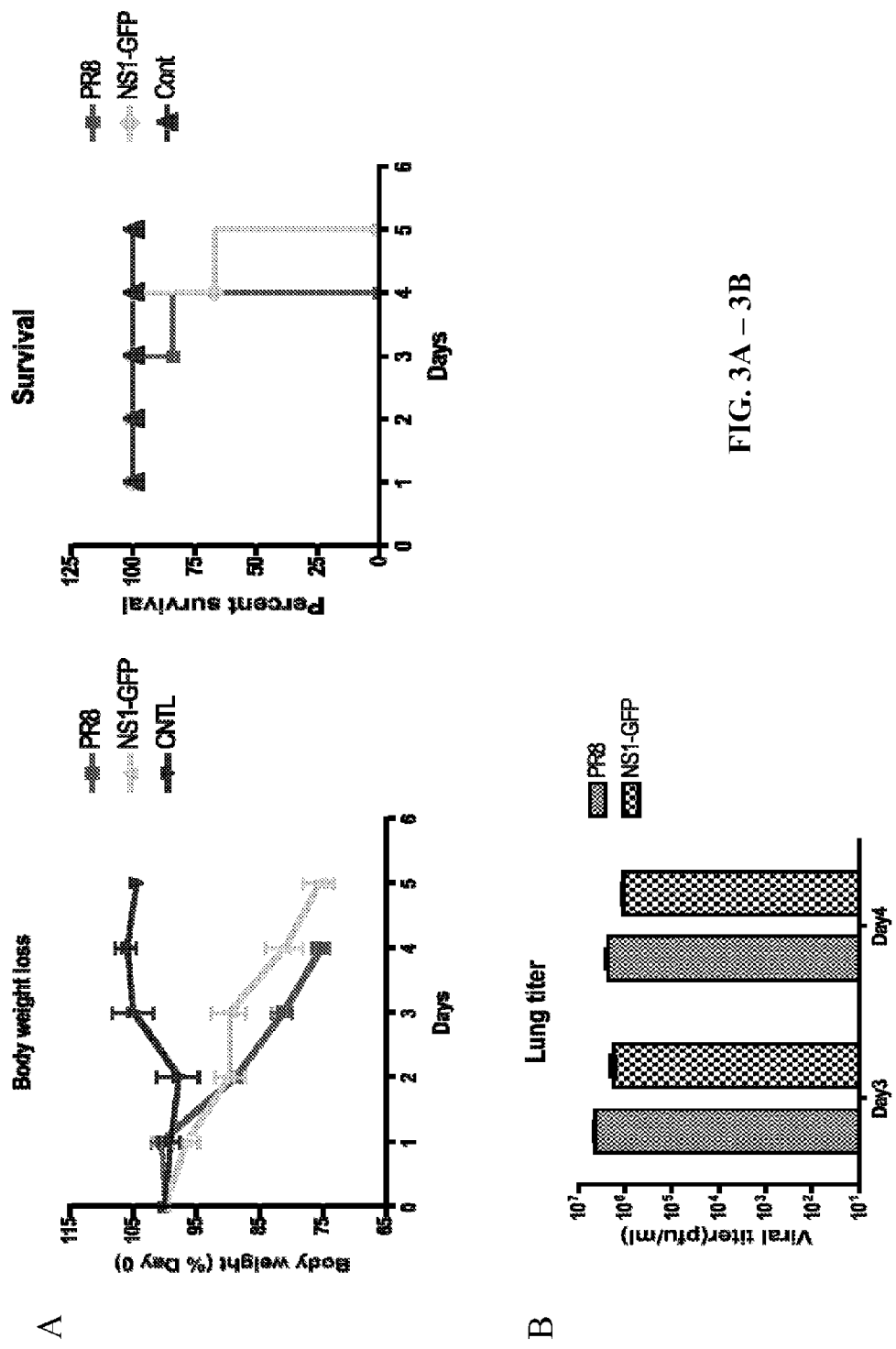

Wt PR8 virus has been previously shown to cause severe pathogenicity in mice. To test if the NS1-GFP virus is comparable in pathogenicity to its parental PR8 virus, 5-6 weeks old, female BalB/C mice (n=5/group) were infected intranasally with either NS1-GFP or Wt PR8 virus at a dose of $10^4$ pfu, and body weight loss and survival were monitored as a measure of pathogenicity (FIG. 3A). Mice showing more than 20% of body weight loss were considered to have reached the experimental end point and were euthanized. As expected Wt PR8 infected mice started showing significant weight loss at 2 dpi. NS1-GFP virus infected mice also showed significant weight loss with slightly delayed kinetics. Also, NS1-GFP virus infected mice succumbed to infection 1 day later than Wt PR8 infected mice. These data suggest that NS1-GFP virus infection causes severe pathogenicity in mice at levels comparable to Wt PR8 virus. Next, the levels of viral replication in the lungs of infected mice on day 3 and day 4 post-infection was examined (FIG. 3B). In infected mice, the NS1-GFP virus replicated very efficiently and grew to nearly $5 \times 10^6$ pfu/ml, which is slightly lower than Wt PR8 (2-fold lower). These results suggest that the insertion of GFP into the influenza A virus genome does not affect its in vivo phenotype.

Ex Vivo Imaging of NS1-GFP Replication in the Lungs of BalB/C Mice.

Figures 3C, 3D:
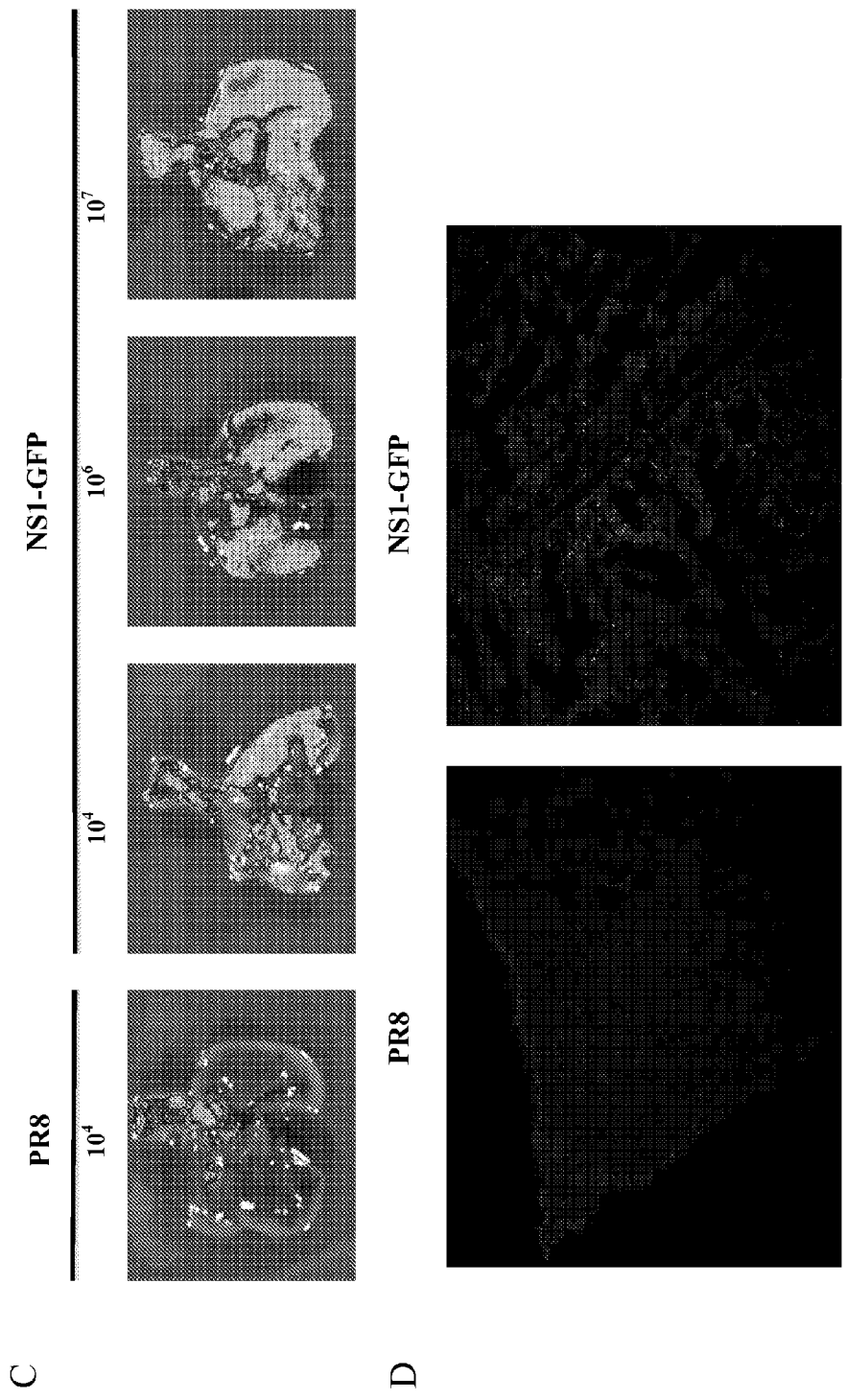

In order to visualize GFP expression in the lungs of infected mice, the mice were imaged using an IVIS-200 series system (Xenogen Corporation). Five-week old Balb/C mice were infected with Wt PR8 ($10^4$ pfu) or NS1-GFP virus with different doses ($10^4$, $10^6$ and $10^7$ pfu). Wt PR8 infected mice were used as controls for background fluorescence. Unfortunately, background fluorescence precluded an in depth analysis of GFP in the lung (in vivo) following virus infection (data not shown). To overcome this, the lungs were excised from euthanized mice and imaged ex vivo using the IVIS system (FIG. 3C) on day 4 post infection. From FIG. 3C, it is apparent that the level of fluorescence from the lungs of NS1-GFP virus infected mice is significantly higher than the one obtained from mice infected with WT PR8 virus (background), indicating active replication of GFP virus in the lungs of infected mice. A nice correlation between amount of virus inoculum and fluorescence from NS1-GFP virus infected lungs was observed, with fluorescence intensity increasing as the dose of inoculum increased. In addition, examination of cryosections of NS1-GFP virus infected lungs also showed infected cells expressing NS1-GFP protein (FIG. 3D). Taken together, these results demonstrate that the insertion of GFP into the influenza A virus genome does not seem to grossly affect its in vivo phenotype.

Kinetics of NS1-GFP Virus Infection in Mice.

Figures 4A, 4B:
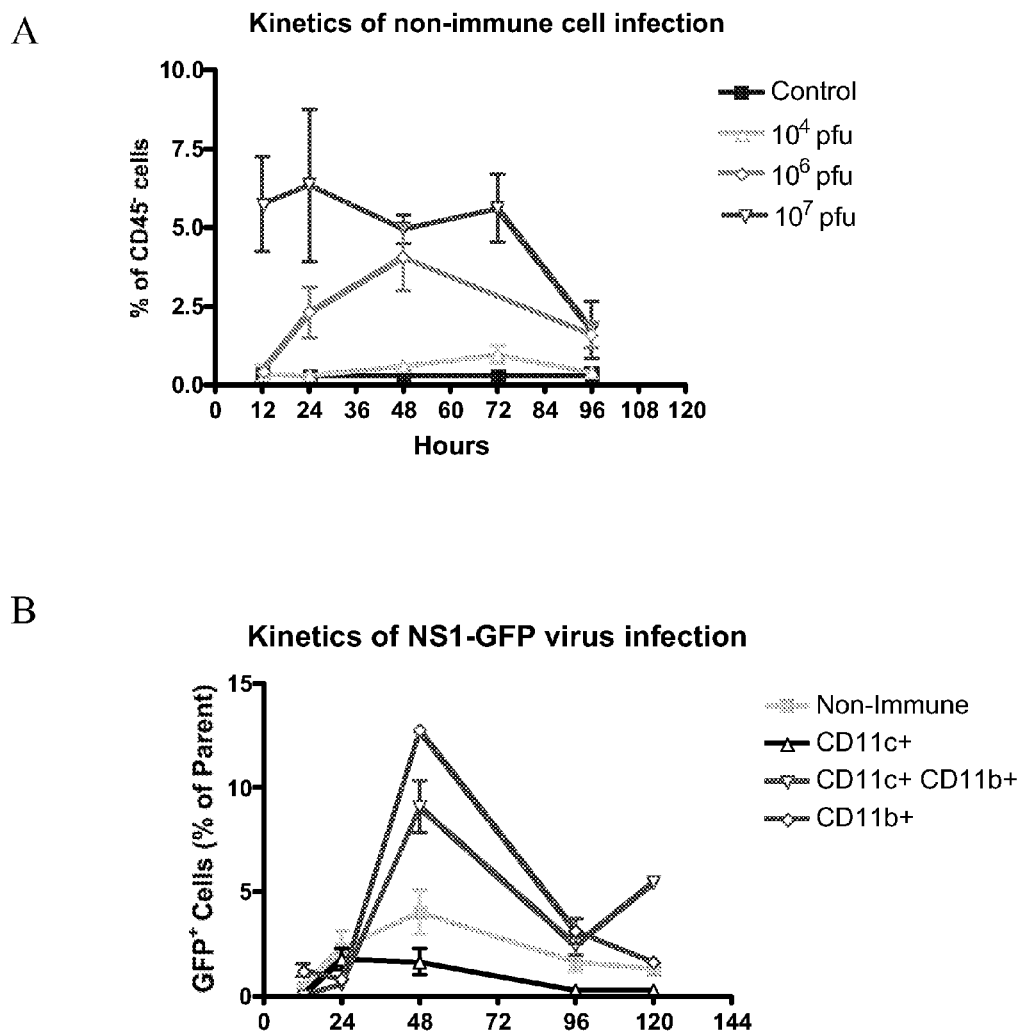

Previous studies have shown that influenza virus infects both immune and non-immune cells. To understand the in vivo dynamics of influenza virus infection progression and to identify the cells types susceptible to influenza infection, Balb/C mice were infected with NS1-GFP virus and then analyzed for GFP positive cells in the lung homogenates. The different cell populations in the lung homogenates were analyzed by multicolor flow cytometry using a BD LSR II flow cytometer. To find the minimal viral dose that would allow us to follow the kinetics of infection, mice were infected intranasally with NS1-GFP virus at three different doses ($10^4$, $10^6$, and $10^7$ pfu) and infection of non-immune cells (CD45$^-$) were analyzed at different times post-infection (FIG. 4A). Similar to results from ex vivo imaging, flow cytometric analysis of lung homogenates showed an increase in the number of infected cells as the NS1-GFP viral inoculum increased. Although, $10^4$ pfu of NS1-GFP virus caused a lethal infection in mice, the number of GFP positive cells were only 1-2 fold higher than background levels (~0.5%), suggesting that the detection limits of GFP positive signal was near (FIG. 3A; 4A). However, those infected with $10^6$ and $10^7$ pfu showed a clearer kinetics of infection of non-immune cells. The number of GFP positive cells peaked between 24-48 hpi followed by a decrease in the number of GFP positive cells. This decrease in GFP positive cells coincided with infiltration of immune cells and possibly partial clearance of virus-infected cells. Based on these data subsequent experiments were performed with a dose of $10^6$ pfu.

To follow the early kinetics of influenza infection in mice, BALB/c mice were intranasally inoculated with $10^6$ pfu of NS-GFP virus and the lung homogenates were analyzed for GFP expressing cells using commercial antibodies specific for cell surface markers, at 12, 24, 48, 72, and 120 hpi (FIG. 4B). At early time points, GFP expression was observed in only CD45$^-$ epithelial cells (12 hpi) suggesting that these cells are the primary targets of influenza virus infection. The peak infection of these cells occurred around 24-48 hrs post infection. In the immune cells, significant GFP expression was seen only after 24 hpi and the number of GFP containing cells peaked at 48 hpi. NS1-GFP was detected in CD11c$^+$ (alveolar macrophages, CD103$^+$ migratory dendritic cells (DC's)) CD11c$^+$ CD11b$^+$ (conventional dendritic cells) and CD11b$^+$ (monocytes and neutrophils) cells, which play important roles in viral clearance and the mounting of an adaptive immune response. Also, GFP expression was observed in both T and B cells, which likewise play a critical role in adaptive immunity (data not shown).

Effects of Oseltamivir Treatment on NS1-GFP Infection Progression.

Oseltamivir Treatment Restricts Viral Spreading.

Figure 5A:
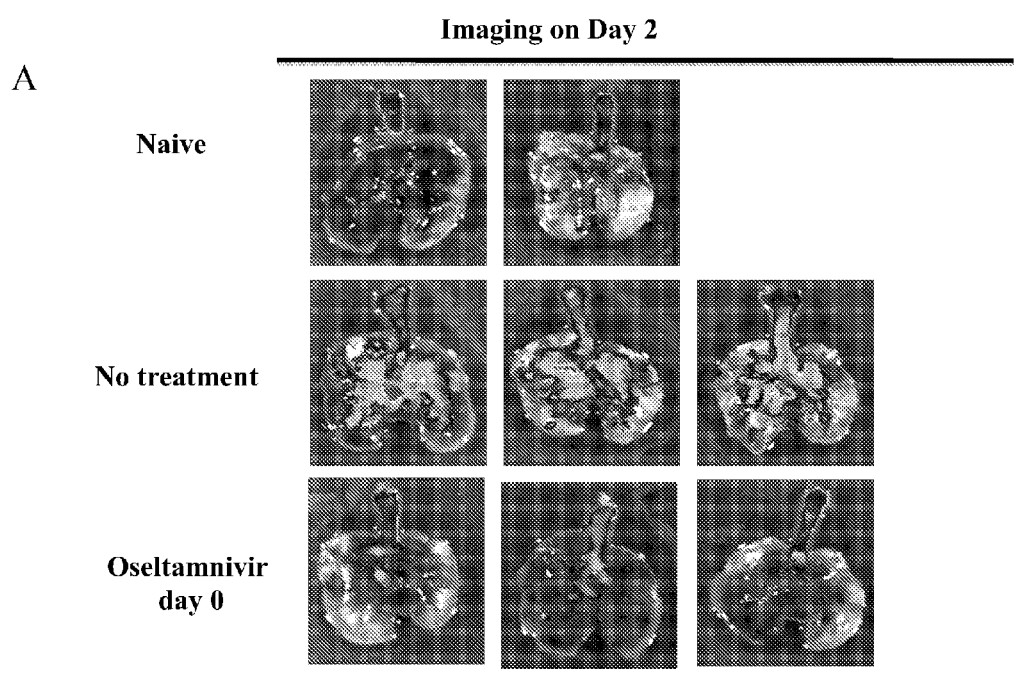
Figure 5B:
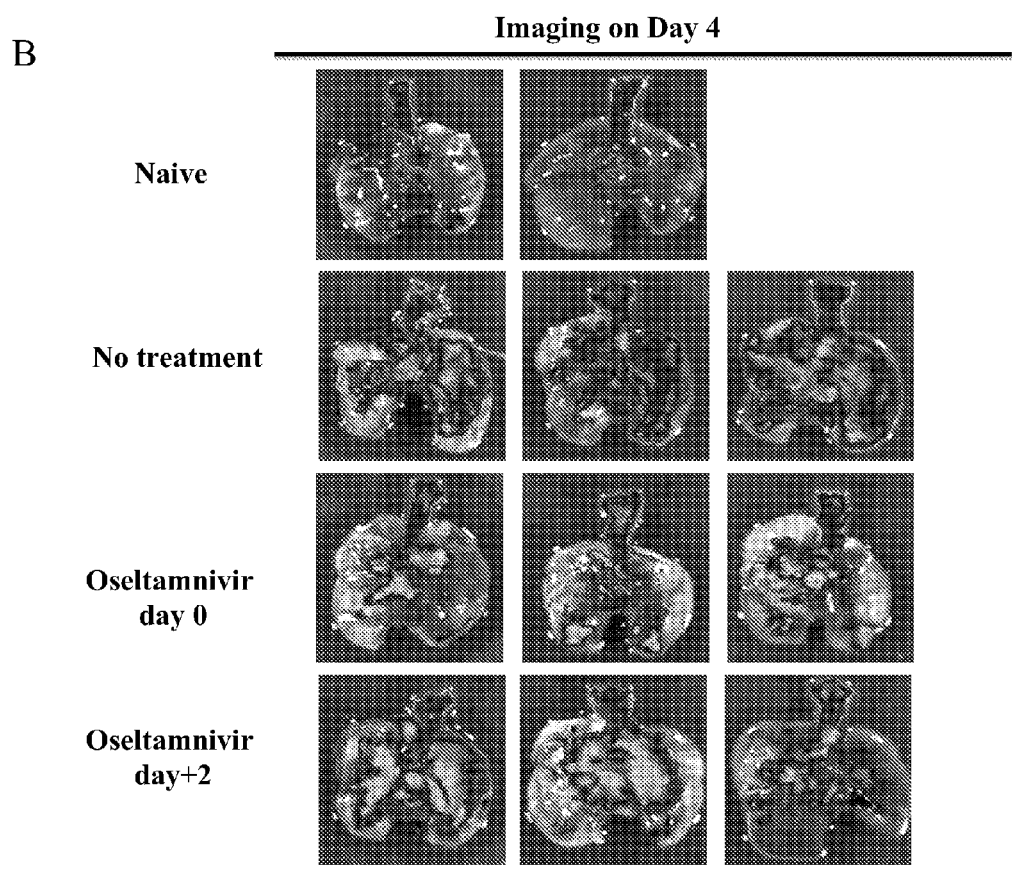

Oseltamivir phosphate, a viral neuraminidase inhibitor, is one of the widely used antivirals against influenza A virus. Oseltamivir controls influenza infection by preventing the release of progeny virions from the infected cell surface. Oseltamivir treatment has been shown to effectively protect against lethal influenza virus infection (Ilyushina, N. A., E. Hoffmann, R. Salomon, R. G. Webster, and E. A. Govorkova. 2007. Amantadine-oseltamivir combination therapy for H5N1 influenza virus infection in mice. Antivir Ther 12:363-70, Tumpey, T. M., A. Garcia-Sastre, A. Mikulasova, J. K. Taubenberger, D. E. Swayne, P. Palese, and C. F. Basler. 2002. Existing antivirals are effective against influenza viruses with genes from the 1918 pandemic virus. Proc Natl Acad Sci USA 99:13849-54). However, it is unclear how the oseltamivir treatment alters the progression of viral infection in vivo. To understand the mechanism by which oseltamivir treatment affects the progression of virus infection, mice were infected with $10^6$ pfu NS1-GFP virus and 50 mg/Kg of oseltamivir was administered once daily with treatments starting on day 0 or day 2 after infection. In order to observe the global effects of oseltamivir treatment, ex vivo analysis of whole lungs were performed using the IVIS-200 system (FIG. 5). The lungs from uninfected mice were used as controls for background fluorescence. Analysis of mice lungs on day 2 post-infection showed a clear difference in the fluorescence intensities between untreated mice and oseltamivir treated mice (FIG. 5A). In the untreated group, most of the GFP fluorescence signal was concentrated in areas close to large conducting airways. In the oseltamivir treated mice, with treatment starting on the day of infection (day 0), additional fluorescence near the large conducting airways was observed. However, fluorescence intensity was significantly lower than untreated mice (3 to 5 fold lower). Interestingly, analysis of the untreated group on day 4 post infection showed GFP fluorescence signal throughout the lung, demonstrating the progression of infection to the lower respiratory tract (FIG. 5B). However, oseltamivir treatment (starting on day 0) significantly restricted the spread of viral infection and the GFP signal was seen in localized spots. In contrast, when the treatment started two days (day+2) after infection, no significant difference in the GFP fluorescence signal in the lungs of "day+2" treated and the no treatment groups was observed. Even though GFP fluorescence signal in the "day+2" treatment group and the no treatment groups were similar on day 4 (48 hrs after starting treatment), it is very likely that prolonged treatment might protect the mice. Taken together, these results indicate that oseltamivir treatment restricts viral infection to the areas of initial infection and prevents spreading of virus in the lungs, and thereby facilitating efficient viral clearance.

Oseltamivir Treatment Lowers Infection of all Susceptible Cells.

To examine if oseltamivir treatment affects infection of any specific cell type, lung homogenates from treated and untreated mice were analyzed by multicolor flow cytometry. Mice were divided into 4 groups as follows: (1) Control (No infection/No treatment), (2) No treatment (infection/No treatment), (3) Day 0 (infection/treatment started on day of infection) and (4) Day+2 (infection/treatment started 2 days after infection). Mice were infected intranasally with $10^6$ pfu NS1-GFP virus and the flow cytometric analysis were carried out at 24, 48, 72, 96 and 120 hpi (FIG. 7). In the No treatment group mice, mostly epithelial cells were GFP positive at early periods of infection. At 48 hpi, along with epithelial cells, $CD11c^+$, $CD11c^+$ $CD11b^+$ and $CD11b^+$ immune cells were also GFP positive. Since most of the aforementioned immune cells take up antigens from the environment, it is likely that some of the GFP positive cells are not infected but are carrying debris of GFP positive cells. Further analysis by staining for other cell surface viral antigen (HA or M2) will help us differentiate infection versus antigen uptake. Interestingly, examination of other cell types involved in the innate and adaptive immune response revealed that a significant percent of infiltrating monocytes ($Ly6C^+$), B cells ($B220^+$) and NK cells ($NK1.1^+$) were GFP positive, indicating that these cells are targets of influenza infection (FIG. 7). In the "Day0" group, which received oseltamivir treatment starting from the day of infection, the numbers of GFP positive cells were significantly reduced in all the analyzed cell types. Although the numbers of $GFP^+$ cells were significantly reduced by oseltamivir treatment, GFP cells could even be detected on day 5 indicating low levels of localized infection. This is in agreement with the ex vivo imaging of lungs on day 4 (FIG. 6B) that showed small localized areas of GFP infection in the Day0 group. However, similar to ex vivo imaging data, oseltamivir treatment of mice starting on day 2 did not significantly alter the course of infection progression (Day+2 group).

Together, these data suggest that oseltamivir treatment greatly reduces influenza infection of both epithelial and immune cells, and infection is restricted to small-localized areas in the lung, which are likely the initial sites of infection.

6.3 Discussion

This example describes the successful generation of a complete influenza virus encoding a GFP reporter in its genome. The GFP reporter was introduced in the middle of NS segment to prevent any detrimental effect on vRNA packaging signals present in the 3' and 5' ends. Previous attempts to generate a complete GFP carrying virus have been unsuccessful due, at least in part, to the complication associated with expression of NS1/NEP, which are expressed by alternative splicing. To overcome this complication, splicing sites were mutated and NS1, GFP and NEP were expressed as a single fusion protein (NS1-GFP-2A-NEP). Here GFP was expressed as a fusion protein with NS1. NEP, which is essential for virus survival, gets separated from NS1-GFP protein by an autoproteolytic cleavage reaction at 2A site. Also, codon-optimized GFP seemed as though it might be important for successful rescue of stable GFP virus. Most of attempts made to rescue stable influenza virus carrying non-codon optimized version of a reporter gene have failed. This failure is may be due to the presence of internal splice sites (Not shown). In the NS1-GFP virus, all the visible viral plaques expressed GFP and grew up to titers of $5 \times 10^8$ pfu/ml in 9 day old eggs.

NS1-GFP virus, albeit slightly slower than Wt PR8 virus, showed efficient replication and NS1-GFP protein expression in MDCK cells (FIG. 2). Importantly, NS1-GFP virus was effectively able to suppress the induction of interferon-β promoter, demonstrating that fusion of GFP does not affect the NS1's function. Also, no significant differences the vRNA packaging the virions between Wt PR8 and NS1-GFP virus were observed.

In the mice infections experiments, NS1-GFP virus caused significant pathogenicity in mice, as assessed by body weight loss and survival. All mice infected with $10^4$ pfu NS1-succumbed to infection by day 5, just one day later than Wt PR8 virus. Also, NS1-GFP virus replicated efficiently in the lungs of infected mice. Interestingly, nearly 5-10% of the viruses in the mice lung homogenates and the supernatants of multicycle growth experiments were GFP negative, suggesting that these of viruses may carry deletions in the GFP. However, in repeated analysis of NS1-GFP virus stocks, GFP negative plaques were not found. It will be of interest to see if the GFP negative viruses arise, likely due to selection pressure, by deletion or mutation at specific regions of NS-GFP segment.

Ex vivo imaging of NS1-GFP infected mice revealed that GFP fluorescence signal is concentrated in areas closer to large conducting airways during the initial stages of infection, suggesting active replication of NS1-GFP virus in these region (FIG. 5A, No treatment). At the later stages GFP signal could be seen throughout the lung, indicating the spreading of virus deeper into the lower respiratory tract (FIG. 5B, No treatment; FIG. 3C). Treatment of infected mice with oseltamivir, starting on the day of infection, effectively blocked viral spreading. The virus replication or GFP signals were observed only in confined spots. However, starting oseltamivir treatment 2 days after infection did not significantly control the viral spreading. It should be noted the infectious dose used in the experiments is greater than 100 LD50 and the viral titers in the lungs peak by day 2. This may one of the likely reasons why oseltamivir treatment did not have any impact on viral replication at this stage.

Flow cytometric analysis of infected lung homogenates revealed the kinetics of influenza infection in different cell types. During the early stages of infection GFP expression was seen mostly in non-immune cells (12-24 hpi), indicating that these cells are the primary targets of influenza virus infection (FIG. 4; FIG. 6). After 24 hpi, GFP expression was detected in immune cells. A distinct pattern of NS1-GFP infection or susceptibility for different immune cells in the following order $CD11c^+$ $CD11b^+$>$Ly6C^+$>$CD11b^+$>$CD11c^+$ was observed. NS1-GFP was also present in B, T and NK cells (FIG. 6; Data not shown for T cells). In these cell types NS1-GFP levels peaked around 48 hrs. After 48 hrs, the number of GFP cells declined probably due the clearance of infected cells by the immune system. It is worthwhile noting that some of these cells actively take up foreign antigen and cell debris; so it is possible that some these cells are not infected but rather carry the debris of infected cells. Analysis of "day0" oseltamivir treated group showed a dramatically lowered numbers of infected cells. Oseltamivir treatment effectively reduced the infection in all the analyzed cell types. However, in the "day2" group, the numbers of GFP positive cells were similar to no treatment group, even after 48 hrs of oseltamivir treatment.

Using the same the strategy that was used to generate NS1-GFP virus, recombinant viruses carrying RFP and luciferase reporters have been generated (Data not shown). This clearly demonstrates that foreign genes (~up to 1 kb) can be inserted into the NS segment without grossly affecting the phenotype of the virus.

7. EXAMPLE 2

Analysis of In Vivo Dynamics of Influenza Virus Infection Using a GFP Reporter Virus

7.1 Introduction

In this example, using reverse genetics, a recombinant influenza A virus (IAV) carrying a GFP reporter in the NS segment (NS1-GFP virus) was generated. This is the first demonstration of the successful generation of a mouse-lethal IAV expressing a fluorescent protein. Despite some attenuation, the NS1-GFP virus replicates efficiently in eggs, MDCK cells and in mouse lungs. The in vivo dynamics of IAV infection progression in mice was characterized and different cell types that are susceptible to influenza virus infection were identified. Whole organ imaging of NS1-GFP virus infected lungs was consistent with IAV infections starting in the respiratory tract near the trachea and main stem bronchi, spreading with time into bronchioles. Also, two well-known antivirals, amantadine and oseltamivir, which block virus uncoating and virus spreading, respectively, were tested. By visualizing the in vivo targets of IAV infection and the dynamics of infection progression, a better understanding of IAV pathogenesis has been gained. In addition, a replication-competent IAV expressing GFP will serve as an important tool to analyze the impact in vivo of different vaccine strategies, immune modulators and antivirals against IAV.

7.2 Materials and Methods

Cell Lines

Human embryonic kidney (293T) cells were maintained in DMEM supplemented with 10% FBS and 1000 u/ml penicillin/streptomycin. Madin-Darby canine kidney (MDCK) cells were maintained in MEM supplemented with 10% FBS and penicillin/streptomycin. Reagents for cell culture were purchased from Gibco Life Technologies.

Construction of NS-GFP Segment

The NS segment (A/Puerto Rico/8/34) carrying GFP was generated by overlapping fusion PCR using standard molecular biology techniques. Briefly, the NS1 ORF without the stop codon was fused to the N-terminal of a codon-optimized maxGFP (Amaxa) via a GSGG (SEQ ID NO:14) linker region (NS1-GFP). The maxGFP was followed by a short GSG linker, a 19aa 2A autoproteolytic site (ATNFSLLKQAGDVEENPGlP) (SEQ ID NO:20) (12) derived from porcine teschovirus-1 and by the NEP ORF (FIG. 1A). Also, silent mutations in the endogenous splice acceptor site in the NS1 ORF were introduced to prevent splicing (11). The engineered NS-GFP segment was cloned in the pDZ IAV rescue plasmid (13).

Plaque Assay:

MDCK cells were seeded in 6-well plates, a day prior to infection, at a dilution of $10^6$ cells/well. Next day, the cells were washed once with 2 ml PBS and incubated with virus diluted in 200 µl of PBS containing 0.3% bovine albumin and 1000 p/ml penicillin/streptomycin (PBS/BA; MP biochemicals) for 1 h at 37° C. with frequent shaking. After incubation, the virus inoculum was removed and overlaid with MEM containing a 0.6% oxoid agar and 1 µg/ml TPCK treated trypsin (Sigma). The plaques were visualized by staining with crystal violet.

Rescue of NS1-GFP Virus

NS1-GFP virus (A/Puerto Rico/8/34 background) was rescued using standard reverse genetics techniques (2). Briefly, 0.5 µg of each of 8 pDZ plasmids representing the 8-segments of Influenza A virus (IAV) genome were transfected into 293T cells using Lipofeactmine™2000 (Invitrogen). After 24 h, the 293T cells were resuspended in the media and 100 µl of the mix was injected into 8-day old eggs. The NS1-GFP virus was harvested from the allantoic fluid at 48 hpi. The successful rescue of virus were confirmed by performing haemagglutination (HA) assay with chicken red blood cells. After plaque purification, NS1-GFP virus was amplified in 9-day old embryonated eggs. The sequence of the NS-GFP segment in the NS1-GFP virus was confirmed by RT-PCR and sequencing. The titers of viral stocks were determined by plaque assay in MDCK cells.

Single Cycle and Multi-Cycle Growth Curve:

MDCK cells were seeded at a dilution of $10^6$ cells/well in 6-well plates, a day prior to infection. The cells were washed with 2 ml of PBS and incubated with $10^3$ pfu virus (single-cycle) or $10^6$ pfu (multi-cycle) virus diluted in 200 µl of PBS/BA. After incubation for 1 hr at 37° C. with frequent shaking, the virus inoculum was removed and 3 ml of MEM containing 0.3% BA and 1 µg/ml TPCK treated trypsin was added. At indicated times, nearly 300 µl of supernatant was removed for virus titration and replenished with same amount of fresh media. The viral titers were determined by plaque assay.

Immunostaining

A549 cells were infected with NS1-GFP virus at a MOI=1. At 10 hpi, the cells were washed with PBS and fixed in 1 ml of 4% formaldehyde (methanol-free) for 10 min. After permeabilization with 0.5% Triton X-100 in PBS, the cells were stained in PBS containing 2% BSA with a rabbit polyclonal anti-NP antibody. The cells were washed twice PBS and stained with anti-rabbit secondary antibody conjugated to Alexa-588 (Invitrogen). Images were acquired on an Olympus XI-70 microscope at 20× using Q-Capture software.

Western Blot Analysis

MDCK cells in 6-well plates were infected at a MOI=1 and cells were lysed using 1% Triton X-100 lysis buffer (50 mM Tris-HCl [pH 7.5], 150 mM NaCl, 5 mM EDTA, 1% Triton X-100, and protease inhibitors) at the indicated times post-infection. The protein samples were subjected to sodium dodecyl sulfate-polyacrylamide gel electrophoresis (SDS-PAGE) and transferred to a polyvinylidene difluoride membrane. Wt NS1 and NS1-GFP levels were assessed by immunoblotting with a rabbit polyclonal anti-NS1 antibody raised against the N-terminal 1-73 amino acids of NS1 from A/Swine/Texas/4199-2/98 (dilution 1:3,000) followed by a anti-rabbit secondary antibody (dilution 1:10,000) conjugated to HRP (GE Healthcare Life Sciences).

Interferon-β Promoter Induction Assay

MDCK cells stably expressing firefly luciferase under the control of the human interferon-β (IFN-β) promoter were infected with a MOI=1. At 18 hpi, the cells were washed with 2 ml of PBS and lysed in 200 µl of cell culture lysis reagent (Promega). The luciferase activity in 100 µl of cell lysate was measured with a firefly luciferase assay kit (Promega). Each experiment was done in triplicates and repeated at least three times.

Mice Experiments

All animal procedures performed were in accordance with Institutional Animal Care and Use Committee (IACUC) guidelines, and approved by the IACUC of Mount Sinai School of Medicine.

Body Weight Loss and Survival

Female BALB/c mice (5-6 weeks old) were anesthetized with ketamine-xylaxine and intranasally infected with the indicated virus dose diluted in 50 µl of PBS. Body weight and survival were measured daily. Mice showing more than 25% of body weight loss were considered to have reached the experimental end point and were humanely euthanized.

Determination of $LD_{50}$

Female BALB/c mice (6 weeks old) were anesthetized with ketamine-xylaxine and intranasally infected with PR8 or NS1-GFP virus in 50 µl at indicated doses (n=5 per group). The mice were monitored daily for survival and body weight loss over a period of 14 days. Mice showing more than 25% of body weight loss were considered to have reached the experimental end point and were humanely euthanized. $LD_{50}$ values were calculated by the Reed & Muench method (3).

Lung Titers

Lungs of infected mice were excised on days 3 and 4 post-infection and homogenized in 1 ml of PBS/BA, using a mechanical homogenizer. The viral titers in the homogenates were quantified by plaque assay on MDCK cells. Each data point represents the average titer from 3 mice.

Cryosections of Lungs

After surface cleaning with PBS, mice lungs were placed in OCT media and slowly frozen in −80° C. The lung sections of 5 µm thickness were cut using a cryostat and placed on a glass slide. The sections were fixed in 200 µl of PBS containing 4% formaldehyde for 10 min and washed twice with PBS. The nuclei were stained with DAPI. Images were acquired on an Olympus XI-70 microscope at 10× using Q-Capture software.

Ex Vivo Imaging of Lungs

The lungs of infected mice were excised at indicated times post infection. After cleaning the surface with PBS, the lungs were placed on a glass plate and imaged using the IVIS-200 series imaging system (Xenogen Corporation) fitted with GFP excitation/emission filters at 4 s exposure time.

Antiviral Treatments

Mice were treated with either 50 mg/Kg of oseltamivir phosphate in PBS (Roche Laboratories, NJ) or 40 mg/Kg of amantadine hydrochloride in $H_2O$ (Sigma), administered by oral gavage (24). The treatments were started 1 h post-infection and were given once daily until the end of the experiment.

Flow Cytometry

Single Cell Preparation

Single cell suspensions of mice lung were prepared using collagenase/DNase treatment. Briefly, excised whole lungs were minced in 10 ml of DMEM containing 10 mM HEPES, 5% FBS, 100 u/ml Type IV Collagenase (Worthington) and 100 µg/ml DNase I (Roche), and incubated at 37° C. for 30 min. The tissue pieces were meshed through a 70 µm cell strainer. The cells were washed once with HBSS containing 10 mM HEPES buffer, 2% FBS and 2 mM EDTA followed by filtration using a 40 µm cell strainer. The red blood cells in the preparation were lysed using 1 ml of ACK lysis buffer (Lonza). The cells were pelleted and washed once with HBSS.

Staining and Analysis Cell Surface Markers

Approximately $1 \times 10^6$ cells were stained in 100 µl of HBSS (10 mM HEPES, 2% FBS, 2 mM EDTA) using commercially available antibodies in the presence of Fc receptor blocking antibody (2.4G2) for 30 min on ice. The monoclonal antibodies conjugated to different fluorochromes (PerCP-Cy5.5, APC, APC-CY7, Pacific blue, PE, PE-Cy7) were purchased form BD biosciences and Ebioscience. The antibody clones used in cell surface staining were Fc block (2.4G2), CD45 (30-F11), CD11c (HL3), CD11b (M1/70), CD4 (GK1.5), CD8a (53-6.7), Gr1 (RB6-8c5), B220 (RA3-6B2), Pan NK (DX5) and MHCII (M5/11.15.2). After 30 min incubation, the cells were washed twice with HBSS buffer and either used directly for flow cytometry or for intracellular staining.

Intracellular Staining

After staining for cell surface markers, the cells were fixed and permeabilized in 100 µl BD Cytofix/Cytoperm solution for 30 min. The cells were washed a twice with BD Perm/Wash buffer and stained anti-NP monoclonal antibody conjugated with Alexa-532 fluorophore and anti-GFP polyclonal antibody conjugated with Alexa-488 fluorophore (Evorgen). After incubation for 30 min on ice, the cells were washed three times with BD Perm/Wash buffer and once with HBSS/2% FBS buffer.

Flow cytometry was performed on a BD LSR11 using FACSDiva software (BD Biosciences). The data were analyzed using FlowJo Software (Tree Star Inc.)

7.3 Results

Generation of IAV Expressing GFP

Figures 7A, 7B, 7C:
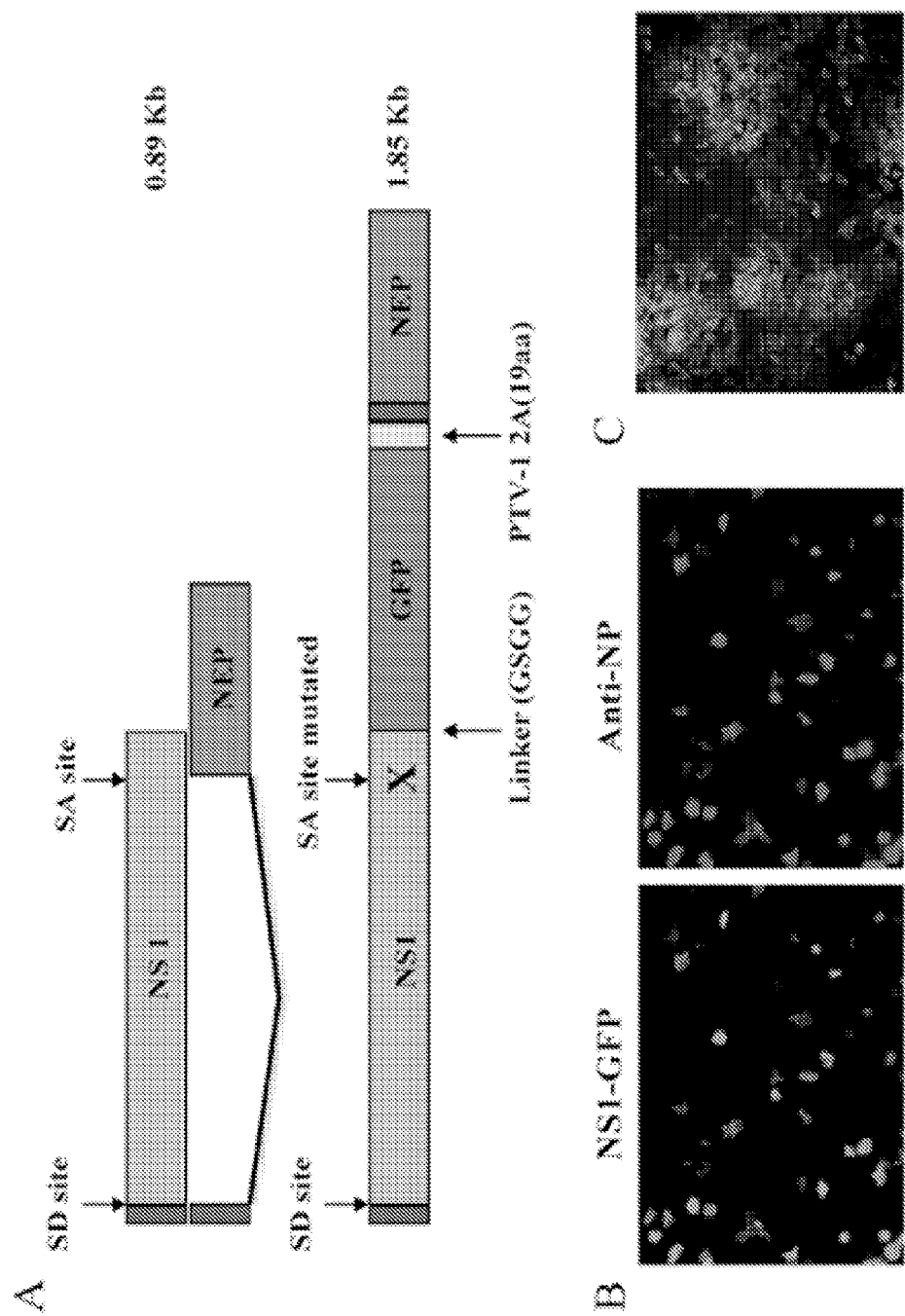

The NS segment of influenza A virus (IAV) encodes two proteins: NS1 produced from unspliced mRNA and NEP produced from spliced mRNA (FIG. 7A). Here, the NS segment was modified to express NS1-GFP and NEP as a single polyprotein with a 19aa porcine teschovirus-1 (PTV-1) 2A autoproteolytic cleavage site between them, allowing NEP to be released from the upstream NS1-GFP protein during translation (11, 12). Also, two silent mutations in the splice acceptor site were introduced to prevent splicing of NS mRNA (11). The NS1-GFP virus was rescued using standard reverse genetics techniques as previously described (13). Although the initial rescue supernatant contained a mixture of both GFP positive and GFP negative virus populations, a stable GFP carrying clone was isolated after three rounds of plaque purification. In order to test if GFP was expressed in all infected cells, A549 cells were infected with the NS1-GFP virus at a MOI=1 and stained for the viral nucleoprotein (NP), a viral protein critical for replication (FIG. 7B). At 10 hours post-infection (hpi), NS1-GFP expression was observed in all cells expressing NP (infected cells), demonstrating that GFP is expressed in all infected cells (FIG. 7B). Additionally, NS1-GFP virus was capable of undergoing multiple rounds of replication and formed visible GFP expressing plaques (FIG. 1C), and grew to titers of $5 \times 10^8$ pfu/ml in 9-day old embryonated eggs. The quality of the NS1-GFP virus preparation was further determined by examining GFP expression in 20 randomly selected visible plaques. Only preparations in which all 20 plaques were GFP positive were used in further experiments.

In Vitro Characterization of NS1-GFP Virus

NS1-GFP Virus Replicates in MDCK Cells.

Figures 8A, 8B, 8C:
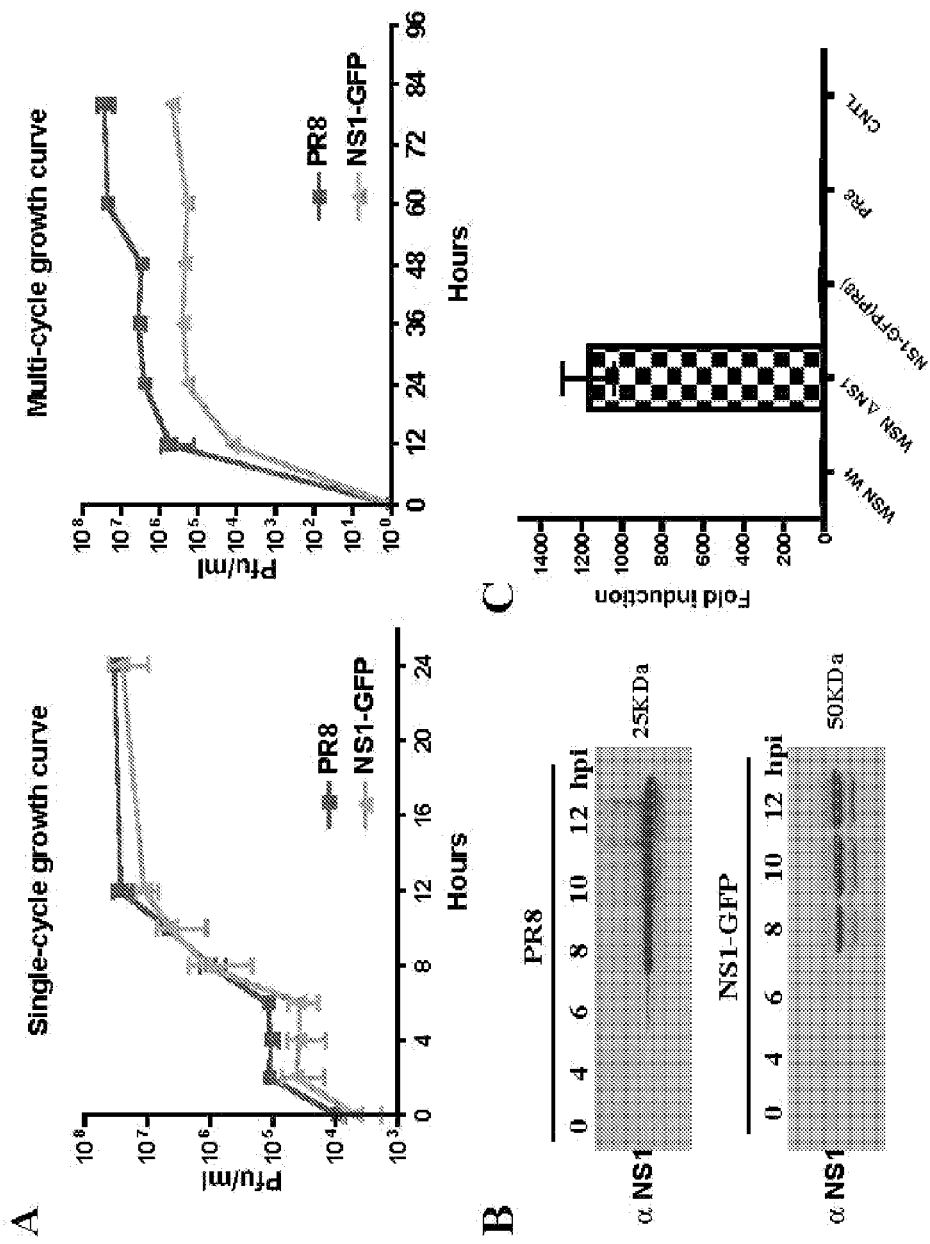

To test if the presence of a longer NS segment in NS1-GFP virus, which is approximately twice the size of the Wild type PR8 (Wt PR8) NS segment (1.89 kb vs. 0.89 kb), affects the virus replication cycle in tissue culture, the growth kinetics of NS1-GFP virus and parental virus Wt PR8 in MDCK cells were compared (FIG. 8A). MDCK cells were infected with either NS1-GFP or Wt PR8 virus at MOI of 1 or of 0.001 and at various time points after post infection, the viral titers in the supernatant were quantified by plaque assay. In a single cycle replication assay (MOI=1), NS1-GFP virus showed growth patterns similar to Wt PR8 virus with titers reaching up to $2 \times 10^7$ pfu/ml. However, in a multi-cycle replication assay (MOI=0.01), NS1-GFP virus showed a slight delay in replication kinetics with titers reaching up to $4 \times 10^5$ pfu/ml. This indicates that NS1-GFP virus can undergo multicycle replication in MDCK cells, albeit reaching approximately 100-fold lower titers than Wt virus.

Next, the NS1 protein expression profile was examined in infected MDCK cells by western blot analysis (FIG. 8B). In the Wt PR8 infected cells, NS1 expression was seen as early as 6 hpi. In NS1-GFP virus-infected cells, NS1-GFP expression was detected at the earliest by 8 hpi, suggesting a modest delay in NS1-GFP expression.

NS1-GFP Virus Suppresses IFN-β Promoter Activation.

A well-characterized function of IAV NS1 protein is the suppression of IFN-β promoter induction via IRF-3 activation (14). It was therefore examined whether this antagonist function of NS1 is intact in the NS1-GFP virus. MDCK cells stably expressing firefly luciferase under the control of the IFN-β promoter were infected with either Wt PR8 or NS1-GFP virus at a MOI=1. An IAV carrying a deletion of NS1 (WSN ΔNS1) was used as a positive control. The cell lysates were analyzed for firefly luciferase activity at 18 hpi as an indirect quantification of IFN-β promoter activity. The luciferase activity in NS1-GFP virus infected cells was found to be similar to PR8 infected cells, suggesting that the NS1-GFP virus is capable of blocking IFN-β induction as efficiently as Wt PR8 NS1 (FIG. 8C). In contrast, WSN ΔNS1 virus, which lacks the ability to block IFN-β induction, infected cells showed nearly a 1200-fold activation of IFN-β promoter. These results show that the NS1-GFP virus is competent in blocking the induction of IFN-β promoter during IAV infection.

In Vivo Characterization of NS1-GFP Virus

NS1-GFP Virus Causes Significant Pathogenicity in Mice.

Figures 9A, 9B:
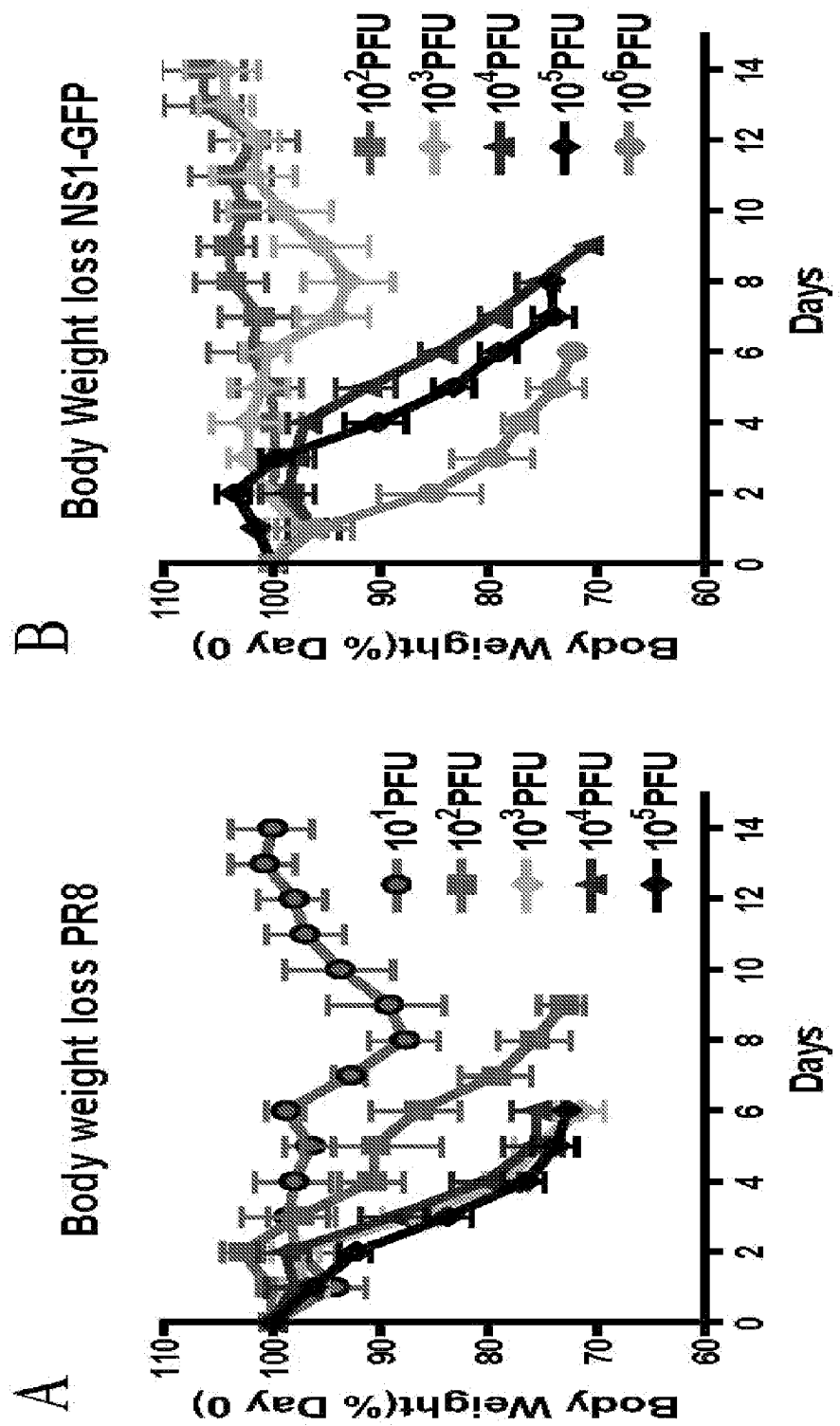
Figures 10A, 10B:
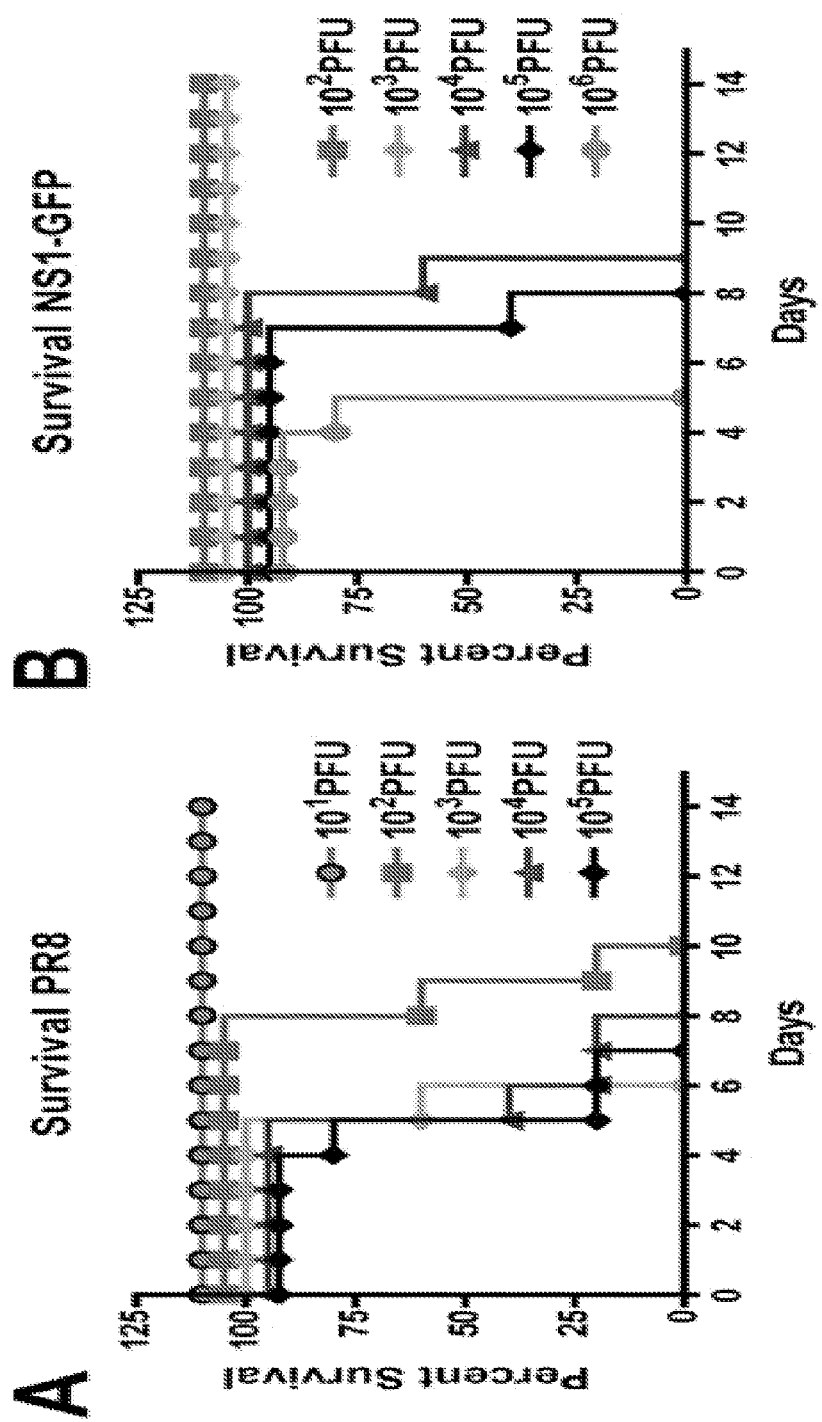

Wt PR8 has been previously shown to cause severe pathogenicity in mice (11, 15). To test if the NS1-GFP virus is comparable in disease induction to its parental virus, BALB/c mice were infected intranasally with either NS1-GFP or Wt PR8 virus at different doses, and body weight loss and survival were measured (FIG. 9; FIG. 10A-B). In the Wt PR8 infected mice, all mice infected with a dose $10^2$ pfu or higher showed significant weight loss starting 2 dpi and all mice succumbed to infection by day 10 (FIG. 9A, FIG. 10A). In the NS1-GFP virus infected mice, only mice that received $10^4$ pfu or higher showed significant weight loss and all of them lost more than 25% body weight by day 9 and were humanely euthanized (FIG. 9B; FIG. 10B). This indicates that NS1-GFP virus is attenuated compared to PR8 virus. Based on the survival data, the $LD_{50}$ value for NS1-GFP virus was determined to be 3160 pfu, around 100-fold higher than parental PR8 virus (31.60 pfu)(16). Despite the attenuation of the NS1-GFP virus in vivo, it is still possible to use a lethal dose of this virus in the mouse model.

Figures 10C, 10D, 10E:
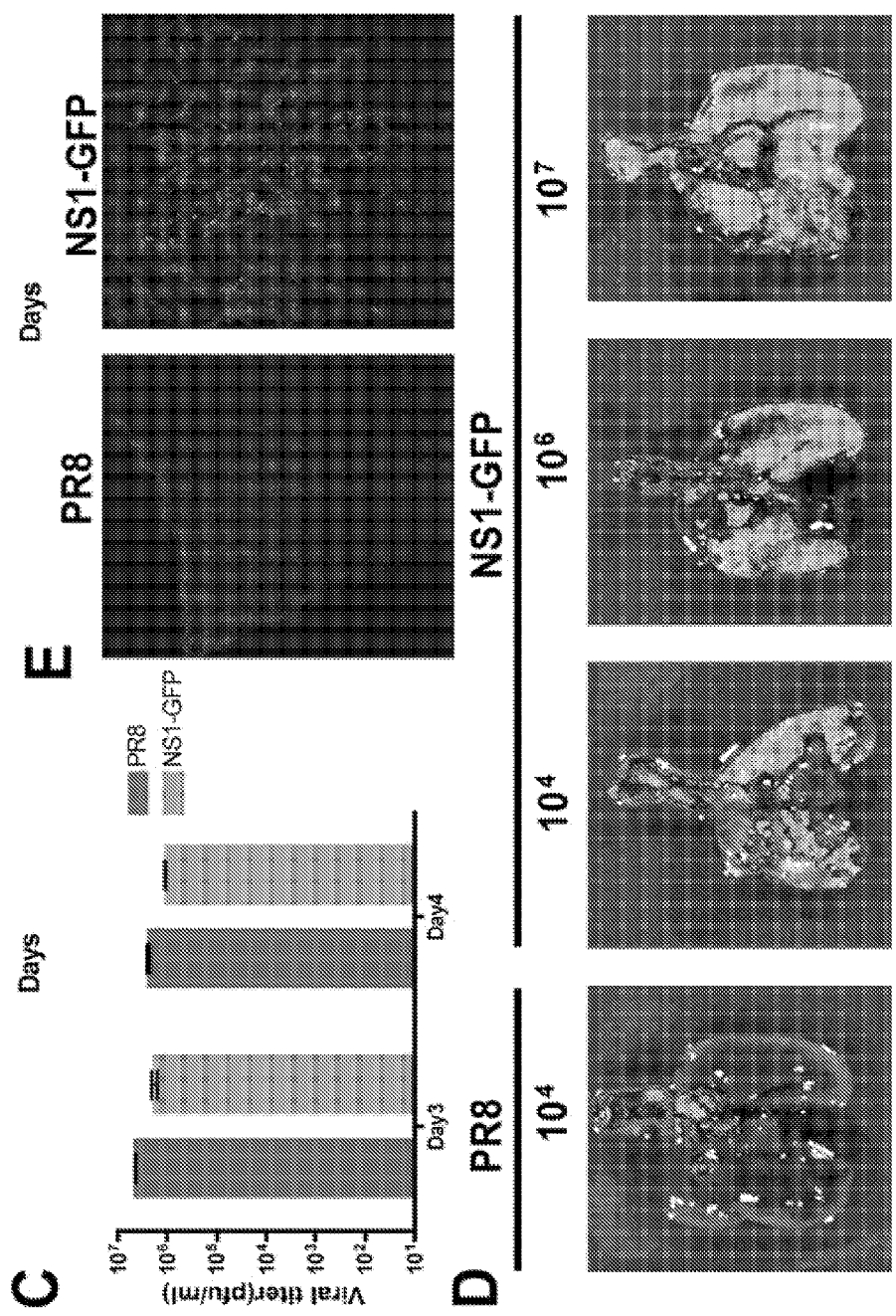

The viral titers in the lungs of infected mice were then determined on day 3 and day 4 post-infection (FIG. 10C). The NS1-GFP virus replicated efficiently in the lower respiratory tract of mice and grew to nearly $5 \times 10^6$ pfu/ml, only 2-fold lower than Wt PR8 virus. This slight reduction in replication is likely to account for the increase in $LD_{50}$.

Whole-Organ Imaging of NS1-GFP Virus Replication.

In order to longitudinally follow the course of infection progression in the lungs of infected mice, the NS1-GFP virus infected mice were imaged using an IVIS-200 series system (Xenogen Corporation). Five-week old BALB/c mice were infected with Wt PR8 ($10^4$ pfu) or NS1-GFP virus with different doses ($10^4$, $10^6$ and $10^7$ pfu). Wt PR8 infected mice were used as controls for background fluorescence. The background fluorescence from skin and tissues surrounding the ribcage precluded an in depth analysis of GFP expression in the lung of anesthetized mice following virus infection. To overcome this, animals were euthanized, and their lungs were excised and imaged ex vivo on day 4 post-infection (FIG. 10D). Upon viral infection, the level of fluorescence from the lungs of NS1-GFP virus infected mice was significantly higher than in Wt PR8 infected mice (background), indicating active replication of NS1-GFP virus in the lower respiratory tract of infected mice (FIG. 10D). A good correlation between the amount of viral inoculum and the fluorescence signal from NS1-GFP virus infected lungs was observed, with fluorescence intensity increasing as the dose of the inoculum increased. Furthermore, examination of cryosections of NS1-GFP virus infected lungs also showed infected cells expressing NS1-GFP protein (FIG. 10E).

Kinetics of NS1-GFP Virus Infection in Mice

Previous studies have shown that IAV infects both epithelial ($CD45^-$) and hematopoietic ($CD45^+$) cells in vitro (8, 17-20). To understand the in vivo dynamics of IAV infection progression and to identify the specific cells types susceptible to IAV infection, BALB/c mice were infected with NS1-GFP virus and then analyzed for GFP positive cells in lung homogenates using multicolor flow cytometry. Representative plots of the flow cytometric analysis of GFP in different cell types are shown in FIGS. 11 and 12.

Figures 13A, 13B:
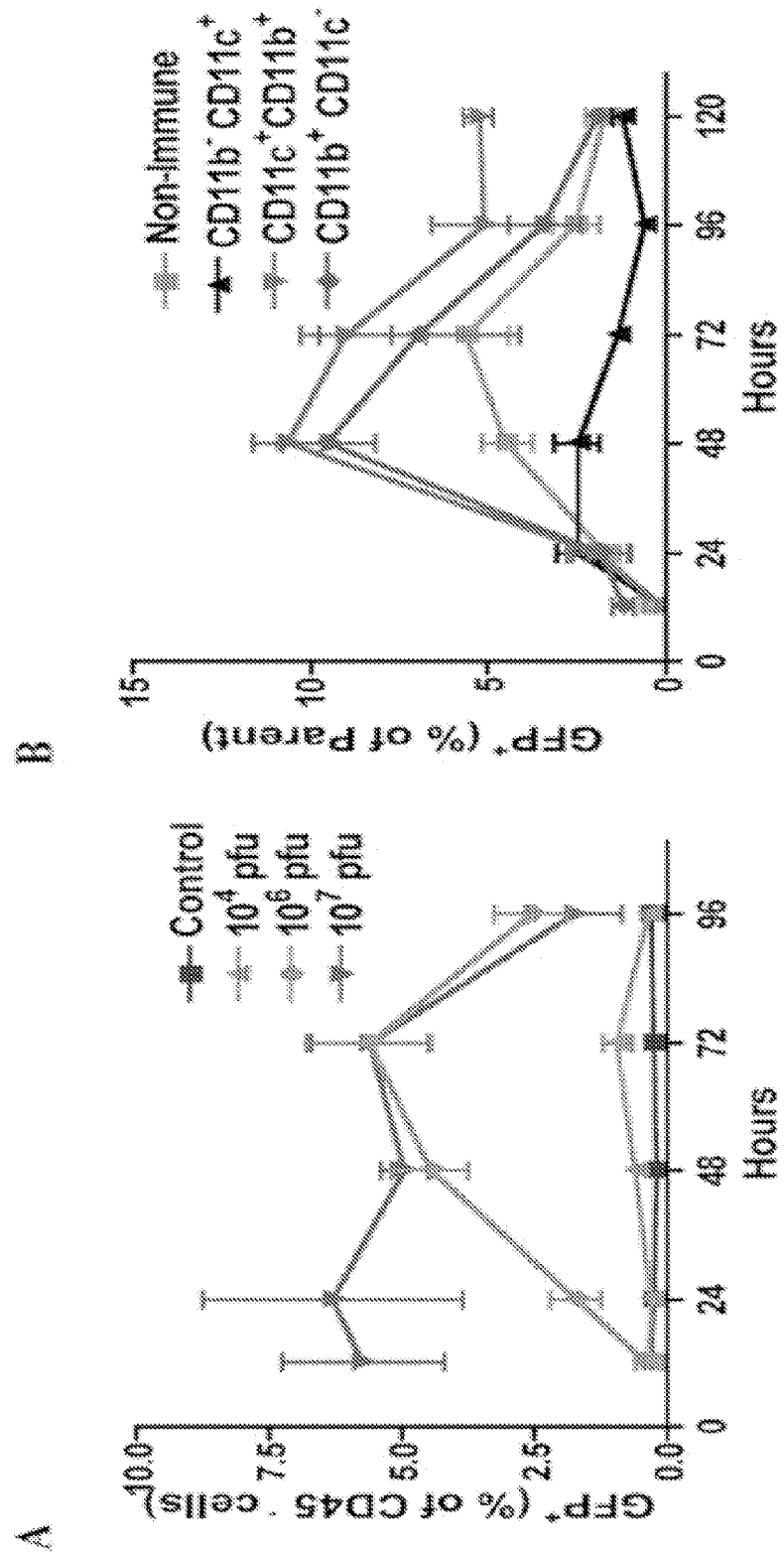

To find the optimal viral dose that would enable the kinetics of infection to be followed, mice were infected intranasally with NS1-GFP virus at different doses ($10^4$, $10^6$, and $10^7$ pfu) and the course of infection of non-hematopoietic cells ($CD45^-$) was analyzed at different times post-infection (FIG. 13A). Flow cytometry analysis of lung cells showed an increase in the number of infected cells as the NS1-GFP viral inoculum increased, correlating well with the results from ex vivo imaging. In the $10^7$ pfu-infected mice GFP-positive cells were seen as early as 12 hpi with nearly 6% of $CD45^-$ cells being GFP-positive and these infection levels were sustained up to 72 hpi. At 96 hpi, the number of GFP positive cells decreased by nearly 3-fold. The $10^6$ pfu infected group showed a kinetic pattern of GFP positive cells with numbers peaking around 48-72 hpi at levels similar to the $10^7$ pfu infected group. However, in the $10^4$ pfu infected mice, despite showing severe pathogenicity, only 1% of $CD45^-$ cells were GFP positive (2-3 fold higher than background levels; FIG. 13A). Based on these data, subsequent experiments were performed with a dose of $10^6$ pfu.

Next, the expression of NS1-GFP in various subsets of antigen presenting cells (APC) was examined based on the surface expression patterns of CD11b and CD11c. Mice were intranasally inoculated with $10^6$ pfu of NS1-GFP virus and the lung homogenates were analyzed for GFP presence in APC's using antibodies specific for CD11b and CD11c surface markers, at 12, 24, 48, 72, and 120 hpi (FIG. 13B). At 12 hpi, a minimal number of cells expressing NS1-GFP (less than 1%) was observed. However after 24 hpi, the number of GFP containing cells increased. At 48 hpi, nearly 10% of the $CD11b^+$ $CD11c^+$ (conventional DCs) and $CD11b^+$ $CD11c^-$ (monocytes and neutrophils) cells carried NS1-GFP. At this time only 2-3% of $CD11b^-$ $CD11c^+$ (macrophages and dendritic cells) were GFP positive. After 96 hpi, the numbers of GFP-positive cells started to decline, and only $CD11b^+$ $CD11c^+$ cells carried significantly higher levels of NS1-GFP (~6%). In addition, a significant percentage of NK- and B cells were also GFP positive, suggesting that these cells are targets of IAV infection (FIG. 14; No treatment). A minor portion of CD4 and CD8 cells carrying GFP was also found (FIG. 4; No treatment). Although macrophages, DC and monocytes are known to be susceptible to IAV infection in vitro, it is possible that in vivo, some of these cells are GFP positive due to uptake of NS1-GFP virus infected cells or from apoptotic cells (17-23).

Effects of Antiviral Treatments on NS1-GFP Infection Progression

Figures 14A, 14B, 14C, 14D:
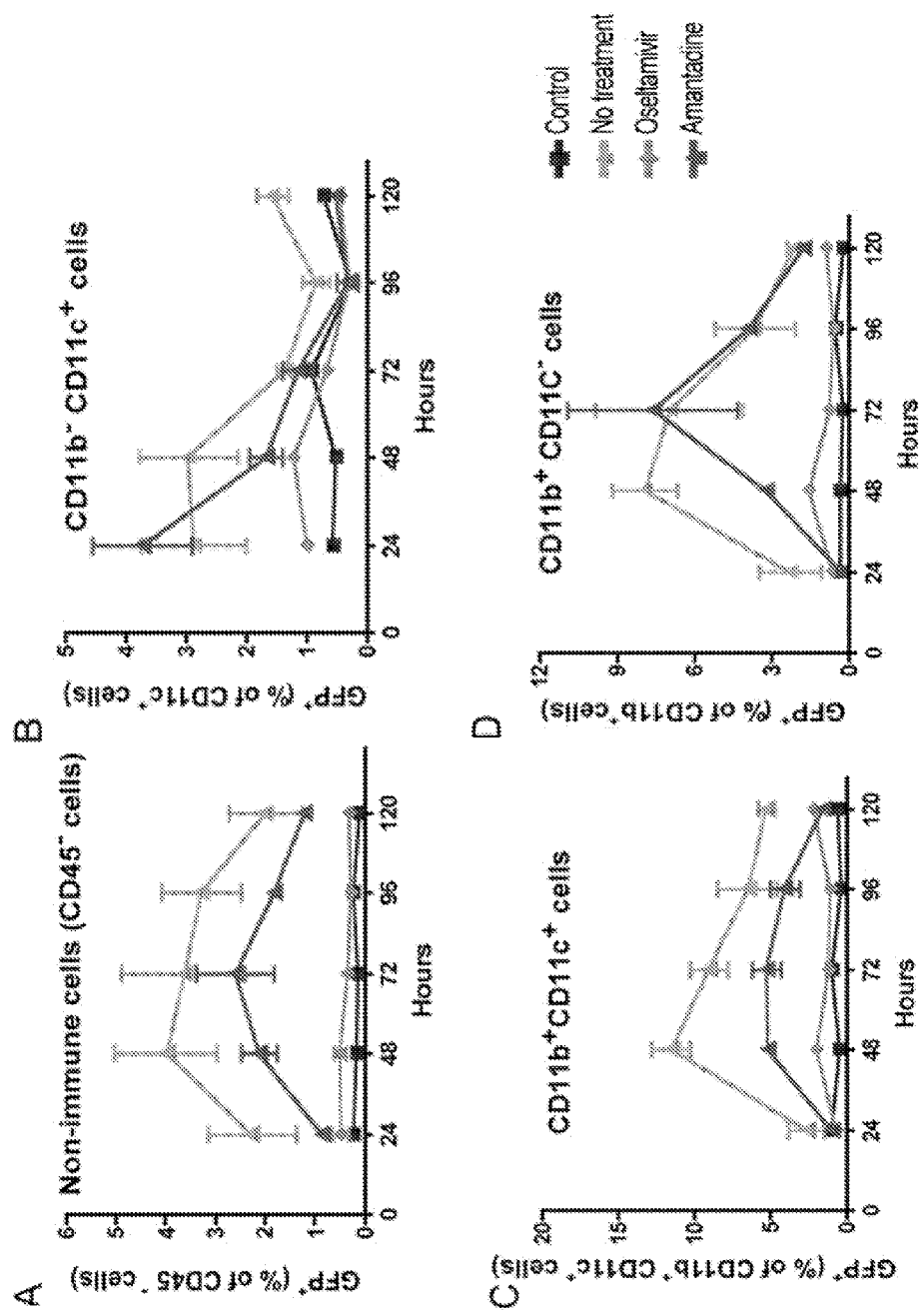
Figures 14E, 14F, 14G, 14H, 14I:
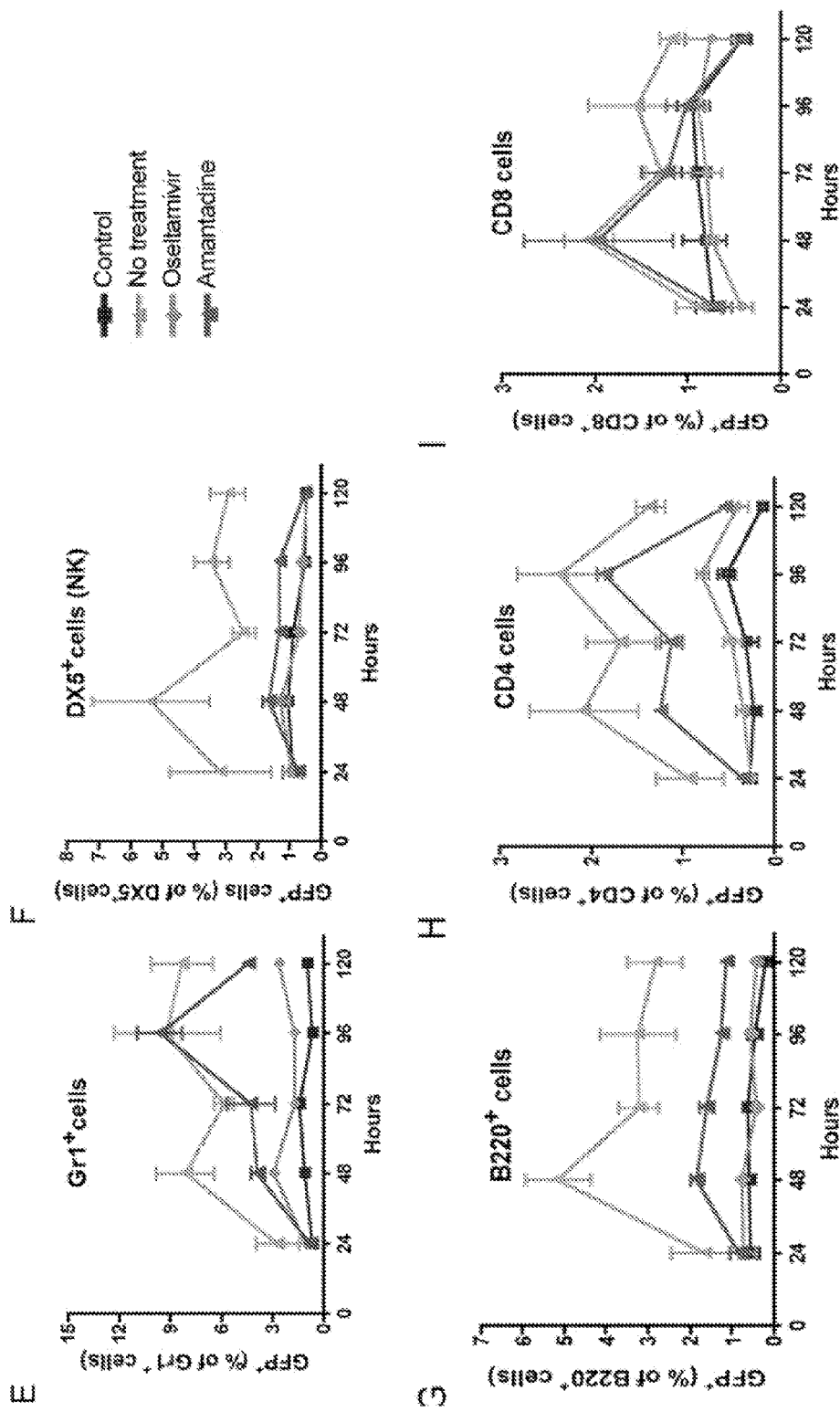

Although vaccination is the most effective means of protection against lethal influenza virus infection, antiviral drugs like amantadine and oseltamivir are recommended for treatment of influenza-like illnesses (4, 5). The mechanisms of action of these drugs have been extensively studied in tissue culture. However, it is unclear how these drugs modulate the progression of viral infection in vivo. To understand how antiviral treatment affects the kinetics of virus infection, mice were infected with $10^6$ pfu of NS1-GFP virus, and treated daily with either amantadine (40 mg/Kg) or oseltamivir (50 mg/Kg), starting 1 hr after infection (24). The effect of antiviral treatments was determined by analyzing NS1-GFP expression in different cells types using multicolor flow cytometry (FIG. 14). In mice that received no antiviral drug, a differential kinetic pattern of NS1-GFP expression was observed in different cell types with the numbers of GFP positive cells peaking at 48-72 hpi. Oseltamivir treatment dramatically reduced infection rate in all of the examined cell types. Only modest levels of GFP positive cells were detected in all cell types (>2%). Interestingly, amantadine treatment was most effective in blocking infection of NK and B cells, but was less potent for other cell types (FIG. 14F, G). Amantadine treatment showed only 50% reduction in infection of epithelial (CD45−) and CD11b$^+$ CD11c$^+$ cells (FIG. 14A, C). This drug was effective in reducing numbers of GFP-positive cells in CD11b$^+$ CD11c$^-$, Gr1$^+$ (infiltrating monocytes) and CD4 cells at early times but not after 72 hpi (FIG. 14D, E, H). Taken together, these results show that oseltamivir treatment controls infection progression in all cell types but amantadine blocks infection in a more cell type specific manner.

Figures 15A, 15B:
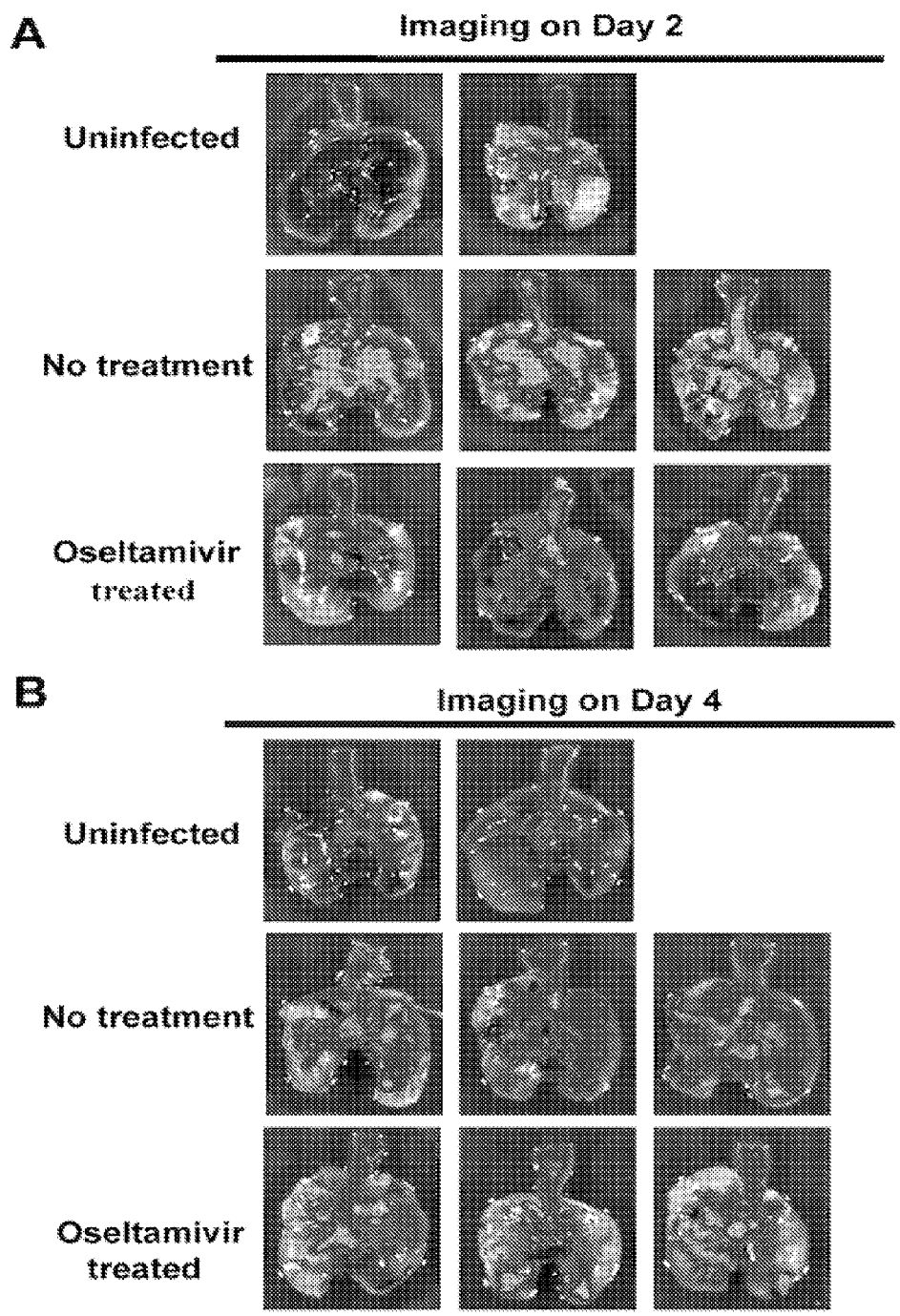

To observe the global effects of oseltamivir treatment, ex vivo analysis of whole lungs was performed (FIG. 15). Lungs from uninfected mice were used as controls for background fluorescence. Analysis of mice lungs on day 2 post-infection showed a clear difference in the fluorescence intensities between untreated mice and oseltamivir treated mice (FIG. 15A). In both groups, most of the GFP fluorescence signal was concentrated in areas close to large conducting airways. However, fluorescence intensity was significantly lower in oseltamivir treated mice than in untreated mice (3 to 5 fold lower). Analysis of the untreated group on day 4 post infection showed GFP fluorescence throughout the whole lung, demonstrating the progression of infection into the lungs (FIG. 15B). However, oseltamivir treatment significantly restricted the spread of viral infection since GFP signal was only detected in localized spots. Together, these data indicate that oseltamivir treatment greatly reduces IAV infection in both epithelial and immune cells, and that infection is restricted to small localized areas in the lung, which may represent the initial sites of infection.

In Vivo and In Vitro Stability of GFP Expression by the NS1-GFP Virus

Figures 16A, 16B, 16C:
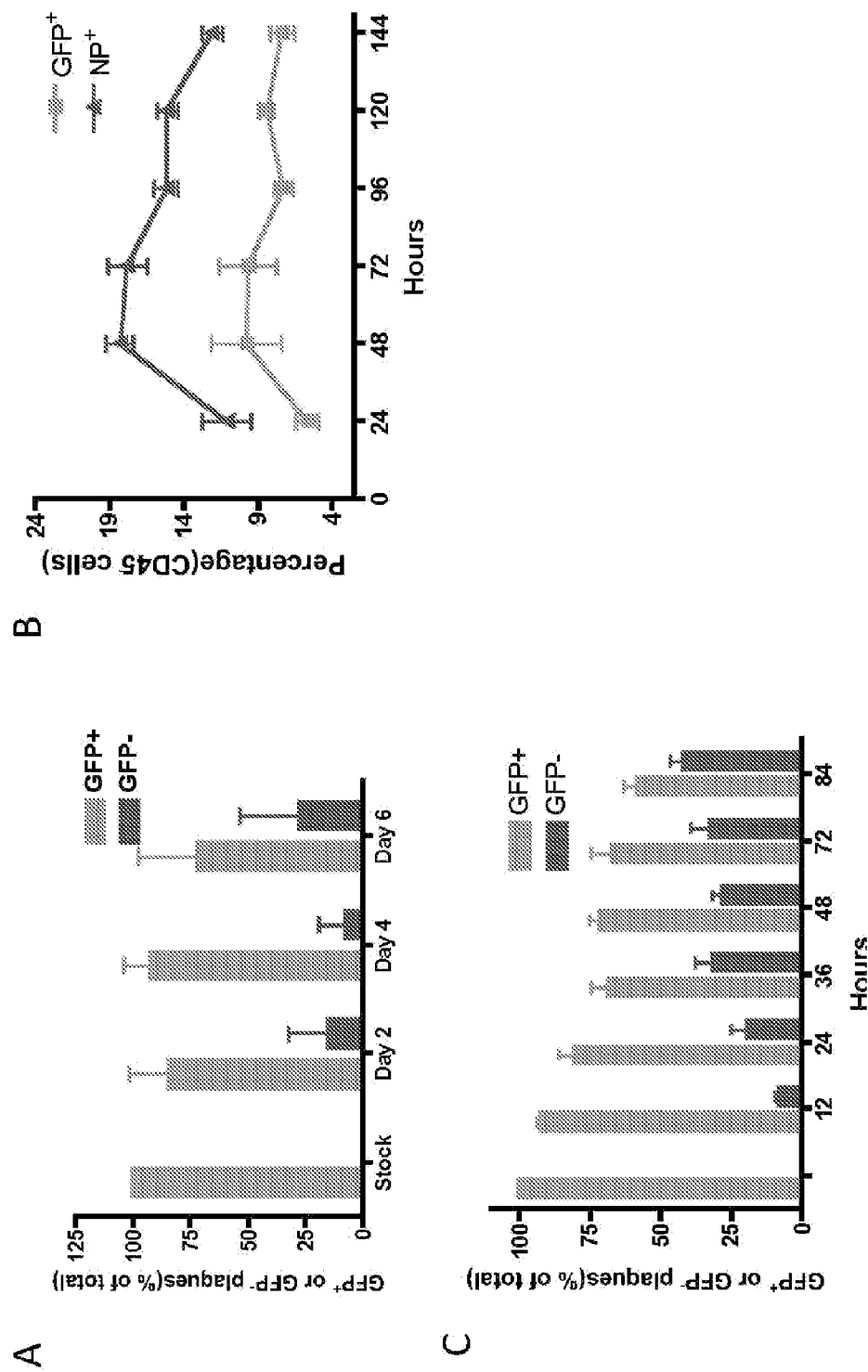

Although NS1-GFP virus replicated in mice, in the lung homogenates, a mixture of GFP-positive and GFP-negative viruses was observed, suggesting that some of the viruses may carry deletions in the GFP transgene. To fully evaluate the in vivo stability of NS1-GFP virus, mice were infected with $10^4$ pfu of NS1-GFP virus and the percentage of GFP carrying virus in the lung homogenates were assessed on day 2, 4 and 6, by scoring for GFP positive or negative plaques (FIG. 16A). The viral stocks used for mice infection served as controls. The percentage of GFP-positive and GFP-negative plaques varied among individual mice. Nearly 15% of plaques were GFP negative in the day 2 and 4 lung homogenates. However, in the lung homogenates from day 6 post infection, nearly 30% of plaques were GFP negative, suggesting increased loss of GFP or active replication of GFP deletion viruses. To assess the kinetics of stability of the GFP transgene in mice, GFP expression was compared with viral nucleoprotein NP expression in non-immune cells (CD45$^-$) in mice infected with $10^6$ pfu of NS1-GFP virus. Unlike immune cells that can carry GFP by phagocytosis of infected cells, non-immune cells are expected to carry GFP only if they are infected. At 24 hpi, the percentage of NP$^+$ cells was twice the percentage of GFP$^+$ cells (FIG. 16B). At this time during infection, the higher number of NP$^+$ cells was unlikely from the emergence of GFP deletion virus, but rather due the early expression of NP compared to NS1-GFP. During the course of infection, both the populations followed similar kinetic patterns. This is in correlation with the plaque assay data that majority of the virus population carry GFP (FIG. 16A).

Next, the stability of NS1-GFP virus in vitro during a multi-cycle replication in MDCK cells was examined. MDCK cells were infected with an MOI of 0.001, and the levels of GFP positive and GFP negative viruses in the supernatants were examined by plaque assay at various hpi (FIG. 16C). At 12 hpi, nearly 5-10% of plaques were GFP negative. During multi-cycle replication, the number of GFP negative viruses increased from 25 to 45%, suggesting better growth of viruses carrying deletions in GFP gene. Nevertheless, it is possible to generate clonal populations of the NS1-GFP virus from single plaques with more than 99% of GFP positive viruses.

7.4 Discussion

In this example, the generation of a fully replication competent influenza GFP reporter virus was reported. The NS1-GFP virus was attenuated for multi-cycle replication in MDCK cells and in mice. Nevertheless, the NS1-GFP virus was still pathogenic in mice. This phenotype allowed for the first time the monitoring of influenza A virus infected cells in vivo using a fluorescent reporter gene during infection with a lethal dose of influenza virus. Whole organ imaging of lungs of mice infected with NS1-GFP virus was consistent with influenza virus infection starting in the large conducting airways and later spreading to the bronchioles and deeper areas in the lungs. Although there was background fluorescence in the large conducting airways of uninfected mice, the fluorescence intensity in the large conducting airways of NS1-GFP virus infected mice (ROI intensity=203.50±41.36) was nearly two-fold higher than the uninfected mice (ROI intensity=108.39±14.56). The in vivo dynamics of IAV infection was also analyzed by flow cytometry and GFP was observed in epithelial and hematopoietic cells including macrophages, monocyte, neutrophils, respiratory dendritic cells, B-, NK-, CD4- and CD8 cells. Treatment of mice with a NA inhibitor dramatically reduced virus spreading to all cell types. However, treatment with a M2 inhibitor effectively reduced infection of B and NK cells but only showed a modest effect in blocking infection of other cells, suggesting that B and NK cells are more susceptible to the antiviral action of amantadine. This differential susceptibility of cell populations in vivo to the antiviral effects of two different influenza virus drugs is likely to have implications for control of disease progression and the induction of immune responses.

In the NS1-GFP virus reported here, the GFP reporter was introduced in the middle of the NS segment to prevent any detrimental effect on vRNA packaging signals present in the 3' and 5' ends. The NS1-GFP virus was designed to express NS1-GFP and NEP as a single fusion protein (NS1-GFP-2A-NEP) (FIG. 7A), in which NEP, which is essential for virus survival, was separated from NS1-GFP protein by an autoproteolytic cleavage reaction at 2A site.

In mice, the NS1-GFP virus caused significant pathogenicity, evidenced by significant loss of body weight and 100% lethality at doses ≥$10^4$ pfu (FIG. 10B, FIG. 9B). All the mice infected with $10^4$ pfu of NS1-GFP virus reached the experimental end point by day 9. Also, NS1-GFP virus replicated efficiently in the lower respiratory tract of infected mice (FIG. 10C). Interestingly, nearly 5-30% of the GFP negative viruses were noticed in the mouse lung homogenates, indicating that these of viruses are likely carrying deletions in the GFP (FIG. 16A). In multiple analyses of NS1-GFP virus stocks, GFP negative plaques were not found (limit >10 pfu). The GFP-negative viruses may arise due to selection pressure for viruses that contain deletions or mutations at specific regions of NS-GFP segment which result in more fit viruses in vivo. This is in contrast to non-segmented negative strand RNA viruses, which are known to stably maintain GFP and other reporter genes inserted in their genomes after multiple passages (25). Since nearly 70% of the virus population in the lungs of infected animals remained GFP positive (day 6), suggesting that the analysis has not been affected by loss of GFP expression during infection.

Previous studies have shown that IAV preferentially replicate in tracheal epithelial cells (8, 26). Here, the sites of initial viral replication and the spreading from these sites were analyzed in the mouse model by performing whole organ imaging of NS1-GFP infected lungs. Ex vivo imaging of NS1-GFP virus infected lungs revealed that GFP fluorescence signal was mainly present in areas closer to large conducting airways during the initial stages of infection, suggesting active replication of the NS1-GFP virus in this region (FIG. 15A, No treatment). At later stages of infection, GFP signal was seen throughout the lung, indicating the spreading of NS1-GFP virus deeper into the bronchioles and possibly into the alveoli spaces (FIG. 15B, No treatment; FIG. 10D). Treatment of infected mice with oseltamivir effectively blocked viral spreading and NS1-GFP virus replication was observed in confined regions in the lungs. This is in agreement with data from in vitro studies, which have demonstrated that oseltamivir restricts viral spreading by blocking release of progeny virions from infected cells (reviewed in (4)). It is important to note that sites of IAV replication and viral spreading in lungs are determined by several viral/host factors, including the origin of virus (avian or human), the HA receptor specificity, distribution of susceptible cells, sialic acid receptor distributions and temperature (27, 28). It has been proposed that these factors contribute to impaired human-to-human transmission of highly pathogenic H5N1 virus (29). Thus, recombinant influenza viruses expressing NS1-GFP and derived from different strains might be used in the future to address these questions in different animal models.

Flow cytometric analysis of infected lung homogenates revealed the kinetics of IAV infection in different cell types. Mice were infected with different doses ($10^4$, $10^6$ or $10^7$ pfu) of NS1-GFP virus and the infection progression was followed in different cell types. In the $10^7$ pfu group, during the early stages of infection GFP expression was seen mostly in non-immune $CD45^-$ cells (12-24 hpi), indicating that these cells are the primary targets of IAV infection, and only after 24 hpi was GFP expression detected in hematopoietic cells (FIG. 13). The percentage of GFP-positive epithelial cells remained nearly 6% from 12-72 hpi. However, in mice infected with $10^6$ pfu, a kinetic pattern of infection progression was observed. The number of infected cells in different cell types remained below 1% at 12 hpi, but increased over time reaching a peak at 48-72 hpi. A distinct pattern of susceptibility to infection by the NS1-GFP virus for different immune cells was observed in the following order $CD11b^{+CD}11c^+>Gr1^+>CD11b^+$ $CD11c^->CD11b^-CD11c^+$. NS1-GFP was also present B, NK, CD4 and CD8 cells (FIG. 14). At 72 hpi, the number of GFP positive cells declined probably due to clearance of infected cells by the immune system and to migration of DC's to draining lymph nodes. It is worthwhile noting that some of these cells actively take up foreign antigen and cell debris; so it is possible that some these cells are not infected but rather carry the debris of infected cells (30).

Several studies have shown that highly pathogenic viruses like the 1918 H1N1 virus and H5N1 viruses induce massive infiltration of inflammatory cells (monocytes and neutrophils) very early during infection and that these viruses can replicate efficiently in these cells (31-33). Also, mice infected with highly pathogenic H5N1 viruses show a decrease in numbers of lymphocytes (34). Interestingly, in this study, NS1-GFP was found in hematopoietic cells, especially in DCs, monocytes ($Gr1^+$), neutrophils ($CD11b^+$), B-, and NK cells, which are critical for controlling viral replication and development of effective adaptive immunity (35, 36). It is conceivable that highly pathogenic influenza viruses may infect high levels of these cells and/or have preferential cellular tropism for immune cells and thereby contributing to immune deregulation and disease aggravation.

Anti-influenza drugs like amantadine and oseltamivir are widely used for treatment of influenza-like illness (6, 7). Although the mechanism of action for these drugs has been well characterized in vitro, it is still unclear how they control infection progression in vivo (1, 4, 9, 10). Here, the effect of antiviral treatment on NS1-GFP virus infection progression was analyzed in vivo. Oseltamivir treatment significantly reduced NS1-GFP virus infection in all cell types to less than 2% and restricted the NS1-GFP virus replication to localized areas (FIGS. 14 and 15). Amantadine was more effective in preventing infection in B and NK cells (3-4 fold), but it reduced infection only to 50% in epithelial and $CD11c^+$ $CD11b^+$ cells at the used dose (FIG. 4A, C). Interestingly, amantadine treatment showed no effect in preventing infection of monocytes ($Gr1^+$) or neutrophils ($CD11b^+$) at later times of infection (FIG. 4E, D). Since the ion channel activity of M2s are required for acidification of the inside of the virion during endosome-mediated viral entry, it is possible that differences in the endosomal physiology of different cell types are responsible for these effects. Also, the levels of inflammatory monocyte and neutrophil infiltration were different in oseltamivir and amantadine treated mice. In oseltamivir treated mice, the number of infiltrating cells were dramatically lower than in amantadine treated mice, correlating well with the levels of antigen present in the respiratory tract. This is in agreement with prior studies which have demonstrated that the viral load in the lungs determines the levels of immune infiltration (33).

In conclusion, this study has demonstrated the generation of the first, fully replication competent IAV carrying a GFP reporter gene (NS1-GFP virus). The NS1-GFP virus efficiently replicates and causes significant pathogenicity in mice. By multicolor flow cytometric analysis, cell types that are GFP positive during infection have been analyzed. The results of this study provide a basis for future examination of the consequences of infection of different cell populations. In addition, the generation of different influenza virus strains carrying a GFP reporter will allow further and more specific investigation of strain specific effects in pathogenesis, tissue tropism and replication kinetics in different hosts in vivo. Finally, the same strategy could be adapted to generate recombinant influenza viruses carrying foreign genes in their NS segments, which can be used as a vaccines or gene therapy candidates.

7.5 References

1. Schnell J R & Chou J J (2008) Structure and mechanism of the M2 proton channel of influenza A virus. (Translated from eng) *Nature* 451(7178):591-595.
2. Fodor E, et al. (1999) Rescue of influenza A virus from recombinant DNA. (Translated from eng) *J Virol* 73(11): 9679-9682 (in eng).
3. Reed & Muench (1938) A simple method of estimating fifty percent endpoints. *The American Journal of Hygiene* 27(3):493-497.
4. von Itzstein M (2007) The war against influenza: discovery and development of sialidase inhibitors. *Nat Rev Drug Discov* 6(12):967-974.
5. De Clercq E (2006) Antiviral agents active against influenza A viruses. *Nat Rev Drug Discov* 5(12):1015-1025.
6. Hayden F G & Pavia A T (2006) Antiviral management of seasonal and pandemic influenza. *J Infect Dis* 194 Suppl 2:S119-126.
7. Sugrue R J, Tan B H, Yeo D S, & Sutejo R (2008) Antiviral drugs for the control of pandemic influenza virus. *Ann Acad Med Singapore* 37(6):518-524.
8. Ibricevic A, et al. (2006) Influenza virus receptor specificity and cell tropism in mouse and human airway epithelial cells. *J Virol* 80(15):7469-7480.
9. Lew W, Chen X, & Kim C U (2000) Discovery and development of GS 4104 (oseltamivir): an orally active influenza neuraminidase inhibitor. *Curr Med Chem* 7(6):663-672.
10. Pielak R M, Schnell J R, & Chou J J (2009) Mechanism of drug inhibition and drug resistance of influenza A M2 channel. *Proc Natl Acad Sci USA* 106(18):7379-7384.
11. Basler C F, et al. (2001) Sequence of the 1918 pandemic influenza virus nonstructural gene (NS) segment and characterization of recombinant viruses bearing the 1918 NS genes. *Proc Natl Acad Sci USA* 98(5):2746-2751.
12. Donnelly M L, et al. (2001) The 'cleavage' activities of foot-and-mouth disease virus 2A site-directed mutants and naturally occurring '2A-like' sequences. *J Gen Virol* 82(Pt 5):1027-1041.
13. Quinlivan M, et al. (2005) Attenuation of equine influenza viruses through truncations of the NS1 protein. *J Virol* 79(13):8431-8439.
14. Kochs G, Garcia-Sastre A, & Martinez-Sobrido L (2007) Multiple anti-interferon actions of the influenza A virus NS1 protein. *J Virol* 81(13):7011-7021.
15. Garcia-Sastre A, et al. (1998) Influenza A virus lacking the NS1 gene replicates in interferon-deficient systems. *Virology* 252(2):324-330.
16. Reed & Muench (1938) A simple method of estimating fifty percent endpoints. *The American Journal of Hygiene* 27(3):493-497.
17. Hao X, Kim T S, & Braciale T J (2008) Differential response of respiratory dendritic cell subsets to influenza virus infection. *J Virol* 82(10):4908-4919.
18. Kim T S & Braciale T J (2009) Respiratory dendritic cell subsets differ in their capacity to support the induction of virus-specific cytotoxic CD8+ T cell responses. *PLoS One* 4(1):e4204.
19. Haye K, Burmakina S, Moran T, Garcia-Sastre A, & Fernandez-Sesma A (2009) The NS1 protein of a human influenza virus inhibits type I interferon production and the induction of antiviral responses in primary human dendritic and respiratory epithelial cells. *J Virol* 83(13):6849-6862.
20. Lopez C B, Fernandez-Sesma A, Czelusniak S M, Schulman J L, & Moran T M (2000) A mouse model for immunization with ex vivo virus-infected dendritic cells. *Cell Immunol* 206(2):107-115.
21. Fesq H, Bacher M, Nain M, & Gemsa D (1994) Programmed cell death (apoptosis) in human monocytes infected by influenza A virus. *Immunobiology* 190(1-2): 175-182.
22. Seo S H, Webby R, & Webster R G (2004) No apoptotic deaths and different levels of inductions of inflammatory cytokines in alveolar macrophages infected with influenza viruses. *Virology* 329(2):270-279.
23. Cheung C Y, et al. (2002) Induction of proinflammatory cytokines in human macrophages by influenza A (H5N1) viruses: a mechanism for the unusual severity of human disease? *Lancet* 360(9348):1831-1837.
24. Tumpey T M, et al. (2002) Existing antivirals are effective against influenza viruses with genes from the 1918 pandemic virus. *Proc Natl Acad Sci USA* 99(21):13849-13854.
25. Billeter M A, Naim H Y, & Udem S A (2009) Reverse genetics of measles virus and resulting multivalent recombinant vaccines: applications of recombinant measles viruses. *Curr Top Microbiol Immunol* 329:129-162.
26. Pekosz A, Newby C, Bose P S, & Lutz A (2009) Sialic acid recognition is a key determinant of influenza A virus tropism in murine trachea epithelial cell cultures. *Virology* 386(1):61-67.
27. Scull M A, et al. (2009) Avian Influenza virus glycoproteins restrict virus replication and spread through human airway epithelium at temperatures of the proximal airways. *PLoS Pathog* 5(5):e1000424.
28. van Riel D, et al. (2006) H5N1 Virus Attachment to Lower Respiratory Tract. *Science* 312(5772):399.
29. Shinya K, et al. (2006) Avian flu: influenza virus receptors in the human airway. *Nature* 440(7083):435-436.
30. Hashimoto Y, Moki T, Takizawa T, Shiratsuchi A, & Nakanishi Y (2007) Evidence for phagocytosis of influenza virus-infected, apoptotic cells by neutrophils and macrophages in mice. *J Immunol* 178(4):2448-2457.
31. Tumpey T M, et al. (2004) Pathogenicity and immunogenicity of influenza viruses with genes from the 1918 pandemic virus. *Proc Natl Acad Sci USA* 101(9):3166-3171.
32. Tumpey T M, et al. (2005) Pathogenicity of influenza viruses with genes from the 1918 pandemic virus: functional roles of alveolar macrophages and neutrophils in limiting virus replication and mortality in mice. *J Virol* 79(23):14933-14944.
33. Perrone L A, Plowden J K, Garcia-Sastre A, Katz J M, & Tumpey T M (2008) H5N1 and 1918 pandemic influenza virus infection results in early and excessive infiltration of macrophages and neutrophils in the lungs of mice. PLoS Pathog 4(8):e1000115.
34. Tumpey T M, Lu X, Morken T, Zaki S R, & Katz J M (2000) Depletion of lymphocytes and diminished cytokine production in mice infected with a highly virulent influenza A (H5N1) virus isolated from humans. *J Virol* 74(13): 6105-6116.
35. Gazit R, et al. (2006) Lethal influenza infection in the absence of the natural killer cell receptor gene Ncr1. *Nat. Immunol* 7(5):517-523.
36. McGill J, Heusel J W, & Legge K L (2009) Innate immune control and regulation of influenza virus infections. *J Leukoc Biol* 86(4):803-812.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A pathogenic recombinant influenza virus comprising a nucleic acid sequence comprising a modified influenza virus nonstructural (NS) gene segment or the complement thereof, wherein the modified influenza virus NS gene segment comprises in 3' to 5' order:
   (a) (i) an influenza virus nonstructural protein 1 (NS1) open reading frame (ORF) lacking a stop codon, (ii) a heterologous nucleotide sequence encoding a detectable substance, (iii) a cleavage site, and (iv) an influenza virus nuclear export protein (NEP) ORF, wherein the modified influenza virus NS gene segment has one or more mutations in either the splice acceptor site, the splice donor site, or both the splice acceptor and splice donor sites that prevents splicing of mRNA, and wherein the modified influenza virus NS gene segment encodes (1) a fusion protein comprising NS1 and the detectable substance and (2) a protein comprising NEP; or
   (b) (i) an influenza virus NS1 ORF lacking a stop codon, (ii) a linker, (iii) a heterologous nucleotide sequence encoding a detectable substance, (iv) a cleavage site, and (v) an influenza virus NEP ORF, wherein the modified influenza virus NS gene segment has one or more mutations in either the splice acceptor site, the splice donor site, or both the splice acceptor and splice donor sites that prevents splicing of mRNA, and wherein the modified influenza virus NS gene segment encodes (1) a fusion protein comprising NS1, the amino acids encoded by the linker, and the detectable substance, and (2) a protein comprising NEP.

2. A recombinant pathogenic influenza virus comprising a nucleic acid sequence comprising a modified influenza virus NS gene segment or the complement thereof, wherein the modified influenza virus NS gene segment comprises in 3' to 5' order: (i) an influenza virus NS1 open reading frame (ORF) lacking a stop codon, (ii) a heterologous nucleotide sequence encoding a detectable substance, (iii) a cleavage site, and (iv) an influenza virus NEP ORF, wherein the modified influenza virus NS gene segment has more than one mutation in the splice acceptor site that prevents splicing of mRNA, and wherein the modified influenza virus NS gene segment encodes (1) a fusion protein comprising NS1 and the detectable substance and (2) a protein comprising NEP.

3. The recombinant influenza virus of claim 1, wherein the modified influenza virus comprises an influenza virus NS1 ORF lacking a stop codon, a heterologous nucleotide sequence encoding a detectable substance, a cleavage site, and an influenza virus NEP ORF.

4. The recombinant influenza virus of claim 3, wherein the modified influenza virus NS gene segment further comprises a linker between the heterologous nucleotide sequence encoding a detectable substance and the cleavage site.

5. The recombinant influenza virus of claim 1, wherein the cleavage site is a 2A cleavage site.

6. The recombinant influenza virus of claim 5, wherein the 2A cleavage site is ATNFSLLKQAGDVEENPG⇓P (SEQ ID NO: 20).

7. The recombinant influenza virus of claim 2, wherein the cleavage site is a 2A cleavage site.

8. The recombinant influenza virus of claim 7, wherein the 2A cleavage site is ATNFSLLKQAGDVEENPG⇓P (SEQ ID NO: 20).

9. The recombinant influenza virus of claim 1, wherein the detectable substance is horseradish peroxidase, alkaline phosphatase, beta-galactosidase, acetylcholinesterase, a prosthetic group, strepavidin/biotin, avidin/biotin, luciferase, luciferin, green fluorescent protein, red fluorescent protein, and aequorin.

10. The recombinant influenza virus of claim 2, wherein the detectable substance is horseradish peroxidase, alkaline phosphatase, beta-galactosidase, acetylcholinesterase, a prosthetic group, strepavidin/biotin, avidin/biotin, luciferase, luciferin, green fluorescent protein, red fluorescent protein, and aequorin.

11. A DNA encoding the modified NS gene segment of the recombinant influenza virus of claim 1.

12. A DNA encoding the modified NS gene segment of the recombinant influenza virus of claim 2.

13. A substrate comprising the recombinant influenza virus of claim 1, wherein the substrate comprises isolated host cells or eggs, wherein the eggs are chicken or poultry eggs.

14. A substrate comprising the recombinant influenza virus of claim 2, wherein the substrate comprises isolated host cells or eggs, wherein the eggs are chicken or poultry eggs.

15. A pharmaceutical composition comprising the recombinant influenza virus of claim 1.

16. An immunogenic composition comprising the recombinant influenza virus of claim 1.

17. A method for eliciting antibodies against an influenza virus or a heterologous antigen, comprising administering to a non-human subject the immunogenic composition of claim 16.

18. A method for generating a recombinant influenza virus, wherein the method comprises introducing into a host cell the DNA of claim 11, wherein the host cell expresses all other components for generation of the influenza virus; and purifying the influenza virus from the supernatant of the host cell.

19. A method for propagating a recombinant influenza virus, wherein the method comprises infecting a substrate with the recombinant influenza virus of claim 1 and purifying the virus subsequently from the substrate.

20. A screening assay to identify a compound that modulates the replication of an influenza virus, comprising:
(a) (i) contacting a compound with a host cell infected with the recombinant influenza virus of claim 1, wherein the recombinant influenza virus expresses the detectable substance, and (ii) measuring the expression or activity of a product encoded by the detectable substance;
(b) (i) infecting a host cell with the recombinant influenza virus of claim 1 in the presence of a compound, wherein the recombinant influenza virus expresses the detectable substance, and (ii) measuring the expression or activity of a product encoded by the detectable substance; or
(c) (i) contacting a compound with a host cell, (ii) infecting the host cell with the recombinant influenza virus of claim 1, wherein the recombinant influenza virus expresses the detectable substance, and (iii) measuring the expression or activity of a product encoded by the detectable substance,
wherein a compound that increases the replication of influenza virus is identified if the level of expression or activity of the product is increased in the host cell contacted with the compound relative to the level of expression or activity of the product in a host cell contacted with a negative control; and wherein a compound that decreases the replication of influenza virus is identified if the level of expression or activity of the product is decreased in the host cell contacted with the compound relative to the level of expression or activity of the product in a host cell contacted with a negative control.

* * * * *